(12) United States Patent
Fontana et al.

(10) Patent No.: US 9,096,544 B2
(45) Date of Patent: Aug. 4, 2015

(54) THERAPEUTIC COMPOUNDS

(75) Inventors: Joseph A. Fontana, Detroit, MI (US); Marcia Dawson, La Jolla, CA (US); Zebin Xia, La Jolla, CA (US)

(73) Assignees: Wayne State University, Detroit, MI (US); Department of Veterans Affairs, Washington, DC (US); Sanford-Burnham Medical Research Institute, LaJolla, CA (US)

( * ) Notice: Subject to any disclaimer, the term of this patent is extended or adjusted under 35 U.S.C. 154(b) by 160 days.

(21) Appl. No.: 13/519,098

(22) PCT Filed: Dec. 23, 2010

(86) PCT No.: PCT/US2010/062074
§ 371 (c)(1),
(2), (4) Date: Dec. 20, 2012

(87) PCT Pub. No.: WO2011/079305
PCT Pub. Date: Jun. 30, 2011

(65) Prior Publication Data
US 2013/0137699 A1    May 30, 2013

Related U.S. Application Data

(60) Provisional application No. 61/289,977, filed on Dec. 23, 2009.

(51) Int. Cl.
| | |
|---|---|
| *C07D 213/55* | (2006.01) |
| *C07D 237/08* | (2006.01) |
| *C07D 239/26* | (2006.01) |
| *A61K 31/505* | (2006.01) |
| *C07D 241/12* | (2006.01) |
| *A61K 31/4965* | (2006.01) |
| *A61K 31/497* | (2006.01) |
| *C07D 213/06* | (2006.01) |
| *C07D 213/60* | (2006.01) |
| *C07D 239/42* | (2006.01) |

(52) U.S. Cl.
CPC ............ *C07D 241/12* (2013.01); *A61K 31/497* (2013.01); *A61K 31/4965* (2013.01); *A61K 31/505* (2013.01); *C07D 213/06* (2013.01); *C07D 213/55* (2013.01); *C07D 213/60* (2013.01); *C07D 237/08* (2013.01); *C07D 239/26* (2013.01); *C07D 239/42* (2013.01)

(58) Field of Classification Search
CPC .. C07D 213/06; C07D 213/55; C07D 213/60; C07D 237/08; C07D 239/26; C07D 239/42; C07D 241/12; A61K 31/4965; A61K 31/497; A61K 31/505
USPC ........... 544/224, 335, 336; 546/342; 514/247, 514/252.1, 256, 277
See application file for complete search history.

(56) References Cited

U.S. PATENT DOCUMENTS

| | | |
|---|---|---|
| 4,938,949 A | 7/1990 | Borch et al. |
| 7,053,071 B2 | 5/2006 | Dawson et al. |
| 2004/0235757 A1 | 11/2004 | Sabrina et al. |

FOREIGN PATENT DOCUMENTS

| | | |
|---|---|---|
| WO | WO 03/004501 A2 | 1/2003 |
| WO | WO 03/028733 A1 | 4/2003 |
| WO | WO 2004/004651 A2 | 1/2004 |

OTHER PUBLICATIONS

Simone, Oncology: Introduction, Cecil Textbook of Medicine, 20th Edition, vol. 1, pp. 1004-1101 O, 1996.*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431,2001.*
Pearce et al., Failure modes in anticancer drug discovery and development, Cancer Drug Design and Discovery Edited by Stephen Neidle, Chapter 18, pp. 424-435 (2008).*
Marek, Abstract (The role of the apoptosome in the activation of procaspase-9, Postepy Hig Med Dosw, 67:54-64) Feb. 2013.*
Esposito et al., SHP-1 expression accounts for resistance to imatinib treatement in Philadelphia chromosome-positive cells derived from patients with chronic myeloid leukemia, Blood, vol. 118, No. 13, pp. 3634-3644 (2011).*
Black et al., "Diphtheria toxin-interleukin-3 fusion protein (Dt388IL3) prolongs disease-free survival of leukemic immunocompromised mice", *Leukemia*, 17, 155-159 (2003).

(Continued)

*Primary Examiner* — Deepak Rao
(74) *Attorney, Agent, or Firm* — Viksnins Harris & Padys PLLP

(57) ABSTRACT

The invention provides compounds of formula I or a salt thereof as described herein. The invention also provides pharmaceutical compositions comprising a compound of formula I, processes for preparing compounds of formula I, intermediates useful for preparing compounds of formula I and therapeutic methods for inducing apoptosis or treating cancer using compounds of formula I.

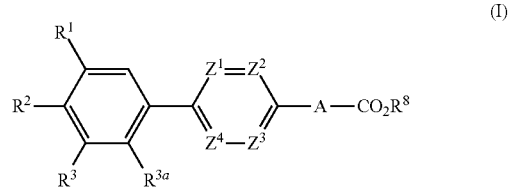

17 Claims, 8 Drawing Sheets

(56) References Cited

OTHER PUBLICATIONS

Dawson et al., "Antagonist analogue of 6-[3'-(1-adamantyl)-4'-hydroxyphenyl]-2-naphthalenecarboxylic acid (AHPN) family of apoptosis inducers that effectively blocks AHPN-induced apoptosis but not cell-cycle arrest", *J. Med. Chem.*, 47, 3518-3536 (2004).

Dawson et al., "An adamantyl-substituted retinoid-derived molecule that inhibits cancer cell growth and angiogenesis by inducing apoptosis and binds to small heterodimer partner nuclear receptor: effects of modifying its carboxylate group on apoptosis, proliferation, and protein-tyrosine phosphatase activity", *J. Med. Chem.*, 50(11), 2622-2639 (2007).

Dawson et al., "Adamantyl-Substituted Retinoid-Derived Molecules that Internact with the Orphan Nuclear Receptor Small Heterodimer Partner: Effects of Replacing the 1-Adamantyl or Hydroxyl Group on Inhibition of Cancer Cell Growth, Induction of Cancer Cell Apoptosis, and Inhibition of Src Homology 2 Domain-Containin", *Journal of Medicinal Chemistry*, vol. 51 (18), 5650-5662 (2008).

Eisenmann et al., "Mitogen-activated protein kinase pathway-dependent tumor-specific survival signaling in melanoma cells through inactivation of the proapoptotic protein bad", *Cancer Res.*, 63, 8330-8337 (2003).

Farhana et al., "Apoptosis induction by a novel retinoid-related molecule requires nuclear factor-kappaB activation", *Cancer Res.*, 65, 4909-4917 (2006).

Farhana et al., "Adamantyl-substituted retinoid-related molecules bind small heterodimer partner and modulate the Sin3A repressor", *Cancer Res.*, 67, 318-325 (2007).

Farhana et al., "SHP and Sin3A expression are essential for adamantyl-substituted retinoid-related molecule-mediated nuclear factor-kappaB activation, c-Fos/c-Jun expression, and cellular apoptosis", *Molecular Cancer Therapeutics*, 8, 1625-1635 (2009).

Farhana et al., "Adamantyl-substituted retinoid-related (ARR) molecules induce apoptosis in human acute myelogenous leukemia cells", *Mol. Cancer Ther.*, 9 (11), 2903-2913 (2010).

Goodman et al., "Desymmetrization of dichloroazaheterocycles", *Tetrahedron*, 55, 15067-15070 (1999).

Jin et al., "cIAP1, cIAP2, and XIAP Act Cooperatively via Nonredundant Pathways to Regulate Genotoxic Stress-Induced Nuclear Factor-κB Activation", *Cancer Res.*, 69(5), 1782-1791 (2009).

McBee et al., "Some dihalo-(trifluoromethyl) benzenes", *J. Am. Chem. Soc.*, 73, 3932-3934 (1951).

Mologni et al., "The Novel Synthetic Retinoid 6-[3-adamantyl-4-hydroxyphenyl]-2-naphthalene Carboxylic Acid (CD437) Causes Apoptosis in Acute Promyelocytic Leukemia Cells Through Rapid Activation of Caspases", *Blood*, 93 (3), 1045-1061, (1999).

Ognyanov et al., "Design of Potent, Orally Available Antagonists of the Transient Receptor Potential Vanilloid 1. Structure—Activity Relationships of 2-Piperazin-1-yl-1*H*-benzimidazoles", *J. Med. Chem.*, 49, 3719-3742 (2006).

Patent Cooperation Treaty, International Searching Authority, Search Report and Written Opinion for PCT/US2010/062074, 8 pages, May 3, 2011.

Van Den Heuvel et al., "Synthesis of a non-heme template for attaching four peptides: an approach to artificial iron(II)-containing peroxidases", *J. Org. Chem.*, 69, 250-262 (2004).

Weise et al., "Retinoic Acid Regulates Aberrant Nuclear Localization of PML-RARα in Acute Promyelocytic Leukemia Cells", *Cell*, 76, 345-354 (1994).

Zhang et al., "Induction of apoptosis of human B-CLL and ALL cells by a novel retinoid and its nonretinoidal analog", *Blood*, 100, 2917-2925 (2002).

Zhang et al., "Induction of apoptosis in retinoid-refractory acute myelogeneous leukemia by a novel AHPN analog", *Blood*, 102(10), 3743-3752 (2003).

\* cited by examiner

3-Cl-AHPC compound 16

B

C

A

THERAPEUTIC COMPOUNDS

CROSS-REFERENCE TO RELATED APPLICATIONS

This patent application claims the benefit of priority of U.S. application Ser. No. 61/289,977, filed Dec. 23, 2009 which application is herein incorporated by reference.

The invention described herein was made with government support under Grant Number RO1 CA109370 awarded by the National Institutes of Health and with government support from the Department of Veterans Affairs. The United States Government has certain rights in the invention.

BACKGROUND OF THE INVENTION

Numerous advances have been made in both the classification and prognosis of acute myelogenous leukemia (AML) based on recent molecular observations. While the inherent heterogenous nature of AML was initially described using the French-American-British classification, the discoveries of unique chromosomal translocations, gene amplification and mutations and their effects on prognosis and response to therapy have resulted in new and more clinically relevant classification systems. Despite these advances, the mainstay for AML treatment has remained chemotherapy. Targeted therapy has played a role in the treatment of selective AML subtypes. Treatment of acute promyelocytic leukemia (APL) with pharmacologic concentrations of trans-retinoic acid (tRA) results in 90% of the patients achieving a complete remission. This dramatic response of APL cells to high concentrations of tRA is due to the presence of a unique t(15:17) reciprocal translocation resulting in the generation of a pro-myelocytic leukemia (PML)-retinoic acid nuclear receptor (RAR)α fusion product which, even in the presence of physiologic concentrations of tRA, displays increased binding to co-repressors and induces maturation arrest at the promyelocyte stage. Exposure of these cells to micromolar concentrations of tRA results in the disassociation of PML-RAR from the co-repressors, enhancing its binding by co-activators with the subsequent initiation of gene transcription. Unfortunately, tRA efficacy is restricted to APL with no activity demonstrated in the other AML subtypes. Moreover, with tRA inducing its own catabolism, maintenance therapy may be ineffective with time. New targeted agents including fms-related tyrosine kinase receptor (FLT-3) and farnesyltransferase inhibitors are being evaluated as potential therapeutic modalities for the treatment of AML.

Adamantyl-substituted retinoid-related (ARR) molecules are a unique class of compounds which have been found to induce apoptosis in a large number of tumor types, many of which display resistance to classical retinoids such as tRA. The mechanism(s) utilized by the ARRs in the induction of cell death is not clear. 6-[3-(1-Adamantyl)-4-hydroxyphenyl]-2-naphthalenecarboxylic acid (CD437/AHPN) while initially determined to be a selective activator of the retinoic acid receptors (RARs) β and γ, has been found in numerous studies to inhibit cell growth and induce apoptosis in a variety of malignant cell types utilizing a RAR and retinoid X receptor (RXR)-independent mechanism. In addition, 4-[3-(1-adamantyl)-4-hydroxyphenyl]-3-chlorocinnamic acid (3-Cl-AHPC) which binds to the RARs but does not activate the RARs or RXRs is a potent inducer of apoptosis of AML cells in vitro. Recent reports suggest that the novel nuclear receptor, the small nuclear heterodimer partner (SHP, NR0B2), is involved in the induction of apoptosis by the ARRs.

Despite the reports cited above there is currently a need for additional chemical agents that are useful for inducing apoptosis and/or for treating cancer and in particular for treating leukemias. There is also a need for apoptosis inducers and anticancer agents that have enhanced activity or that have improved pharmacologic properties such as increased solubility or better bioavailability. There is also a need for apoptosis inducers and/or anticancer agents that are less toxic or that have an enhanced therapeutic window.

SUMMARY OF THE INVENTION

The present invention provides compounds that act as inducers of apoptosis and/or caspase activators and/or anti-cancer agents. In addition, representative compounds of the invention display increased solubility relative to reported compounds. Accordingly, there is provided a compound of the invention which is a compound of formula I:

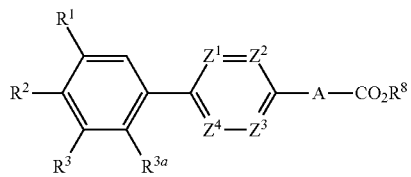

wherein:

$Z^1$ is $CR^4$, $Z^2$ is $CR^5$, $Z^3$ is $CR^6$ and $Z^4$ is N; or $Z^1$ is N, $Z^2$ is $CR^5$, $Z^3$ is $CR^6$ and $Z^4$ is N; or $Z^1$ is $CR^4$, $Z^2$ is N, $Z^3$ is $CR^6$ and $Z^4$ is N; or $Z^1$ is $CR^4$, $Z^2$ is $CR^5$, $Z^3$ is N and $Z^4$ is N; or $Z^1$ is $CR^4$, $Z^2$ is N, $Z^3$ is $CR^6$ and $Z^4$ is $CR^7$; or $Z^1$ is $CR^4$, $Z^2$ is N, $Z^3$ is N and $Z^4$ is $CR^7$;

$R^1$ is adamantyl, nor-adamantyl, bicyclooctyl or ($C_2$-$C_{10}$)alkynyl, wherein any adamantyl, nor-adamantyl, bicyclooctyl or ($C_2$-$C_{10}$)alkynyl of $R^1$ may be optionally substituted with one or more groups (e.g. 1, 2 or 3) selected from —OH, oxo(=O), =$CH_2$ and —$NH_2$;

$R^2$ is —OH, —OC(=O)$R_a$, —OC(=O)$NR_bR_c$, or —OC(=O)O$R_a$, and $R^3$ is H, halo, —CN, —$NO_2$, ($C_1$-$C_6$)alkyl, —OH, ($C_1$-$C_3$)alkoxy, —$NR_dR_e$, —$CO_2R_f$, —C(=O)$R_f$, —$NR_f$C(=O)$R_g$, —C(=O)$NR_dR_e$, wherein any alkyl or alkoxy of $R^3$ may be optionally substituted with one or more (e.g. 1, 2, 3, 4 or 5) groups selected from halo, oxo, hydroxy, —$NR_{z1}R_{z2}$ and ($C_1$-$C_3$)alkoxy; or $R^2$ and $R^3$ together with the atoms to which they are attached form an alkyenedioxy ring, wherein alkylenedioxy ring is optionally substituted with one or more (e.g. 1, 2 or 3) ($C_1$-$C_6$)alkyl;

$R^{3a}$ is H, halo, —OH, —($C_1$-$C_6$)alkyl or ($C_1$-$C_3$)alkoxy;

A is —$CR_h$=$CR_h$— or —$NR_iCR_jR_k$—;

$R^4$ is H, halo, —CN, —$NO_2$, —$N_3$, —OH, ($C_1$-$C_{10}$)alkyl, ($C_1$-$C_{10}$)alkoxy, —$NR_mR_n$, —$NR_o$(C=O)$R_p$ or —$CO_2R_o$, wherein any alkyl or alkoxy of $R^4$ may be optionally substituted with one or more (e.g. 1, 2, 3, 4 or 5) groups selected from halo, oxo, hydroxy, —CN, —$NR_{z1}R_{z2}$, —C(=O)$NR_{z1}R_{z2}$ and ($C_1$-$C_3$)alkoxy;

$R^5$ is H or F;

$R^6$ is H or F;

$R^7$ is H, halo, —CN, —$NO_2$, —$N_3$, —OH, ($C_1$-$C_{10}$)alkyl, ($C_1$-$C_{10}$)alkoxy, —$NR_mR_n$, —$NR_o$(C=O)$R_p$ or —$CO_2R_o$, wherein any alkyl or alkoxy of $R^4$ may be optionally substituted with one or more (e.g. 1, 2, 3, 4 or 5) groups selected from halo, oxo, hydroxy, —CN, —C(=O)$NR_{z1}R_{z2}$ and ($C_1$-$C_3$)alkoxy;

$R^8$ is H, ($C_1$-$C_6$)alkyl, aryl($C_1$-$C_6$)alkyl or aryl;

each $R_a$ is independently $(C_1-C_6)$alkyl, aryl$(C_1-C_6)$alkyl or aryl;

$R_b$ and $R_c$ are each independently selected from H or $(C_1-C_6)$alkyl; or $R_b$ and $R_c$, together with the nitrogen to which they are attached form a pyrrolidino, piperidino, piperazino, azetidino, morpholino, or thiomorpholino;

$R_d$ and $R_e$ are each independently H or $(C_1-C_6)$alkyl; or $R_d$ and $R_e$ together with the nitrogen to which they are attached form a pyrrolidino, piperidino, piperazino, azetidino, morpholino, or thiomorpholino;

each $R_f$ is independently H, $(C_1-C_6)$alkyl, aryl$(C_1-C_6)$alkyl or aryl;

each $R_g$ is independently $(C_1-C_6)$alkyl, aryl$(C_1-C_6)$alkyl or aryl;

each $R_h$ is independently H or F;

each $R_i$ is independently H or $(C_1-C_6)$alkyl;

$R_j$ and $R_k$ are each independently H or $(C_1-C_6)$alkyl $R_m$ and $R_n$ are each independently H or $(C_1-C_6)$alkyl; or $R_m$ and $R_n$ together with the nitrogen to which they are attached form a pyrrolidino, piperidino, piperazino, azetidino, morpholino, or thiomorpholino;

each $R_o$ is independently H, $(C_1-C_6)$alkyl, aryl$(C_1-C_6)$alkyl or aryl;

each $R_p$ is independently $(C_1-C_6)$alkyl, aryl$(C_1-C_6)$alkyl or aryl; and $R_{z1}$ and $R_{z2}$ are each independently selected from H or $(C_1-C_6)$alkyl; or $R_{z1}$ and $R_{z2}$ together with the nitrogen to which they are attached form a pyrrolidino, piperidino, piperazino, azetidino, morpholino, or thiomorpholino;

or a salt thereof.

The invention also provides a pharmaceutical composition comprising a compound of formula I, or a pharmaceutically acceptable salt thereof, and a pharmaceutically acceptable diluent or carrier.

The invention also provides a method for inducing cell death or apoptosis in a cell comprising contacting the cell in vitro or in vivo with an effective amount of a compound of formula I, or a salt thereof.

The invention also provides a method for inducing apoptosis or cell death in a mammal (e.g. a human) in need of such treatment comprising administering to the mammal an effective amount of a compound of formula I, or a pharmaceutically acceptable salt thereof.

The invention also provides a method for activating one or more caspase (e.g. caspase 3 or caspase 9) in a cell comprising contacting the cell in vitro or in vivo with an effective amount of a compound of formula I, or a salt thereof.

The invention also provides a method for activating one or more caspase (e.g. caspase 3 or caspase 9) in a mammal (e.g. a human) in need of such treatment comprising administering to the mammal an effective amount of a compound of formula I, or a pharmaceutically acceptable salt thereof.

The invention also provides a method for inhibiting cancer (e.g. lung cancer, breast cancer, colorectal cancer, hepatic cancer, ovarian cancer, pancreatic cancer, prostate cancer, or leukemia including acute lymphocytic leukemia, acute myelogenous leukemia or chronic myelogenous leukemia) cell growth comprising contacting the cancer cell in vitro or in vivo with an effective amount of a compound of formula I, or a salt thereof.

The invention also provides a method for treating cancer (e.g. lung cancer, breast cancer, colorectal cancer, hepatic cancer, ovarian cancer, pancreatic cancer, prostate cancer, or leukemia (e.g. acute lymphocytic leukemia, acute myelogenous leukemia or chronic myelogenous leukemia) in a mammal (e.g. a human) comprising administering to the mammal an effective amount of a compound of formula I or a pharmaceutically acceptable salt thereof.

The invention also provides a method for modulating SHP or inducing cell death or apoptosis in a pancreatic cancer stem cell comprising contacting the cell in vitro or in vivo with an effective amount of a compound of formula I, or a salt thereof.

The invention also provides a method for modulating SHP or inducing cell death or apoptosis in a pancreatic cancer stem cell in a mammal (e.g. a human) in need of such treatment comprising administering to the mammal an effective amount of a compound of formula I, or a pharmaceutically acceptable salt thereof.

The invention also provides a compound of formula I or a pharmaceutically acceptable salt thereof, for use in medical therapy (e.g. for use in inducing apoptosis, inducing cell death, activating one or more caspase such as caspase 3 or caspase 9 or treating cancer such as lung cancer, breast cancer, colorectal cancer, hepatic cancer, ovarian cancer, pancreatic cancer, prostate cancer, or leukemia including acute lymphocytic leukemia, acute myelogenous leukemia or chronic myelogenous leukemia).

The invention also provides the use of a compound of formula I or a pharmaceutically acceptable salt thereof, for the manufacture of a medicament useful for inducing apoptosis, inducing cell death, activating one or more caspase (e.g. caspase 3 or caspase 9) or for the treatment of cancer (e.g. lung cancer, breast cancer, colorectal cancer, hepatic cancer, ovarian cancer, pancreatic cancer, prostate cancer, or leukemia including acute lymphocytic leukemia, acute myelogenous leukemia or chronic myelogenous leukemia) in a mammal (e.g. a human).

The invention also provides the use of a compound of formula I or a pharmaceutically acceptable salt thereof, for the manufacture of a medicament useful for modulating SHP or inducing cell death or apoptosis in a pancreatic cancer stem cell in a mammal (e.g. a human).

The invention also provides a compound of formula I, or a pharmaceutically acceptable salt thereof, for use in the prophylactic or therapeutic treatment of cancer (e.g. lung cancer, breast cancer, colorectal cancer, hepatic cancer, ovarian cancer, pancreatic cancer, or leukemia including acute lymphocytic leukemia, acute myelogenous leukemia or chronic myelogenous leukemia) in a mammal (e.g. a human).

The invention also provides processes and novel intermediates disclosed herein that are useful for preparing compounds of formula I or salts thereof. Some of the compounds of formula I are useful to prepare other compounds of formula I.

DETAILED DESCRIPTION

Figure 1:
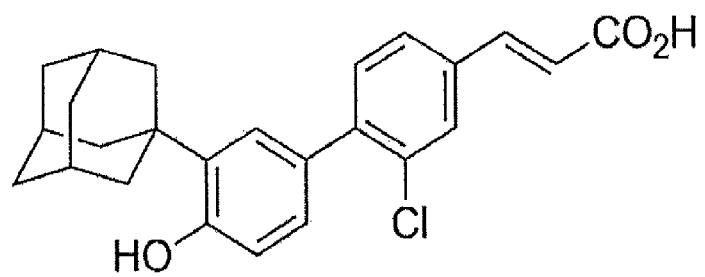
FIG. 1 illustrates the structure of 3-Cl-AHPC and compound 16.
Figure 1:
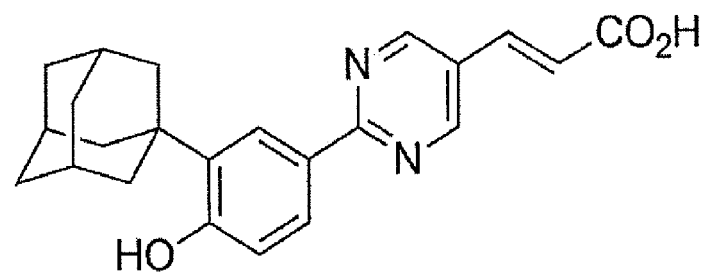

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to.

Aryl denotes a phenyl radical or an ortho-fused bicyclic carbocyclic radical having about nine to ten ring atoms in which at least one ring is aromatic. Examples of aryl include phenyl, indenyl, and naphthyl.

Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$)alkyl, phenyl or benzyl. Heteroaryl also includes a radical of an ortho-fused bicyclic of about eight to ten ring atoms comprising one to four heteroatoms each selected from the group consisting of non-peroxide oxygen, sulfur, and N(X) provided at least one of the rings of the bicyclic is aromatic and provided that the aromatic ring is comprised of at least one heteroatom. Examples of heteroaryl include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, thienyl, pyrimidinyl, indolyl, isoquinolyl, tetrahydroisoquinoline, benzofuran, benzimidazole, tetrahyroquinolyl, and quinolyl.

The term "alkylenedioxy ring" refers to a ring fused to two adjacent carbon atoms of an aryl group (e.g phenyl) so that the ring is either 5 or 6 atoms and wherein the ring has two oxygen atoms. The two oxygen atoms of the alkylenedioxy ring are each connected to the adjacent carbon atoms of the aryl group and the two oxygen atoms are separated from one another by an methyl or ethyl group.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

Specific values listed below for radicals, substituents, and ranges, are for illustration only; they do not exclude other defined values or other values within defined ranges for the radicals and substituents. The specific values listed below are specific values for compounds of formula I as well as compounds of formula IIa, IIb, IIc, IId, IIe and IIf.

A specific group of compounds of formula I are compounds of formula IIa:

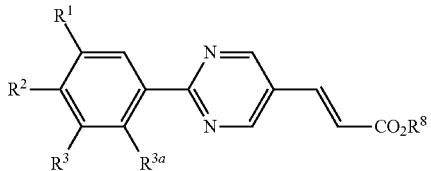

or a salt thereof.

A specific group of compounds of formula I are compounds of formula IIb:

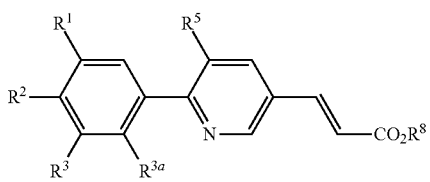

or a salt thereof.

A specific group of compounds of formula I are compounds of formula IIc:

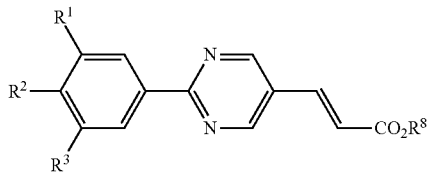

or a salt thereof.

A specific group of compounds of formula I are compounds of formula IId:

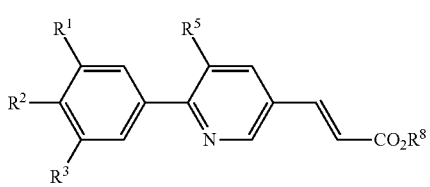

or a salt thereof.

A specific group of compounds of formula I are compounds of formula IIe:

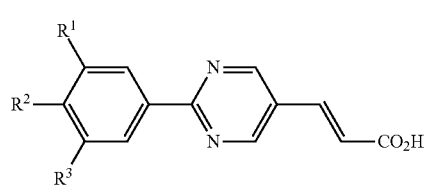

or a salt thereof.

A specific group of compounds of formula I are compounds of formula IIf:

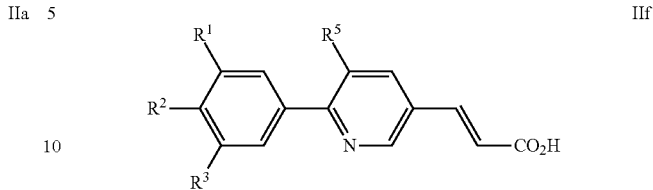

or a salt thereof.

Specifically, $(C_1\text{-}C_6)$alkyl can be methyl, ethyl, propyl, isopropyl, butyl, iso-butyl, sec-butyl, pentyl, 3-pentyl, or hexyl; $(C_1\text{-}C_{10})$alkyl can be methyl, ethyl, propyl, isopropyl, butyl, iso-butyl, sec-butyl, pentyl, 3-pentyl, hexyl, heptyl, octyl, nonyl, or decyl; $(C_3\text{-}C_6)$cycloalkyl can be cyclopropyl, cyclobutyl, cyclopentyl, or cyclohexyl; $(C_1\text{-}C_6)$alkoxy can be methoxy, ethoxy, propoxy, isopropoxy, butoxy, iso-butoxy, sec-butoxy, pentoxy, 3-pentoxy, or hexyloxy; $(C_2\text{-}C_{10})$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 1-octynyl, or 1-nonyl.

A specific group of compounds of formula I are compounds of formula I:

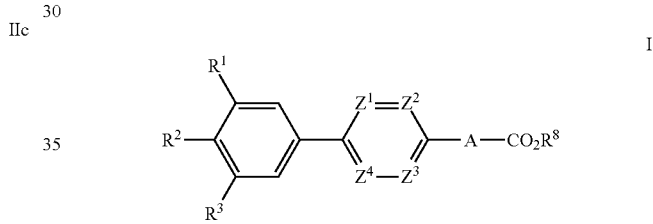

wherein:
$Z^1$ is $CR^4$, $Z^2$ is $CR^5$, $Z^3$ is $CR^6$ and $Z^4$ is N; or $Z^1$ is N, $Z^2$ is $CR^5$, $Z^3$ is $CR^6$ and $Z^4$ is N; or $Z^1$ is $CR^4$, $Z^2$ is N, $Z^3$ is $CR^6$ and $Z^4$ is N; or $Z^1$ is $CR^4$, $Z^2$ is $CR^5$, $Z^3$ is N and $Z^4$ is N; or $Z^1$ is $CR^4$, $Z^2$ is N, $Z^3$ is $CR^6$ and $Z^4$ is $CR^7$; or $Z^1$ is $CR^4$, $Z^2$ is N, $Z^3$ is N and $Z^4$ is $CR^7$;

$R^1$ is adamantyl, nor-adamantyl, bicyclooctyl or $(C_2\text{-}C_{10})$alkynyl;

$R^2$ is —OH, —OC(=O)$R_a$, —OC(=O)N$R_bR_c$ or, —OC(=O)O$R_a$;

$R^3$ is H, halo, —CN, —NO$_2$, $(C_1\text{-}C_6)$alkyl, —OH, $(C_1\text{-}C_3)$alkoxy, —N$R_dR_e$, —CO$_2R_f$, —C(=O)$R_f$, —NR$_f$(C=O)$R_g$, —C(=O)N$R_dR_e$, wherein any alkyl or alkoxy of $R^3$ may be optionally substituted with one or more (e.g. 1, 2, 3, 4 or 5) groups selected from halo, oxo, hydroxy, —N$R_{z1}R_{z2}$ and $(C_1\text{-}C_3)$alkoxy;

A is —CR$_h$=CR$_h$— or —NR$_i$CR$_jR_k$—;

$R^4$ is H, halo, —CN, —NO$_2$, —N$_3$, —OH, $(C_1\text{-}C_{10})$alkyl, $(C_1\text{-}C_{10})$alkoxy, —N$R_mR_n$, —N$R_o$(C=O)$R_p$ or —CO$_2R_o$, wherein any alkyl or alkoxy of $R^4$ may be optionally substituted with one or more (e.g. 1, 2, 3, 4 or 5) groups selected from halo, oxo, hydroxy, —CN, —N$R_{z1}R_{z2}$, —C(=O)N$R_{z1}R_{z2}$ and $(C_1\text{-}C_3)$alkoxy;

$R^5$ is H or F;

$R^6$ is H or F;

$R^7$ is H, halo, —CN, —NO$_2$, —N$_3$, —OH, $(C_1\text{-}C_{10})$alkyl, $(C_1\text{-}C_{10})$alkoxy, —N$R_mR_n$, —N$R_o$(C=O)$R_p$ or —CO$_2R_o$, wherein any alkyl or alkoxy of $R^4$ may be optionally substituted with one or more (e.g. 1, 2, 3, 4 or 5) groups selected from halo, oxo, hydroxy, —CN, —NR$_{z1}$R$_{z2}$, —C(=O)NR$_{z1}$R$_{z2}$ and (C$_1$-C$_3$)alkoxy;

R$^8$ is H, (C$_1$-C$_6$)alkyl, aryl(C$_1$-C$_6$)alkyl or aryl;

each R$_a$ is independently (C$_1$-C$_6$)alkyl, aryl(C$_1$-C$_6$)alkyl or aryl;

R$_b$ and R$_c$ are each independently selected from H or (C$_1$-C$_6$)alkyl; or R$_b$ and R$_c$ together with the nitrogen to which they are attached form a pyrrolidino, piperidino, piperazino, azetidino, morpholino, or thiomorpholino;

R$_d$ and R$_e$ are each independently H or (C$_1$-C$_6$)alkyl; or R$_d$ and R$_e$ together with the nitrogen to which they are attached form a pyrrolidino, piperidino, piperazino, azetidino, morpholino, or thiomorpholino;

each R$_f$ is independently H, (C$_1$-C$_6$)alkyl, aryl(C$_1$-C$_6$)alkyl or aryl;

each R$_g$ is independently (C$_1$-C$_6$)alkyl, aryl(C$_1$-C$_6$)alkyl or aryl;

each R$_h$ is independently H or F;

each R$_i$ is independently H or (C$_1$-C$_6$)alkyl;

R$_j$ and R$_k$ are each independently H or (C$_1$-C$_6$)alkyl

R$_m$ and R$_n$ are each independently H or (C$_1$-C$_6$)alkyl; or R$_m$ and R$_n$ together with the nitrogen to which they are attached form a pyrrolidino, piperidino, piperazino, azetidino, morpholino, or thiomorpholino;

each R$_o$ is independently H, (C$_1$-C$_6$)alkyl, aryl(C$_1$-C$_6$)alkyl or aryl;

each R$_p$ is independently (C$_1$-C$_6$)alkyl, aryl(C$_1$-C$_6$)alkyl or aryl; and R$_{z1}$ and R$_{z2}$ are each independently selected from H or (C$_1$-C$_6$)alkyl; or R$_{z1}$ and R$_{z2}$ together with the nitrogen to which they are attached form a pyrrolidino, piperidino, piperazino, azetidino, morpholino, or thiomorpholino;

or a salt thereof

A specific group of compounds of formula I are compounds wherein Z$^1$ is CR$^4$, Z$^2$ is CR$^5$, Z$^3$ is CR$^6$ and Z$^4$ is N.

Another specific group of compounds of formula I are compounds wherein Z$^1$ is N, Z$^2$ is CR$^5$, Z$^3$ is CR$^6$ and Z$^4$ is N.

Another specific group of compounds of formula I are compounds wherein Z$^1$ is CR$^4$, Z$^2$ is N, Z$^3$ is CR$^6$ and Z$^4$ is N.

Another specific group of compounds of formula I are compounds wherein Z$^1$ is CR$^4$, Z$^2$ is CR$^5$, Z$^3$ is N and Z$^4$ is N.

Another specific group of compounds of formula I are compounds wherein Z$^1$ is CR$^4$, Z$^2$ is N, Z$^3$ is CR$^6$ and Z$^4$ is CR$^7$.

Another specific group of compounds of formula I are compounds wherein Z$^1$ is CR$^4$, Z$^2$ is N, Z$^3$ is N and Z$^4$ is CR$^7$.

Another specific group of compounds of formula I are compounds wherein R$^5$ and R$^6$ are H.

A specific value for R$^5$ is H.

A specific value for R$^6$ is H.

A specific value for R$^4$ is H or halo.

Another specific value for R$^4$ is Cl.

Another specific value for R$^4$ is H.

A specific value for R$^7$ is H or halo.

Another specific value for R$^7$ is H.

A specific value for R$^1$ is adamantyl, cyclooctyl or nor-adamantyl.

Another specific value for R$^1$ is adamantyl, wherein any adamantyl of R$^1$ may be optionally substituted with one or more groups selected from —OH and oxo(=O).

Another specific value for R$^1$ is:

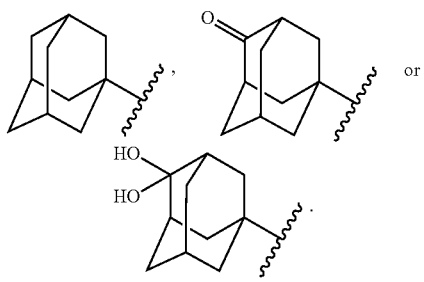

Another specific value for R$^1$ is adamantyl.

A specific value for R$^2$ is —OH.

Another specific value for R$^2$ is —OC(=O)R$_a$.

A specific value for R$_a$ is (C$_1$-C$_6$)alkyl.

Another specific value for R$_a$ is CH$_3$.

A specific value for R$^3$ is H.

Another specific value for R$^3$ is H or (C$_1$-C$_3$)alkoxy.

A specific value for R$^{3a}$ is H, —(C$_1$-C$_6$)alkyl or (C$_1$-C$_3$)alkoxy.

Another specific value for R$^{3a}$ is H.

A specific group of compounds of formula I are compounds wherein R$^2$ and R$^3$ together with the atoms to which they are attached form a alkylenedioxy ring, wherein the alkylenedioxy ring is optionally substituted with one or more (C$_1$-C$_6$)alkyl.

Another specific group of compounds of formula I are compounds wherein R$^2$ and R$^3$ together with the atoms to which they are attached form a methylenedioxy ring.

A specific value for A is —CR$_h$=CR$_h$—.

A specific value for R$_h$ is H.

A specific value for R$^8$ is H or (C$_1$-C$_6$)alkyl.

Another specific value for R$^8$ is H.

A specific compound of the invention is the compound

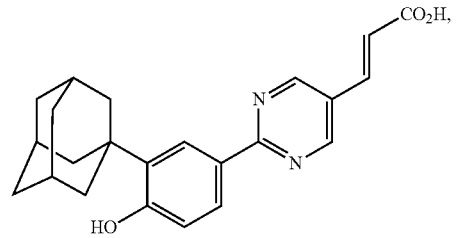

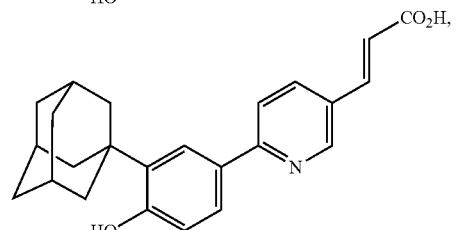

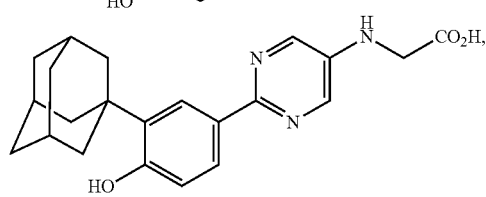

-continued
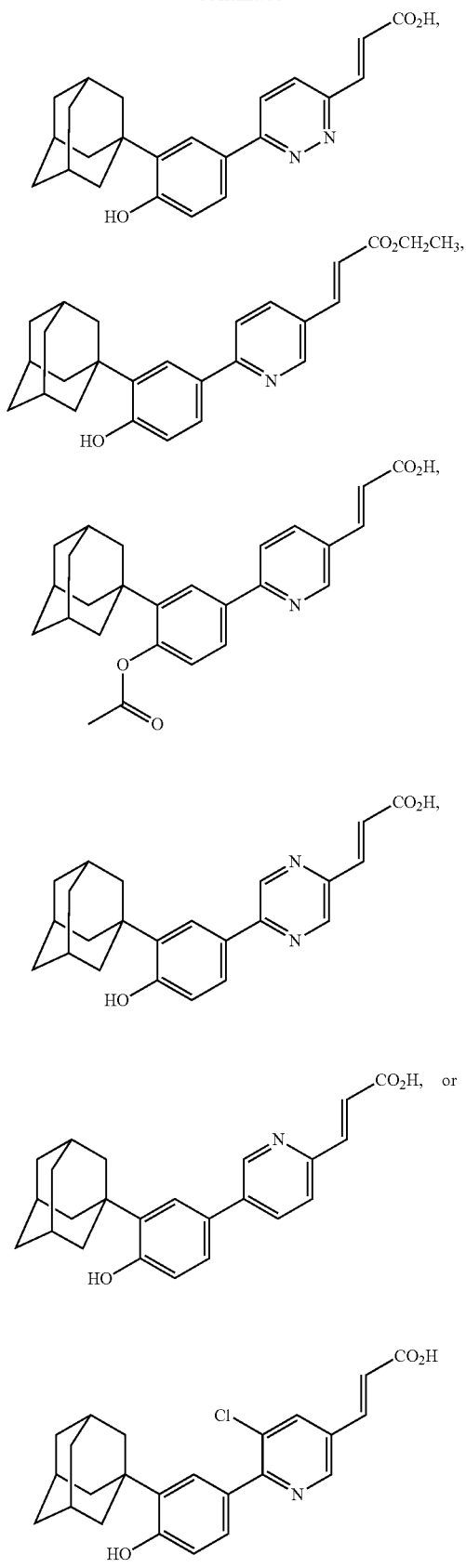
or a salt thereof.
Another specific compound of the invention is the compound
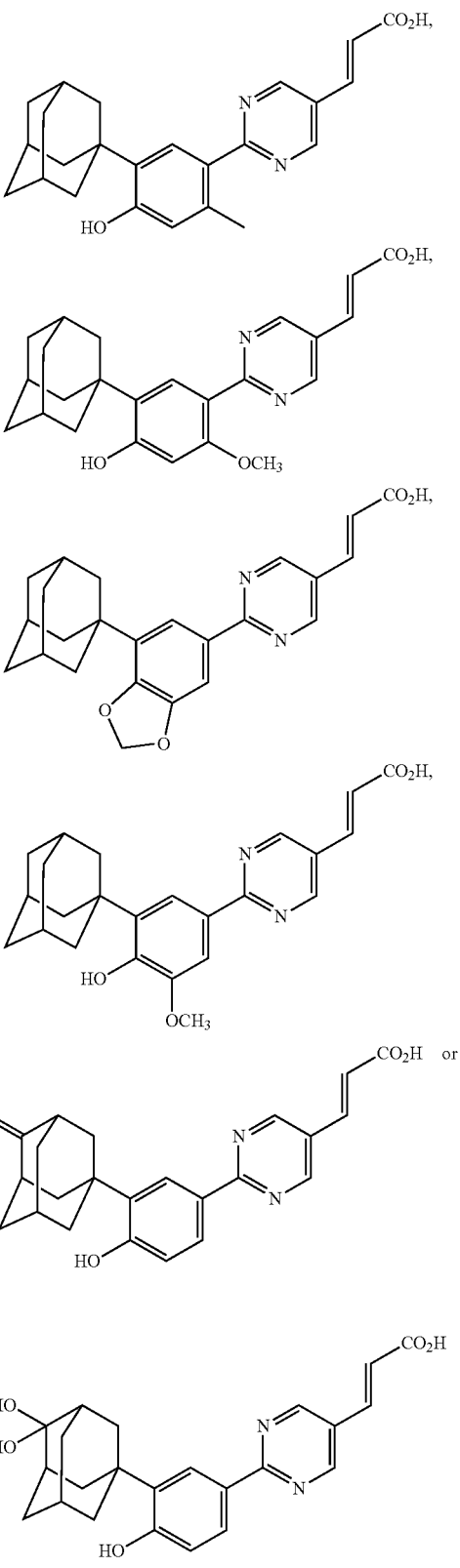
or a salt thereof.

A specific compound of the invention is the compound
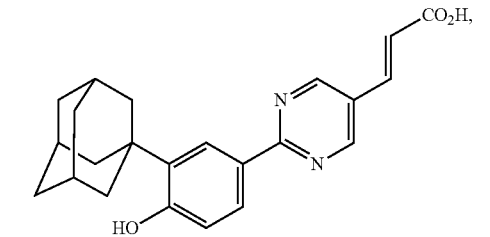
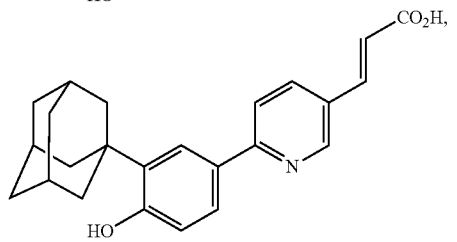
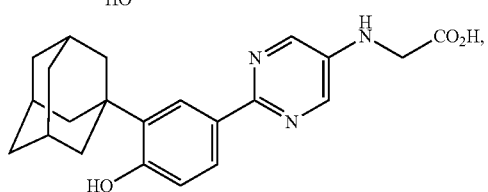
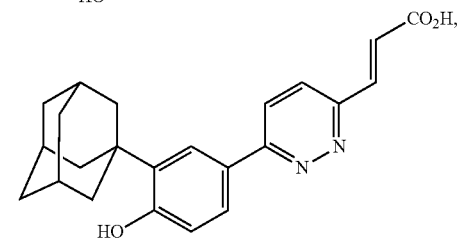
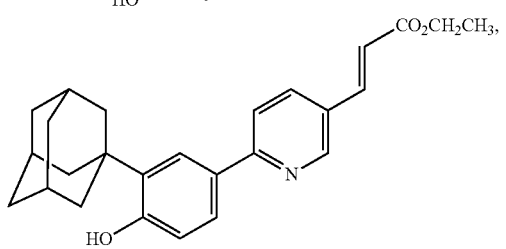
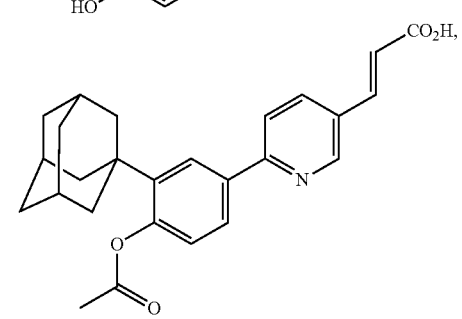
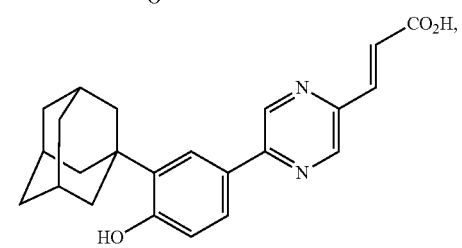
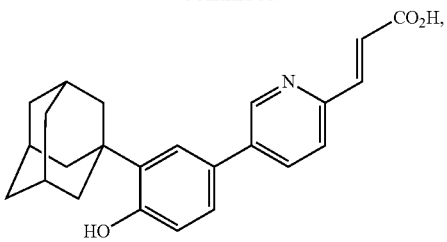
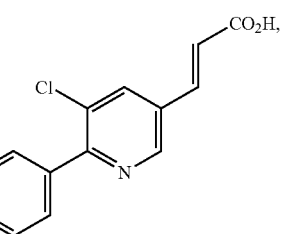
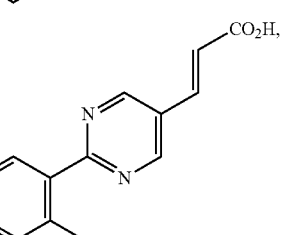
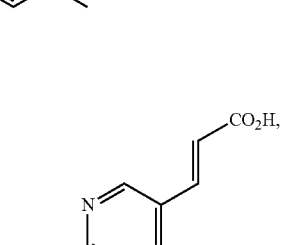
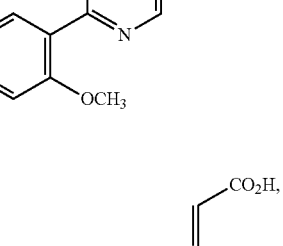
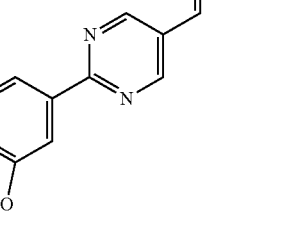
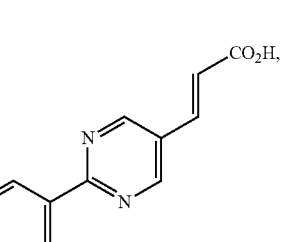

-continued

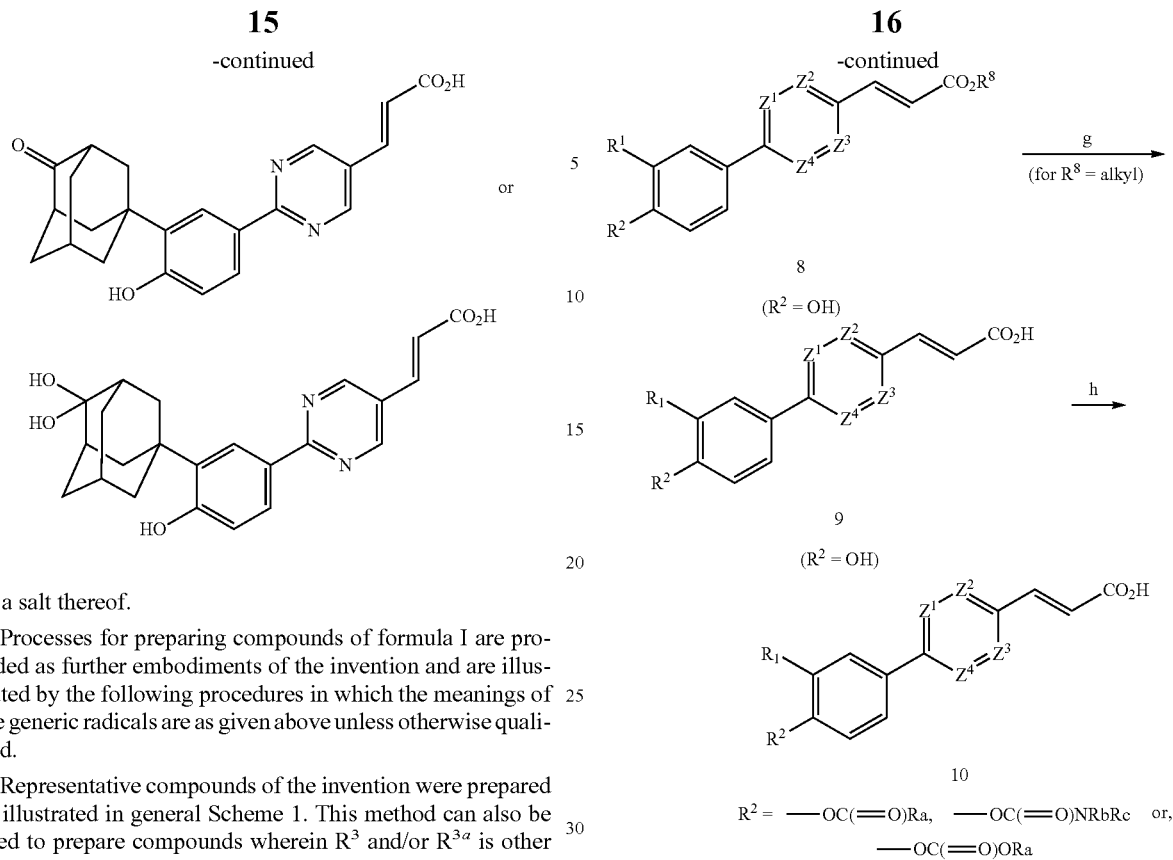

or a salt thereof.

Processes for preparing compounds of formula I are provided as further embodiments of the invention and are illustrated by the following procedures in which the meanings of the generic radicals are as given above unless otherwise qualified.

Representative compounds of the invention were prepared as illustrated in general Scheme 1. This method can also be used to prepare compounds wherein $R^3$ and/or $R^{3a}$ is other than hydrogen.

Scheme 1. Methods used to prepare compounds of the invention.

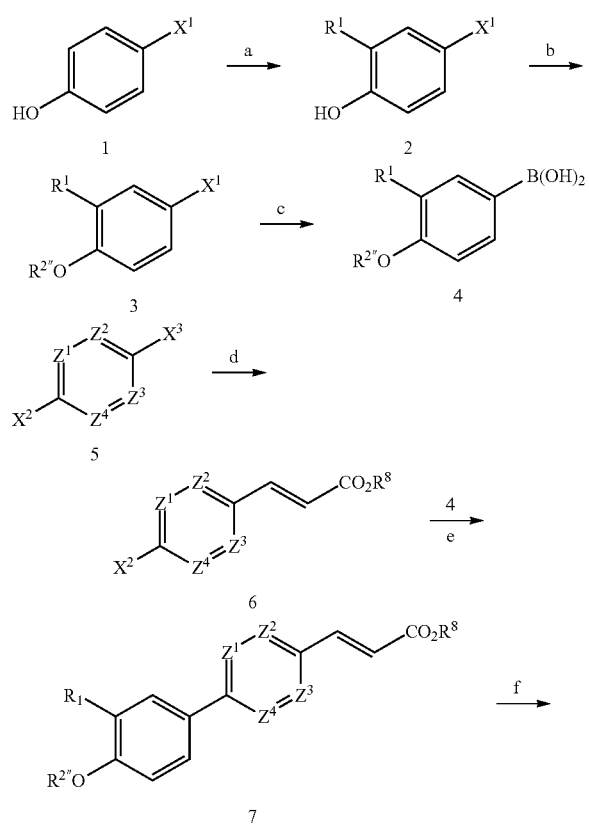

$R^{2''}$ = Bn, Me, TBDMS, TMS, or MOM
$X^1$ = Cl, Br, or I
$X^2$ = Cl, Br, I, or TfO
$X^3$ = I, Br, Cl, or CHO
(a) $R^1$OH, $CH_3SO_3H$ or $H_2SO_4$, $CH_2Cl_2$, heat.
(b) $R^{2''}$Cl or $R^{2''}$Br, $K_2CO_3$, acetone, heat.
(c) n-BuLi, THF, low temperature; (MeO)$_3$B or (i-PrO)$_3$B; $H_3O^+$.
(d) $X_3$ = I, Br, or Cl: $H_2C$=$CHCO_2R^8$, DMF, (i-Pr)$_2$EtN, (2-MePh)$_3$P, heat; or
$X_3$ = CHO: ($R^8O_2CCH$)(Ph)$_3$P, MePh, heat; or
$X_3$ = CHO: [(EtO)$_2$P(O)CH$_2$CO$_2$R$^8$, NaH, THF].
(e) 4, Pd(PPh$_3$)$_4$, aq. Na$_2$CO$_3$, DME, heat.
(f) BBr$_3$, CH$_2$Cl$_2$, low temperature; H$_2$O.
(g) aq. NaOH, MeOH, heat; $H_3O^+$; or LiOH·H$_2$O, THF/MeOH/H$_2$O; $H_3O^+$.
(h) (R$_a$CO)$_2$O or R$_a$COCl or R$_b$R$_c$NC(=O)Cl, 4-(Me$_2$N)-pyridine, THF.

Additional compounds of the invention can be prepared by the following the steps outlined in Scheme 1. For example, by utilizing a substituted phenol of 1 (e.g. a phenol of formula 1a), compounds wherein $R^3$ is other than hydrogen may be prepared.

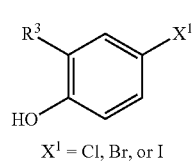

$X^1$ = Cl, Br, or I

A compound of formula I wherein $R^8$ is H can be prepared by saponifying the corresponding ester 11 to provide a compound of formula I wherein $R^8$ is H. A compound of formula I wherein $R^2$ is —OC(=O)CH$_3$ can be prepared by acylating a corresponding phenol 12 to provide a compound of formula I wherein $R^2$ is —OC(=O)CH$_3$. This method can also be used to prepare compounds wherein $R^3$ and/or $R^{3a}$ is other than hydrogen.

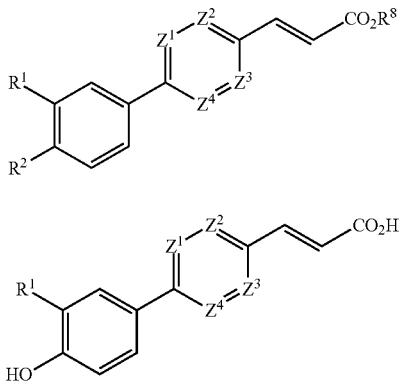

Intermediates useful for preparing a compound of formula I include compounds of formula 13, 14, 15, 14a and 15a.

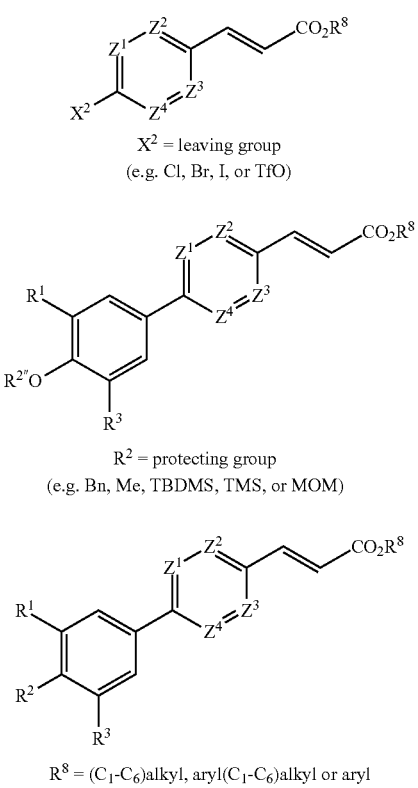

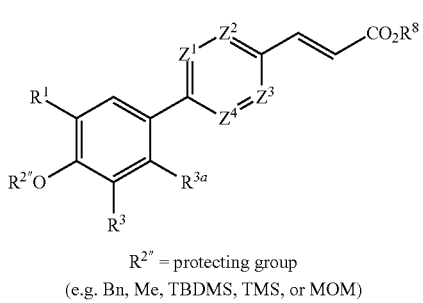

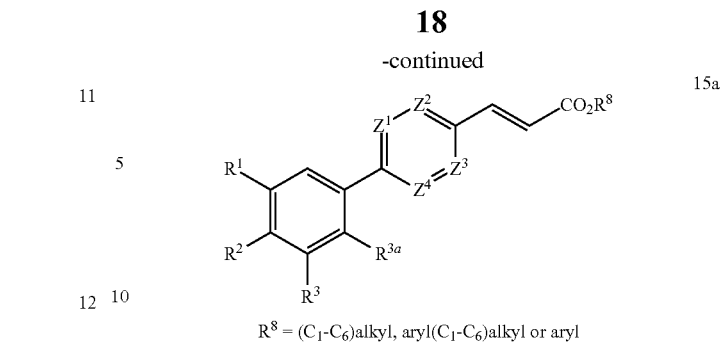

$R^8$ = ($C_1$-$C_6$)alkyl, aryl($C_1$-$C_6$)alkyl or aryl

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Salts, including pharmaceutically acceptable salts, may be obtained using standard procedures well known in the art, for example by reacting a sufficiently basic compound such as an amine with a suitable acid affording an anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 70 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful for the treatment of cancer. Such agents include but are not limited to alkylating agents, antimetabolites, anti-tumor antibiotics, topoisomerase inhibitors, mitotic inhibitors, corticosteroids, anti-angiogenic agents, plant alkaloids and hormonal agents. Examples include but are not limited to Erlotinib (TARCEVA®, Genentech/OSI Pharm.), Bortezomib (VELCADE®, Millennium Pharm.), Fulvestrant (FASLODEX®, AstraZeneca), Sunitinib (SUTENT®, Pfizer), Letrozole (FEMARA®, Novartis), Imatinib mesylate (GLEEVEC®, Novartis), Oxaliplatin (Eloxatin®, Sanofi), 5-FU (5-fluorouracil), Rapamycin (Sirolimus, RAPAMUNE®, Wyeth), Lapatinib (TYKERB®, GSK572016, Glaxo Smith Kline), Sorafenib (NEXAVAR®, Bayer), Irinotecan (CAMPTOSAR®, Pfizer), Gefitinib (IRESSA®, AstraZeneca), ADRIAMYCIN® (TAXOL® (paclitaxel; Bristol-Myers Squibb Oncology, Princeton, N.J.), TAXOTERE® (docetaxel), Rhône-Poulenc Rorer, Antony, France), GEMZAR® (gemcitabine), NAVELBINE® (vinorelbine); capecitabine (XELODA®), tamoxifen (including NOLVADEX®; tamoxifen citrate), FARESTON® (toremifine citrate), MEGASE® (megestrol acetate), AROMASIN (exemestane; Pfizer), RIVISOR® (vorozole), FEMARA® (letrozole; Novartis), and ARIMIDEX® (anastrozole; AstraZeneca); ALLOVECTIN®, LEUVECTIN®, VAXID®, PROLEUKIN®, LURTOTECAN®, ABARELIXO, bevacizumab (AVASTIN®, Genentech), cetuximab (ERBITUX®, Imclone), panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech) and gemtuzumab ozogamicin (MYLOTARG®, Wyeth).

Accordingly, in one embodiment the invention also provides a composition comprising a compound of formula I, or a pharmaceutically acceptable salt thereof, at least one other therapeutic agent, and a pharmaceutically acceptable diluent or carrier. The invention also provides a kit comprising a compound of formula I, or a pharmaceutically acceptable salt thereof, at least one other therapeutic agent, packaging material, and instructions for administering the compound of formula I or the pharmaceutically acceptable salt thereof and the other therapeutic agent or agents to a mammal.

General Biochemical and Pharmacological Materials and Methods.

Materials:

RPMI medium, fetal bovine serum (FBS) and Trizol reagent were purchased from Invitrogen (Grand Island, N.Y.). Anti-XIAP, anti-c-IAP and anti-SHP antibodies were from Santa Cruz Biotechnology (Santa Cruz, Calif.). Anti-procaspase-3 and active cleaved caspase-3 antibodies were from Cell Signaling (Bellerica, Mass.) and tubulin from Oncogene Research Products (Boston, Mass.), respectively.

Acute Myelogenous Leukemia Cells.

FFMA-AML cells were obtained from a patient with a diagnosis of AML as indicated by the immunophenotyping described in Table 1. This patient was refractory to the chemotherapy regimens consisting of cytosine arabinoside given with daunomycin as well as high-dose cytosine arabinoside. Peripheral blood samples were obtained from the patient utilizing a Wayne State University Institutional Review Board approved protocol and the leukemic blasts were isolated utilizing Ficoll hypaque. The isolated leukemic cells (representing >99% of the cells) were subsequently cultured in RPMI 1640 supplemented with 10% heat-inactivated fetal bovine serum (FBS) and growth factors interleukin 3 (IL-3), granulocyte-colony stimulating factor (G-CSF), granulocyte/macrophage colony-stimulating factor (GM-CSF), and stem cell factor (SCF) as we have previously reported, and then the cells were maintained in 10% FBS and gentamycin (Zhang Y. et al., Blood, 2003; 192:3743-3752). The TF(v-SRC) leukemia cells have been previously described (Black J. H. et al., Leukemia. 2003; 17:155-159). TF(v-SRC) cells were grown in RPMI 1640 supplemented with 10% heat inactivated FBS.

TABLE 1

Patient leukemia cell characteristics from which the FFMA-AML cell line was derived.

| MoAb/CD number | Positive (%) |
|---|---|
| CD45 | 98 |
| CD56 | 98 |
| CD9 | 97 |
| CD40 | 98 |
| CD13 | 96 |
| CD33 | 96 |
| CD41 | 95 |
| CD61 | 96 |
| CD117 | 96 |
| Karyotype: 46,XX,del(9)(q22q32)add(22)(q13)[20] | |

Apoptosis:

Apoptosis of cells was determined by (1) acridine orange and ethidium bromide-staining to assess cells with nuclear fragmentation and chromatin condensation as previously described (Farhana L. et al., Cancer Res. 2006; 65:4909-4917) and (2) flow cytometry assessing Annexin V-FITC binding together with propidium iodide staining (Annexin V-FITC apoptosis Detection kit 1, BD Biosciences, San Diego, Calif.). Data acquisition was done on a FACS Calibur flow cytometer (BD) and analyzed with CellQuest software.

In Vivo Studies:

Non-obese diabetic-severe combined immunodeficiency (NOD-SCID) and ICR-SCID mice were obtained from Jackson Laboratories (Bar Harbor, Me.) and Taconic Farms (Germantown, N.Y.), respectively. A) FFMA-AML and TF(v-SRC) systemic models: NOD-SCID and ICR-SCID mice (4 to 5 weeks old) were injected with either FFMA-AML or TF(v-SRC) cells intravenously. Treatment with either vehicle, 3-Cl-AHPC or compound 16 (the compound of Example 1) was instituted the following day. Once symptoms such as diarrhea, dehydration, weight loss, ascites, paralysis or general weakness became evident, mice were euthanized. B) TF(v-SRC) subcutaneous mouse model. ICR-SCID mice were trocared subcutaneously bilaterally with TF(v-SRC) tumor fragments. Animals with equal tumor weights determined as described previously (Zhang Y. et al., Blood. 2002; 100:2917-2925) were assigned to three experimental arms: 1) control (vehicle treated), 2) subcutaneously treated with compound 16, and 3) intravenously treated with compound 16. The percent increase in the host life-span (% ILS) of the FFMA-AML and TF(v-SRC) bearing mice was calculated by subtracting the median day of death of the 3-Cl-AHPC or compound 16-treated AML-bearing mice from the median day of death of the vehicle-treated AML bearing mice divided by the median day of death of the AML-bearing vehicle treated mice. In order to determine the efficacy of the 3-Cl-AHPC and compound 16, survival distribution of the 3-Cl-AHPC or compound 16-treated (T) or vehicle (C) groups were compared using the log-rank test. Survival was characterized as the duration of the animal's life span 24 h after the initiation of the xenograft until an observed event (euthanasia or death). A p-value of less than 5% (p<0.05) was considered statistically significant.

Western Blots and RT-PCR:

Western blots, RNA preparation and RT-PCR were performed as described previously (Farhana, L. et al., Molecular Cancer Therapeutics, 2009; 8:1625-1635).

shRNA SHP Knockdown:

shRNA SHP retroviral expression vectors were prepared as described previously (Farhana L. et al., Cancer Res 2007; 67:318-325). FFMA-AML and TF(vSRC) cell lines were transiently transfected with retroviral shRNA-SHP plasmids either for 48 or 72 h. SHP protein expression was assessed using Western blots after 72 h infection with shRNA SHP retroviral expression vector in the FFMA-AML and TF(vSRC) cells. Anti-SHP antibody was obtained from MBL International Corporation (Woburn Mass.) and Santa Cruz Biotechnology (Santa Cruz, Calif.). Effect of SHP knockdown on 3-Cl-AHPC and compound 16 induction of apoptosis in cells was assessed 48 h following infection with shRNA SHP expression vectors. Apoptosis was determined using an Annexin V-FITC apoptosis detection kit.

The ability of a compound of the invention to act as an inducer of apoptosis and inhibitor of acute myelogenous leukemia (AML) cell growth was determined using Test A described below.

Test A.
Inhibition of Cell Growth and Induction of Apoptosis in AML KG-1 Human Myeloid Cell Line.

Methods for measuring the inhibition of cell growth and induction of apotosis followed literature procedures (Dawson, M. I., et al., J. Med. Chem., 2007, 50, 2622-2639). Table I below shows the inhibition of cell growth and induction of apoptosis in AML KG-1 human myeloid cell line by representative compounds of the invention.

TABLE I

Growth Inhibition and Apoptosis Induction of AML KG-1 cell line

| Compound Structure and Number | Growth Inhibition (% control) | | Apoptosis Induction (% control) | | Trtmt time (h) |
|---|---|---|---|---|---|
| | 1.0 µM | 5.0 µM | 1.0 µM | 5.0 µM | |
| 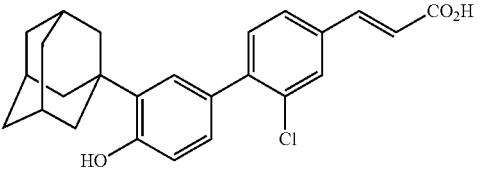 3-Cl-AHPC | 44 | 67 | 30 | 55 | 48 |
| 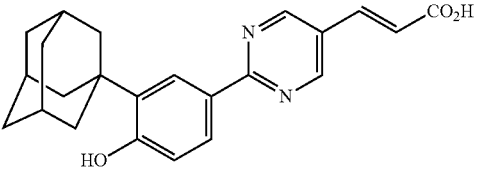 Compound 16 | 100 | 100 | 40 | 50 | 48 |
| 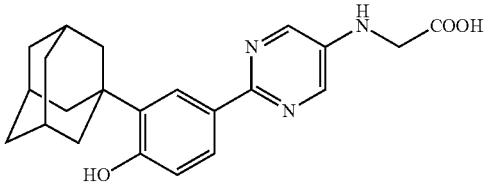 Compound 17 | 0 | 0 | 0 | 0 | 48 |
| 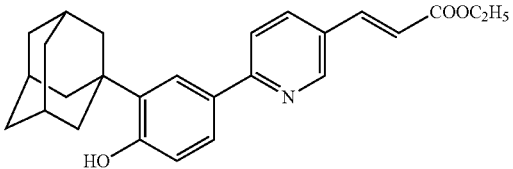 Compound 18 | 68<br>91 | 84<br>nd | 60<br>55 | 68<br>nd | 24<br>48 |
| 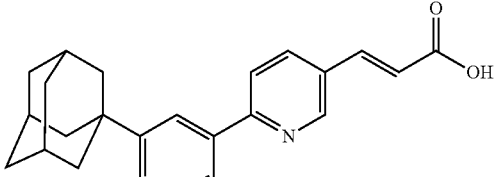 Compound 19 | 70 | 80 | 48 | 59 | 48 |

TABLE I-continued

Growth Inhibition and Apoptosis Induction of AML KG-1 cell line

| Compound Structure and Number | Growth Inhibition (% control) | | Apoptosis Induction (% control) | | Trtmt time (h) |
|---|---|---|---|---|---|
| | 1.0 µM | 5.0 µM | 1.0 µM | 5.0 µM | |
| Compound 20 | 0 | 45 | 0 | 0 | 48 |
| Compound 21 | 46 | 54 | 52 | 67 | 48 |
| Compound 22 | 41 | 47 | 55 | 65 | 48 |
| Compound 23 | 44 | 61 | 39 | 50 | 48 |
| Compound 24 | 48 | 58 | 36 | 52 | 48 | nd = not determined.

The ability of a compound of the invention to act as an inducer of apoptosis may be determined using Test B described below.

Test B.

Induction of Apoptosis of FFMA-AML and TF(v-SRC) Cells.

Figure 2:
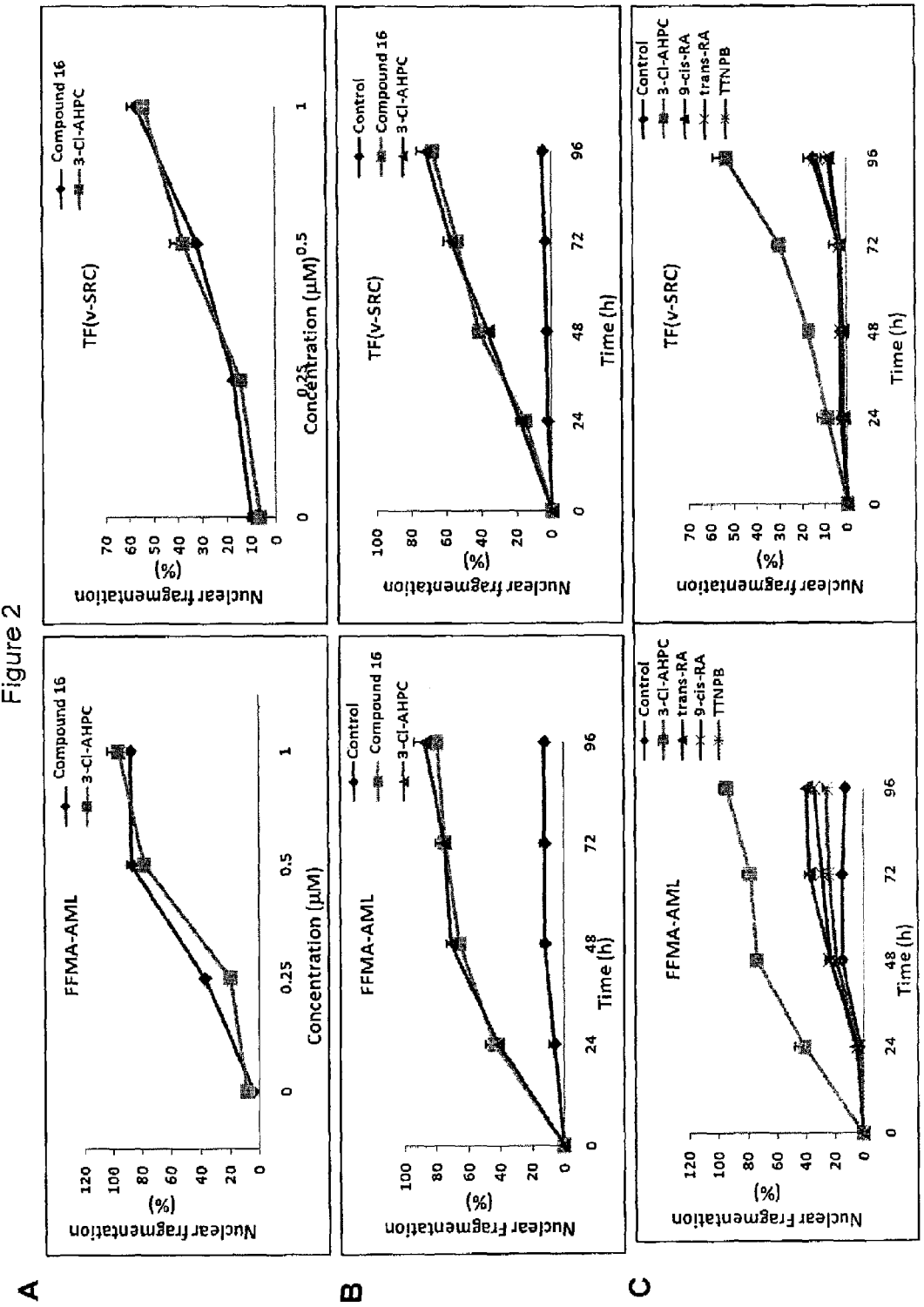
FIG. 2 illustrates apoptosis induction in FFMA-AML and TF(v-SRC) cells by 3-Cl-AHPC and compound 16. Cells were seeded at $1 \times 10^4$ cells/ml, grown for 24 h and then exposed to 1 μM compound 16 or 3-Cl-AHPC A) at various concentrations of the compound for 96 h and B) for increasing times of exposure. C) Induction of apoptosis by 3-Cl-AHPC, all-trans-retinoic acid, 9-cis-retinoic acid and TTNPB in FFMA-AML and TF(v-SRC) cells. The percentage of apoptotic cells was determined using acridine orange and ethidium bromide staining to determine nuclear fragmentation as described in the general biochemical and pharmacological materials and methods. The error bars represent the mean of three separate determinations +/– the standard deviation (SD).

The ability of 3-Cl-AHPC and compound 16 to induce apoptosis of FFMA-AML and TF(v-SRC) cells was examined by assessing the number of cells demonstrating nuclear fragmentation and chromatin condensation (FIGS. 2A and B). Cells were grown in the presence and absence of increasing concentrations of either 3-Cl-AHPC or compound 16 and for varying periods of time. There was a progressive increase in 3-Cl-AHPC- and compound 16-mediated apoptosis in both FFMA-AML and TF(v-SRC) cells with time and with increasing concentrations of the compounds. TF(v-SRC) cells displayed increased resistance compared to FFMA-AML cells to both 3-Cl-AHPC and compound 16 with an $ED_{50}$ of 0.75 µM when TF(v-SRC) cells were exposed to the compounds (FIGS. 2A and B). Under similar conditions, FFMA-AML cells displayed $ED_{50}$ values of 0.32 µM and 0.37 µM to compound 16 and 3-Cl-AHPC, respectively. Previous studies have demonstrated that acute promyelocytic leukemia (APL) cells undergo apoptosis in the presence of all-trans-retinoic acid (tRA), 9-cis-RA, and the RAR selective retinoid TTNPB through their ability to bind to the PML-RAR fusion protein (Weise K et al., Cell. 1994; 76: 345-354). We therefore tested the sensitivity of FFMA-AML and TF(v-SRC) cells to apoptosis induction by tRA, 9-cis RA, and TTNPB (FIG. 2C). The addition of either tRA, 9-cis-RA, or TTNPB to the FFMA-AML cells resulted in approximately 10% to 20% of the cells displaying apoptosis (over that noted with the vehicle), while the addition of 3-Cl-AHPC resulted in 80% of the cells displaying apoptosis (FIG. 2C). TF(v-SRC) cells were very resistant to the induction of apoptosis by those compounds (9-cis-RA, tRA or TTNPB) whose biological effects are mediated through the RARs and/or RXRs as no real increase in apoptosis was noted following exposure (FIG. 2C).

Figure 3:
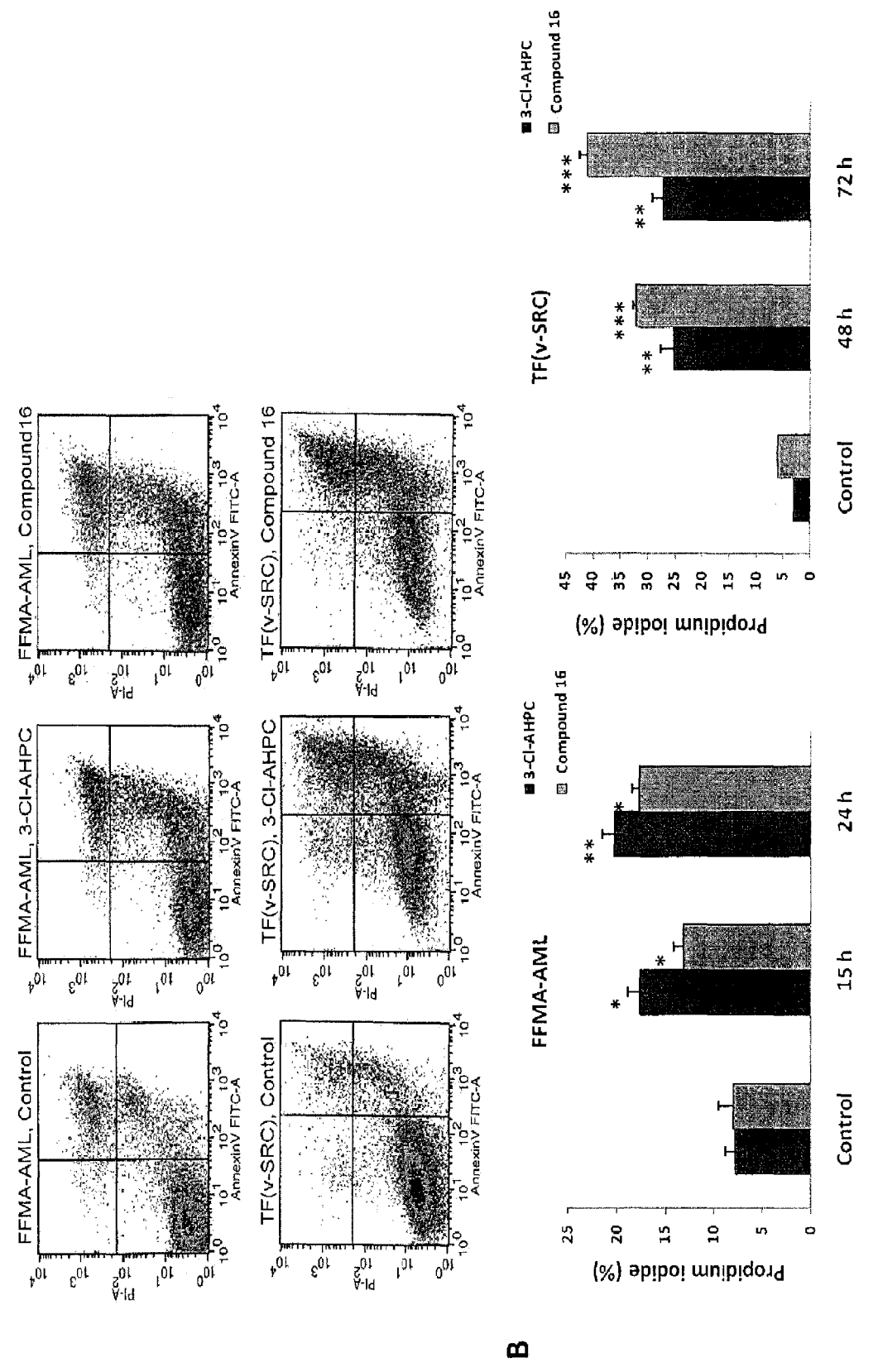
FIG. 3 illustrates the induction of apoptosis and cell death as assessed using Annexin V-FITC binding together with propidium iodide (PI) staining. FFMA-AML and TF(vSRC) cells were exposed to 1 μM 3-Cl-AHPC or compound 16. A) Apoptosis in FFMA-AML and TF(vSRC) cells following 24 and 48 h ARR exposure, respectively. The plots show the distribution of classes of fluorescence intensity versus cell number. The bottom left quadrant represents live cells (both annexin V-FITC and PI negative); the bottom right quadrant represents early apoptotic cells (annexin V-FITC positive but PI negative); and the top right quadrant represents late apoptotic cells (both annexin V-FITC and PI positive). B) Percentage of early apopotic Annexin V-positive cells at the indicated times. The error bars represent the mean of three separate determinations +/− the standard deviation (SD). *,  and * were significantly different in comparison to control cells. (p values of <0.05, <0.01 and <0.001 respectively, as determined by the t test).
Figure 4:
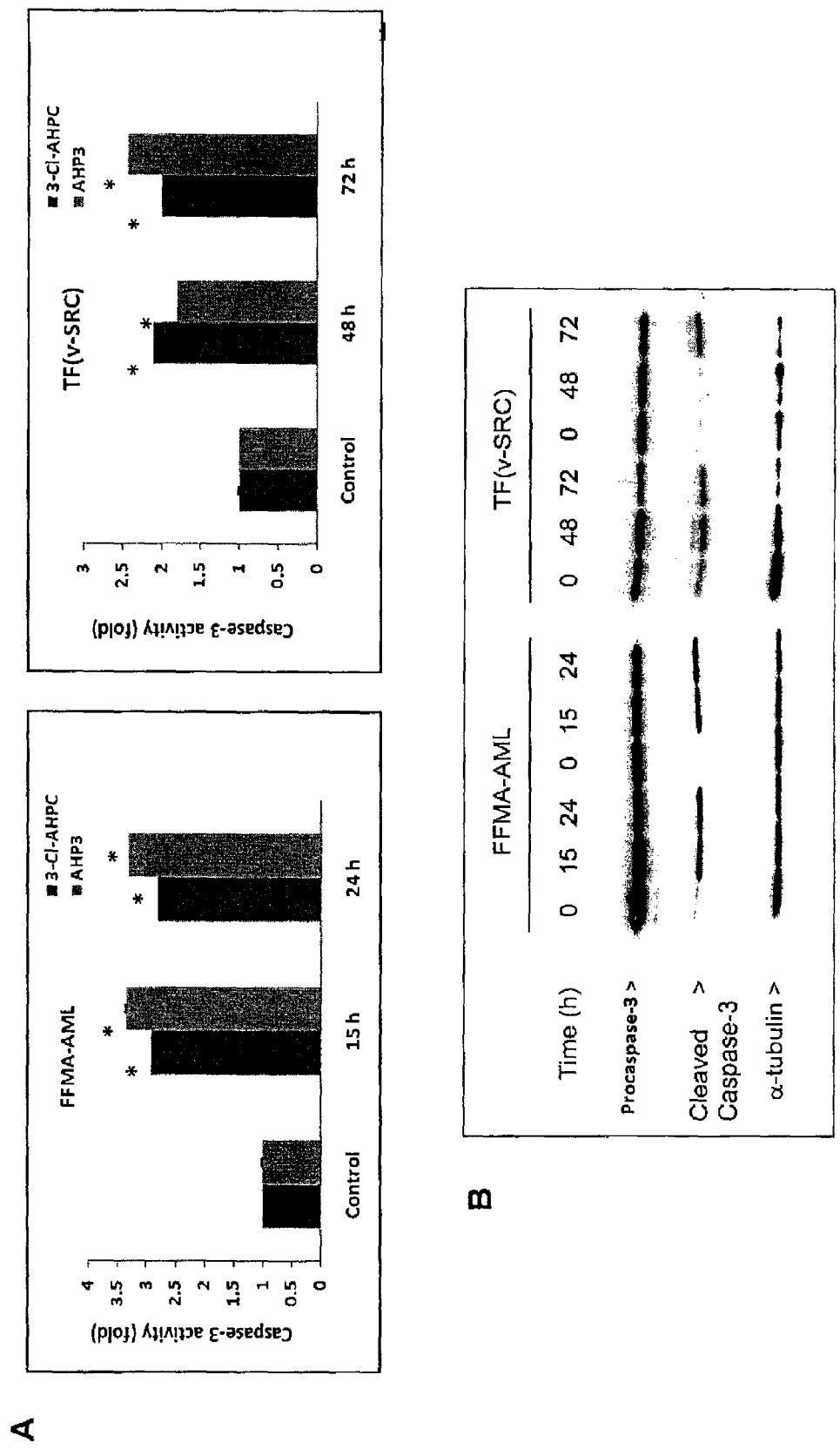
FIG. 4 illustrates 3-Cl-AHPC and compound 16-mediated caspase-3 activation and cleavage of caspase-3. A) Activation of caspase-3 in FFMA-AML and TF(vSRC) cells following exposure to 1 μM 3-Cl-AHPC and compound 16 for varying times. B) Generation of the caspase-3 (17 kDa) fragment and caspase-3 protein levels (α-tubulin used as loading control). Columns represent mean of three independent experiments. Error bars indicate standard deviations. *, significantly different from activation in control cells. (p value is <0.01 as determined by t test).

To further document 3-Cl-AHPC and compound 16-mediated apoptosis in the FFMA-AML and TF(v-SRC) cells, cells were exposed to 1 µM 3-Cl-AHPC or compound 16 for varying times, and then annexin V-FITC binding assessed using flow cytometry. There was a progressive increase in annexin V-FITC-positive cells with time (FIG. 3). Previous studies showed that (CD437/AHPN) and 3-Cl-AHPC induced apoptosis in variety of malignant cells through a caspase-dependent process (Mologni L et al., Blood, 1999; 93:1045-106, Farhana, L. et al., Molecular Cancer Therapeutics, 2009; 8:1625-1635). 3-Cl-AHPC and compound 16 induced caspase-3 activation as indicated by the generation of the catalytically active 17-kDa cleaved caspase-3 protein (FIG. 4A) and increased caspase-3 activity (FIG. 4B) in lysates from the treated AML cells.

The ability of a compound of the invention to act as an inducer of apoptosis was determined using Test C described below.

Test C.

Inhibition of Expression of Anti-Apoptotic Protein X-Linked Inhibitor of Apoptosis Protein (MAP), Cellular Inhibitor of Apoptosis 1 (c-IAP1), and Phospho-Bad.

Figure 5:
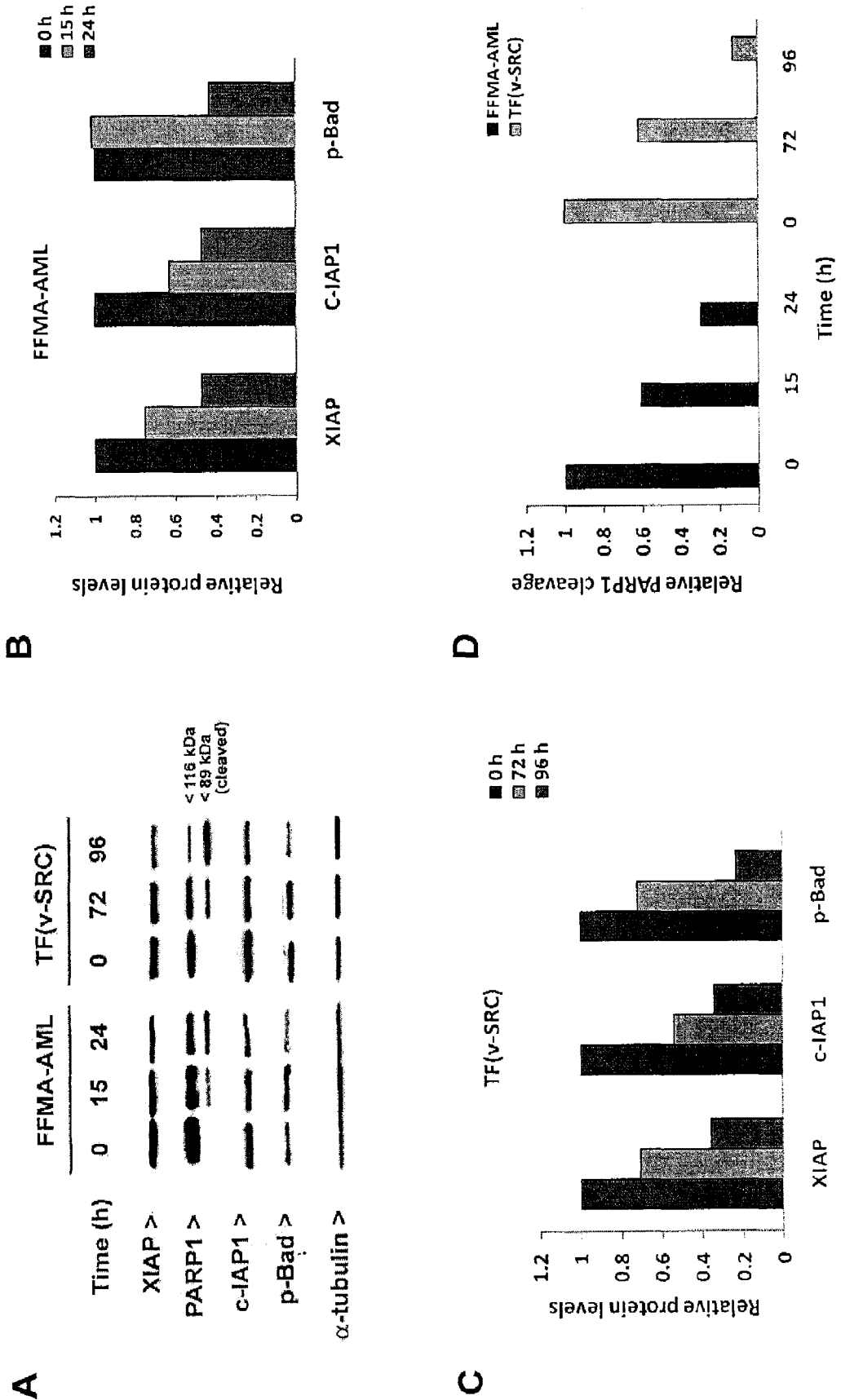
FIG. 5 illustrates compound 16-mediated inhibition of XIAP, c-IAP1, and phospho-Bad expression in FFMA-AML and TF(v-SRC) cells accompanied by the induction of PARP cleavage. A) XIAP, c-IAP and phospho-Bad protein expression following exposure to compound 16 assessed by Western blot. B)-D) Protein expression levels quantified using laser densitometry. The expression levels of XIAP, c-IAP1 and phospho-Bad were normalized to the respective α-tubulin level and compared to their relative levels in the controls, which were given an arbitrary value of 1.

Previous research has demonstrated that exposure of breast and prostate cancer cells to 3-Cl-AHPC resulted in the decreased expression of the anti-apoptotic proteins XIAP and c-IAP1 (Farhana L. et al., Cancer Res. 2006; 65:4909-4917). The proteins c-IAP1, c-IAP2, and XIAP bind caspases resulting in inhibition of caspase activity (Jin H-S. et al., Cancer Res. 2009; 69:1782-1701). In addition, c-IAP1 and c-IAP2 possess E3-ligase activity and play important roles in NFκB activation (Jin H-S. et al., 2009). The Bcl-2 family member Bad enhances apoptosis and is inactivated through phosphorylation to phosphorylated Bad (Eisenmann K. M. et al., Cancer Res. 2003; 63:8330-8337). To assess modulation of anti-apoptotic protein expression during the induction of apoptosis in the AML cells by compound 16, the expression of XIAP, c-IAP1 and phospho-Bad as well as cleavage of the DNA-damage repair poly(ADP-ribose)polymerase (PARP) was assessed following exposure of the AML cells to compound 16. Compound 16 exposure of FFMA-AML and TF(v-SRC) cells in vitro resulted in 70% to 80% decreased expression of the anti-apoptotic proteins XIAP and c-IAP-1, and phospho-Bad. In addition, cleavage of PARP was noted following the decrease in c-IAP1, XIAP and phospho-Bad levels to further document induction of apoptosis in the AML cells by compound 16 (FIG. 5).

The ability of a representative compound of the invention to inhibit FFMA-AML cell growth in mice was determined using Test D described below.

Test D.

3-Cl-AHPC and Compound 16 Inhibition of FFMA-AML Growth in NOD-SCID Mice.

Figure 6:
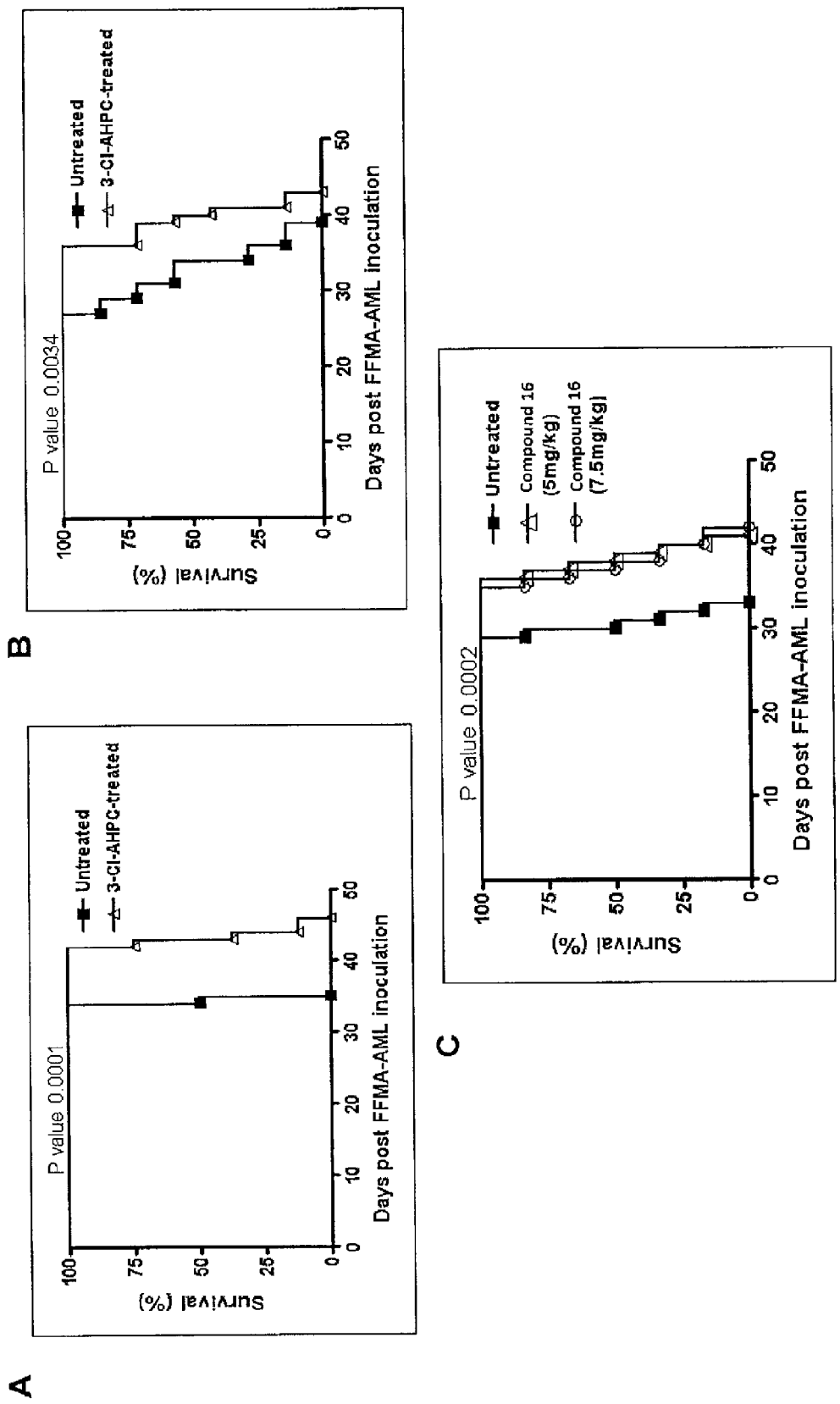
FIG. 6 illustrates 3-Cl-AHPC and compound 16 inhibition of FFMA-AML cell proliferation in NOD-SCID mice and prolongation of their survival. A) Sixteen NOD-SCID mice, which had been randomized into two groups of eight each, were injected through the tail vein with $1 \times 10^6$ FFMA-AML cells. Intravenous injection of vehicle or 3-Cl-AHPC (30 mg/kg) twice daily for 4 days was instituted 24 h later. B) An identical study was performed with the exception that 3-Cl-AHPC was administered interperitoneally. C) Twenty four NOD-SCID mice were randomized into three groups of eight. Each mouse was injected with $1 \times 10^6$ FFMA-AML cells; 24 h later after injection, treatment was started with either vehicle or compound 16 given at doses 7.5 mg/kg or 5.0 mg/kg intravenously twice daily through the tail vein for 5 days. The mice were monitored for toxicity and survival.

The ability of 3-Cl-AHPC and compound 16 to inhibit the growth of FFMA-AML cells in NOD-SCID mice was determined. NOD-SCID mice randomly assigned to two groups of eight mice each were injected with 1 million cells through the tail vein. The mice then received either vehicle or 3-Cl-AHPC (30 mg/kg) given intravenously twice daily for 4 days. 3-Cl-AHPC treatment of the NOD-SCID mice resulted in a significant (p value 0.0001) increase in the length of survival (25%) over mice treated with vehicle only (FIG. 6A). Similar results were obtained when 3-Cl-AHPC was given through an intraperitoneal route using the same dosage of 3-Cl-AHPC and treatment schedule (FIG. 6B). Treatment of the mice with 3-Cl-AHPC was associated with toxicity including weight loss and decreased physical activity. Tail vein injection of NOD-SCID mice with FFMA-AML cells and treatment 24 h later with compound 16, at doses of either 5.0 mg/kg or 7.5 mg/kg given twice a day for 4 days resulted in a significant increase in survival (p=0.0002) compared to that noted in mice treated with vehicle alone (ILS 26%) (FIG. 6C). Compound 16 therapy was extremely well tolerated and no toxicity was noted in the mice. Accordingly, compounds of the invention may be useful as therapeutic agents with a decreased toxicity profile for the treatment of cancer including AML.

The ability of a representative compound of the invention to inhibit TF(v-SRC) cell growth in mice was determined using Test E described below.

Test E.

Compound 16 Inhibition of TF(v-SRC) Cell Growth in SCID Mice.

Figure 7:
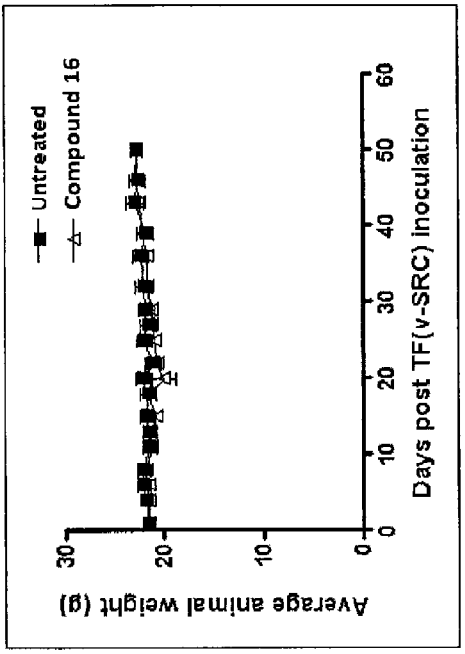
FIG. 7 illustrates compound 16 inhibited TF(v-SRC) proliferation and growth in SCID mice. NOD SCID mice were randomized into two groups of eight. Each mouse was injected with $1 \times 10^7$ TF(v-SRC) cells and 24 h later mice were either treated intravenously with compound 16 (20 mg/kg) or vehicle on a Monday, Wednesday and Friday schedule for five weeks. Mice were monitored for toxicity and survival. A) Survival of TF(vSRC) inoculated mice treated with compound 16, and B) absence of weight loss in compound 16 treated SCID mice. C) compound 16 inhibited palpable TF(v-SRC) growth in SCID mice. TF(v-SRC) cells were grown subcutaneously in a maintenance SCID mouse. The tumor was harvested and approximately 20 mg of tumor was subcutaneously injected utilizing a trochar into each flank of a SCID mouse. The tumors were then allowed to reach a size of 100 mg. The mice were randomized into three groups of 8 mice. Groups were treated either intravenously or subcutaneously at a distant site from the tumor with 20 mg/kg of compound 16 on a Monday, Wednesday and Friday schedule for 12 injections (4 weeks). Control mice were treated intravenously with vehicle.
Figure 7:
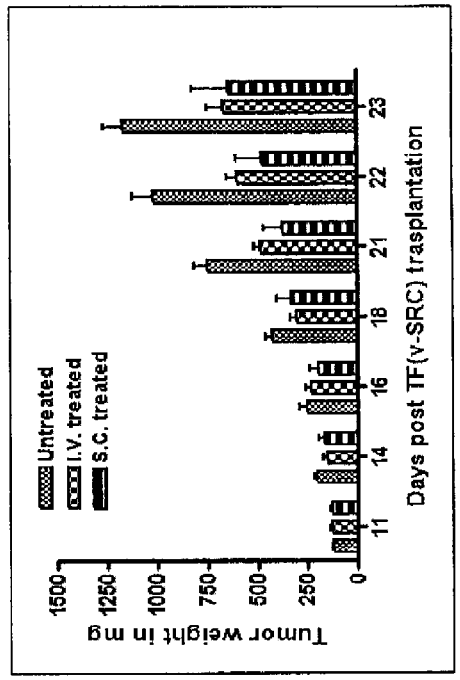
Figure 7:
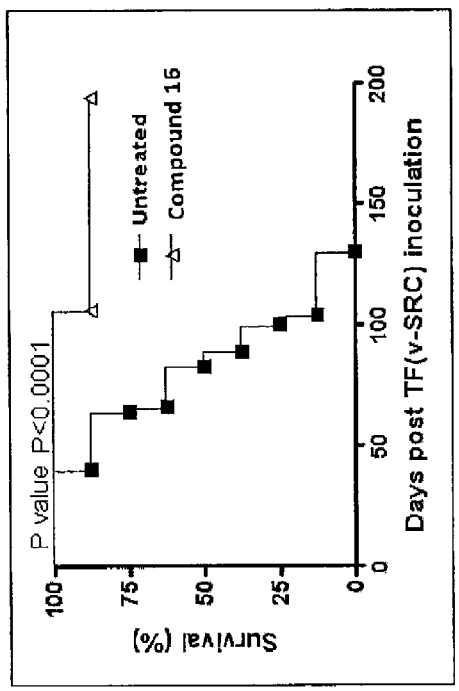

The ability of compound 16 to inhibit the growth of TF(v-SRC) cells in SCID mice was determined. SCID mice were injected with 10 million TF(v-SRC) cells. The mice were treated intravenously with compound 16 (20 mg/kg) or vehicle every other day for a total of 15 doses. Treatment with compound 16 resulted in a marked increase in the length of survival with no evidence of leukemia in 87% of the treated mice (FIG. 7A). TF(v-SRC) growth in the SCID mice was documented by flow cytometry. Flow cytometric analysis of lymph node or tumor sample specimens obtained from the mice treated with vehicle alone revealed the presence of TF(v-SRC) cells with expression of CD45, CD13, CD34, CD33, CD36 and CD40 in the lymph nodes and tumor specimens (Table 2). No malignant cells were identified in the compound 16 treated cells.

TABLE 2

TF(v-SRC) involvement of vehicle treated SCID mice

| Lymph Node | | Tumor | |
|---|---|---|---|
| MoAb/CD number | Positive (%) | MoAb/CD number | Positive (%) |
| CD45 | 99 | CD45 | 98 |
| CD13 | 84 | CD13 | 52 |
| CD34 | 43 | CD34 | 26 |
| CD33 | 93 | CD33 | 78 |
| CD40 | 90 | CD40 | 34 |
| CD36 | 68 | CD36 | 57 |

Compound 16-treated mice did not display any evidence of weight loss as compared to the vehicle-treated mice (FIG. 7B). In addition, the compound 16-treated mice did not display any evidence of diarrhea, dehydration, scruffy coat, or decreased physical activity.

The ability of a representative compound of the invention to inhibit tumor growth was determined using Test F described below.

Test F.
Inhibition of the Growth of Palpable TF(v-SRC) Tumors with Compound 16.

Compound 16 modulation of c-IAP1, Ki67, activated caspase 3, phospho-p65, DR4, and DR5 levels was examined during compound 16 inhibition of TF(v-SRC) tumor growth experiment. TF(v-SRC) cells were trocared subcutaneously in SCID mice and allowed to form palpable tumors. When the palpable tumors reached a size of 100 mg, the mice received either vehicle or compound 16 (FIG. 7C). Compound 16 was given either subcutaneously at a remote site from the palpable tumor or intravenously at a dose of 20 mg/kg every other day for 4 doses. Control mice received vehicle intravenously. Compound 16 treatment given either intravenously or subcutaneously resulted in a 55% reduction in TF(v-SRC) growth (FIG. 7C).

The ability of a representative compound of the invention to have an enhanced therapeutic window was determined using Test G described below.

Test G.
Effect on Body Weight of Repeated Dosing of Compound 16 Versus 3-Cl-AHPC in Mice.

Figure 8:
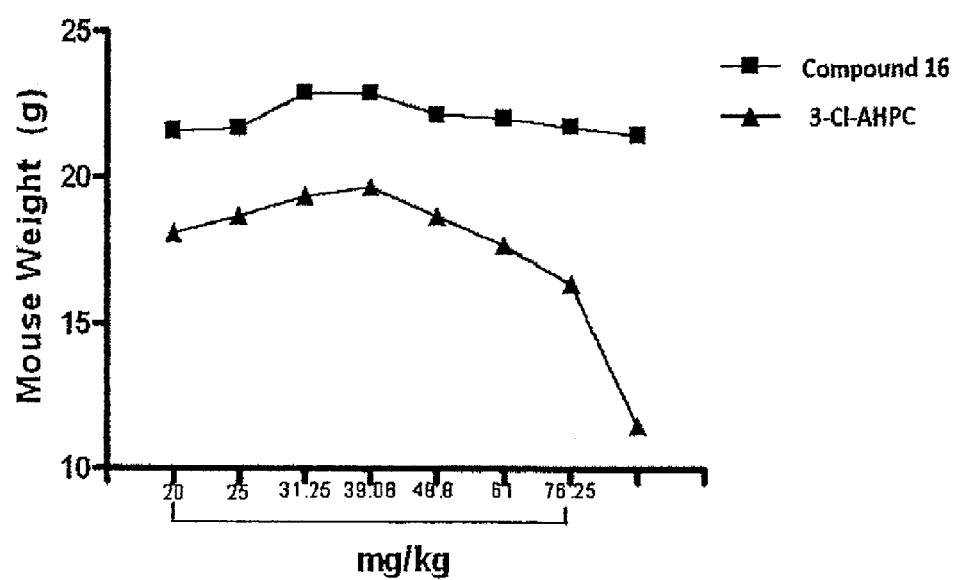
FIG. 8 illustrates the effect on body weight of repeated dosing of compound 16 versus 3-Cl-AHPC in mice.

Mice were treated with escalating doses of either compound 16 or 3-Cl-AHPC to establish the difference in toxicity (MTD) between these compounds as measured by decreased body weight (FIG. 8). Two groups of mice, each consisting of two female ICR-SCIDS mice, were injected IV with either compound 16 or 3-Cl-AHPC once a day for 7 days. The initial IV injection of 20 mg/kg for each compound was increased by 25% for each ensuing dose. Body weights were measured on each of the seven days with the final body weights determined 48 hours post final dose. One of the mice in the group treated with 3-Cl-AHPC died 48 hours after the final injection. The final weight for this mouse was recorded 2 hours after death.

The solubility of representative compounds of the invention were determined using Test H described below.

Test H.
Determination of Aqueous Solubility.

Standard curves at the UV $\lambda_{max}$ (330, 350 and 345 nm for 3-Cl-AHPC, 18 and 16, respectively) were generated using 0.245, 0.163, 0.049 and 0.025 mM 3-Cl-AHPC and 0.380, 0.178, 0.053 and 0.027 mM 18 and 16, which were prepared from 1.0% (wt/vol) solutions of compounds in Me$_2$SO. Calibration curves were used to demonstrate linearity of response. Measurements for maximum solubilities in distilled water (pH 5) and phosphate-buffered saline (PBS, pH 7.2) at 22° C. were made by UV absorbance using solutions obtained after saturation at higher temperatures, overnight incubation at 22° C., and centrifugation to remove undissolved material.

| | Solubility (µM) at 22° C. | | |
|---|---|---|---|
| Compound | PBS (pH 7.2) | Distilled water (pH 5) | $\lambda_{max}$ (nm) |
| 3-Cl-AHPC | Not detectable | 4.5 | 330 |
| 18 | 14.0 | 7.0 | 350 |
| 16 | 440 | 54 | 345 |

Thus, representative compounds of the invention such as compounds 18 and 16 display significantly enhanced solubility when compared to related compounds such as 3-Cl-AHPC.

The ability of a representative compound of the invention to induce apoptosis and inhibit the growth of pancreatic cells was determined using Test I described below.

Test I.
Apoptosis and Growth Inhibition of Pancreatic Cells by Compound 16 and 3-Cl-AHPC.

Pancreatic cancer cell lines (COLO357, PANC-1, Capan-2, AsPc-1 cells and MiaPaCa-2 cells obtained from American Type Culture Collection; ATCC, Rockville, Md.) were treated with 1 µM 3-Cl-AHPC and compound 16 for various times. Apoptosis in cells were analyzed by flow cytometry using Annexin V-FITC binding together with propidium iodide (PI) staining (Annexin V-FITC apoptosis Detection Kit 1, BD Biosciences, San Diego, Calif.). Data acquisition was done on a FACS Calibur flow cytometer (BD) and analyzed with CellQuest software (BD Biosciences). 3-Cl-AHPC and compound 16 mediated inhibition of cell growth were determined by 3-(4,5-dimethylthiazol-2-yl)-2,5-diphenyltetrazolium bromide (MTT) assay. The cells were seeded on 96-well plates at a density of $4 \times 10^4$ cells/well in a volume of 200 µl culture medium. 1 µM AHP3 and 3-Cl-AHPC in DMSO (final concentration 0.1%) were added to the cells for various times. 25 µl/well of MTT (5 mg/ml) were added to the medium and incubated for 4 h. After discarding the medium, MTT precipitates were solubilized with 200 µl DMSO and the plates read on a BioTeK Synergy HT (BioTeK Instrument Inc., Vermont) at an absorbance 570 nm. All experiments were performed in quadruplicate to determine means and standard deviations. The spheroids were stained with acridine orange/ethidium bromide staining and immediately visualized and photographed with fluorescence microscope (OLYMPUS CKX41). For DAPI staining, the spheroids were incubated with DAPI stain for 30 minutes at 37° C. Then spheroids were visualized and photographed with a fluorescence microscope.

Exposure of COLO357, PANC-1, Capan-2, AsPc-1 cells and MiaPaCa-2 cells to 1 µM of either compound 16 or 3-Cl-AHPC resulted in significant inhibition of growth and the induction of apoptosis. Induction of apoptosis was noted in 80% of the COLO357 cells at 48 h and in 50% of the PANC-1 and Capan-2 cells at 48 h. Apoptosis was also noted in the AsPc-1 and MiaPaCa-2 cells at 72 h.

The ability of a representative compound of the invention to induce apoptosis and inhibit the growth of pancreatic cancer stem cells was determined using Test J described below.

Test J.
Apoptosis and Growth Inhibition of Pancreatic Cancer Stem Cells (Obtained from PANC-1, Capan-2 and MiaPaCa-2 Cells) by Compound 16 and 3-Cl-AHPC.

Isolation of CD44+/CD24+ Cells:

Cells were grown to 70-80% confluence and then trypsinised and washed with sorting buffer (1×PBS, 5% FCS). The cells were resuspended with 100 μA sorting buffer and incubated with 15-20 μl anti-CD24-FITC, anti-CD44-PE primary antibodies for 30 min at ice. The cells were washed and resuspended in 500 μl of sorting buffer and sorted using FACSAria system (BD Immunocytochemistry Systems, Franklin lakes, NJ).

Spheroid Formation:

The sorted CD44+/CD24+ cells were suspended in serum-free stem cell medium containing DMEM/F12 (1:1) supplemented with B27 (Life Technologies, Gaithersburg, Md.), 20 ng/ml EGF (Biomol International, Plymouth, Pa.)), 20 ng/ml fibroblast growth factor (Biomol International, Plymouth, Pa.), and 100 μg/ml gentamycin. Approximately 150-200 cells per well were seeded in an ultra low-attachment 96-well plate (Corning Inc, Lowell, Mass.). 3-Cl-AHPC and compound 16 were added the day after cells were plated or after 7 days of spheroid formation. Spheriods were photographed and measured utilizing a Olympus microscope (OLYMPUS CKX41) and Olympus microscope digital camera with DP2-BSW software (Olympus soft imaging solutions GmbH, Germany).

Western Blots:

Cells were extracted with lysis buffer containing 25 mM Tris-Cl buffer (pH 8.0), 150 mM NaCl, 0.2% nonidet P-40, 10% glycerol 10 mM NaF, 8 mM β-glycerophosphate, 0.2 mM Na3VO4, 1 mM DTT, and 10 μl/ml protease inhibitor cocktail (Sigma Aldrich, St. Louise, Mo.) and Western blots were performed as we previously described.

Immunofluoresence:

Approximately 150 spheroids were fixed with 4% paraformaldehyde in 1% Triton X-100, washed in PBS, dehydrated in methanol (25%, 50%, 75% 95% & 100%) and then rehydrated in descending percentage of methanol and washed in PBS. Spheriods were incubated in 3% normal goat serum (Vector Lab, Burlingame, Calif.) at 4° C. for 24 h and washed in phosphate buffered saline with 0.5% Tween 20 (PBST). Then spheriods were incubated with primary antibodies anti-CD44 and anti-CD24 for 48 h at 4° C., washed in PBST and incubated with anti-mouse IgGTRITC conjugate for CD44 and anti-rabbit IgG-FITC conjugate for CD24+ for 24 h. Spheriods were mounted in 8 chambered slides and fluorescence staining analyzed. Spheriods grown in 96 well ultra low attachment plates were incubated with DAPI at 37° C. for 30 minutes to assess DAPI staining.

Spheroid Block Preparation and In Situ Spheroid Cell Death Detection:

DMSO (vehicle) and 3-Cl-AHPC treated spheroids were centrifuged at 1000 rpm for 5 minutes, washed in PBS, 22% bovine serum albumin added to the spheroids pellet, 95% ethanol placed on the spheroids pellet and the pellet allowed to harden for 30 minutes. Neutral buffered formalin (10%) was added to fix the cell pellet for at least 2 h and the spheriods were then placed in a labeled plastic tissue embedding cassette containing 10% neutral buffered formalin overnight. The spheriods were processed in a Sakura Tissue-Tek Processor for overnight dehydration in graded ethanol, clearing in xylene and infiltration with paraffin. The spheriods were placed in a 4 μm embedding mold for final paraffin embedding.

The TUNEL assay was performed using the In Situ Cell Death Detection kit, POD (Roche-Applied-Science, Mannheim, Germany) according to the manufacturer's instructions.

The paraffin embedding spheroids were deparaffinized and rehydrated, then tissues sections were incubated with proteinase K solution (10-20 μg/ml) for 30 min. Tissues were then rinsed twice in PBS and reacted with 50 μl of the TUNEL reaction mixture at room temperature for 60 min in a dark, humidified chamber. Sections were again rinsed in PBS and incubated for 30 min with 50 μl of the Converter-POD (Roche-Applied-Science) and followed by 3-amino-9-ethylcarbazole (AEC). Sections were then counterstained with hematoxylin. As negative controls, corresponding sections were treated in the same way without terminal, deoxynucleotidyl transferase.

shRNA Plasmid:

Human GIPZ lentiviral shRNAmir expression vector GFP-tagged-pGIPZ-shRNA-IGF-1R were purchased from Open Biosystems (Thermo Scientific, Huntsville, Ala.). shRNA-IGF-1R expression vectors were stably transfected into PANC-1 and Capan-2 cell lines using lipofectamine 2000. Stable cell lines were selected with puromycin. The scrambled sequence shRNA-vector was used as a control. pGIPZshRNA expression vector clone ID V2LSH-20147, V2LSH-13 1072, V3LSH-377850, V3LSH-377852, V3LSH-377849 inhibited IGF-1R expression more effectively in PANC-1 cells than other clones from a set of eight tested clones.

Statistical Analysis:

All statistics were performed using VassarStats web statistical software (Richard Lowry, Poughkeepsie, N.Y., USA). One-way analysis of variance (ANOVA) was performed to detect any differences between groups of spheroid control, 3-Cl AHPC treated spheroids and AHP3 treated spheroids. If the result of the ANOVA is significant (P<0.01 vs control), pair wise comparisons between the groups were made by a post-hoc test (Tukey's HSD procedure). The significance level was set at P<0.01 vs control and *P<0.05 vs control.

The addition of compound 16 or 3-ClAHPC to these CD24+/CD44+ cells inhibited their ability to form spheroids. Furthermore, the addition of compound 16 or 3-Cl-AHPC to the pancreatic cancer stem cell spheroids resulted in their disaggregation and the induction of apoptosis in the cells comprising the spheroid. Compound 16 and 3-Cl-AHPC inhibition of spheroid formation as well as the induction of apoptosis in the spheroid forming cells as documented by DNA fragmentation and positive TUNEL staining occurred at achievable physiologic concentrations with exposure of as little as 500 nM of compound 16 or 3-Cl-AHP3 resulting in the disaggregation of the spheroid and the induction of apoptosis.

The invention will now be illustrated by the following non-limiting examples.

EXAMPLES

Example 1

Synthesis of Compound 16: (E)-3-[2-(3-(1-Adamantyl)-4-hydroxyphenyl)-5-pyrimidinyl]-2-propenoic acid To a solution of ethyl(E)-3-[2-(3-(1-adamantyl)-4-hydroxy)-5-pyrimidinyl]-2-propenoate (1.8 g, 4.4 mmol) in methanol (45 mL) was added 5 M aqueous sodium hydroxide (4.44 mL, 22.2 mmol). The mixture was heated at 82° C.

under argon for 1 hour, cooled, quenched with dilute hydrochloric acid and extracted into ethyl acetate (380 mL). The extract was washed (brine) and dried. The concentrated residue was chromatographed (1:2:0 to 4:0:1 ethyl acetate/hexane/methanol), and the yellow solid obtained ($R_f$ 0.43, 1:1:04 ethyl acetate/hexane/methanol) on concentration was washed (hexane, methylene chloride and chloroform) to give 1.52 g (91%) of compound 16 as a yellow powder, mp 290-292° C. (decomposed). IR 3315, 2847, 1673, 1435, 1265 cm$^{-1}$; $^1$H NMR (CD$_3$OD) δ 1.86 (bs, 6H, AdCH$_2$), 2.10 (bs, 3H, AdCH), 2.25 (m, 6H, AdCH$_2$), 6.72 (d, J=16.2 Hz, 1H, CH=CHCO), 6.84 (d, J=8.1 Hz, 1H, 5'-ArH), 7.64 (d, J=16.2 Hz, 1H, CH=CHCO), 8.12 (dd, J=8.1 Hz, 1.8 Hz, 1H, 6'-ArH), 8.34 (d, J=2.1 Hz, 1H, 2'-ArH), 8.98 ppm (s, 2H, 4-PyrH, 6-PyrH). HRMS calcd C$_{23}$H$_{24}$N$_2$O$_3$ [M+H]$^+$ 377.1860. found 377.1875.

The intermediate, ethyl(E)-3-[2-(3'-(1-adamantyl)-4'-hydroxy)-5-pyrimidinyl]-2-propenoate was prepared as follows.

a) Ethyl(E)-3-(2-chloro-5-pyrimidinyl)-2-propenoate

A solution of 5-bromo-2-chloropyrimidine (4.03 g, 20.8 mmol), ethyl acrylate (9.06 mL, 83.3 mmol), palladium diacetate (187 mg, 0.830 mmol) and tri(o-tolyl)phosphine (762 mg, 2.50 mmol) in dimethylformamide (22 mL) and diisopropylethylamine (11 mL) was heated at reflux for 3.5 h, then cooled to room temperature and diluted with brine. The suspension was extracted with ethyl acetate. The extract was washed (brine) and dried. After solvent removal at reduced pressure, the residue was chromatographed (silica gel, 11% ethyl acetate/hexane) to give 3.26 g (73%) of ethyl(E)-3-(2-chloro-5-pyrimidinyl)-2-propenoate as a yellow solid, mp 125-127° C. IR 2905, 1698, 1542, 1405, 1160 cm$^{-1}$; $^1$H NMR (CDCl$_3$) δ 1.38 (t, J=7.2 Hz, 3H, OCH$_2$CH$_3$), 4.32 (q, J=7.2 Hz, 2H, OCH$_2$CH$_3$), 6.60 (d, J=16.2 Hz, 1H, CH=CHCO), 7.61 (d, J=16.2 Hz, 1H, CH=CHCO), 8.79 (s, 2H, 4-PyrH, 6-PyrH). HRMS calcd C$_9$H$_9$ClN$_2$O$_2$ [M+H]$^+$ 213.0425. found 213.0428.

b) Ethyl(E)-3-[2-(3-(1-adamantyl)-4-benzyloxyphenyl)-5-pyrimidinyl]-2-propenoate To a solution of 3-(1-adamantyl)-4-benzyloxyphenylboronic acid (Zhang Y. et al., Blood, 2002; 100:2917-2925, Dawson M. I. et al., J. Med. Chem., 2004; 47:3518-3536) (3.62 g, 10.0 mmol) and ethyl (2E)-3-(2-chloro-5-pyrimidinyl)-2-propenoate (1.76 g, 8.30 mmol) in dimethoxyethane (50 mL) was added under argon tetrakis(triphenylphosphine)-palladium (1.15 g, 1.00 mmol) and 2 M aqueous Na$_2$CO$_3$ (10 mL). The reaction mixture was heated at reflux for 18 h, cooled to room temperature, diluted with ethyl acetate, washed (water and brine) and dried. After solvent removal at reduced pressure, the residue was chromatographed (9% to 14% ethyl acetate/hexane) to give 3.98 g (96%) of ethyl(E)-3-[2-(3-(1-adamantyl)-4-benzyloxyphenyl)-5-pyrimidinyl]-2-propenoate as a yellow solid, mp 164-167° C. IR 2903, 1710, 1432, 1225 cm$^{-1}$; $^1$H NMR δ (CDCl$_3$) 1.40 (t, J=7.2 Hz, 3H, OCH$_2$CH$_3$), 1.77 (bs, 6H, AdCH$_2$), 2.11 (bs, 3H, AdCH), 2.26 (bs, 6H, AdCH$_2$), 4.33 (q, J=7.2 Hz, 2H, OCH$_2$CH$_3$), 5.24 (s, 2H, CH$_2$), 6.59 (d, J=16.2 Hz, 1H, CH=CHCO), 7.08 (d, J=8.7 Hz, 1H, 5-ArH), 7.35-7.58 (m, 5H, C$_6$H$_5$), 7.65 (d, J=16.2 Hz, 1H, CH=CHCO), 8.33 (dd, J=8.7 Hz, 2.1 Hz, 1H, 6-ArH), 8.47 (d, J=2.1 Hz, 1H, 2-ArH), 8.91 ppm (s, 2H, 4-PyrH, 6-PyrH). HRMS calcd C$_{32}$H$_{34}$N$_2$O$_3$ [M+H]$^+$ 495.2642. found 495.2636.

c) Ethyl(E)-3-[2-(3-(1-adamantyl)-4-hydroxyphenyl)-5-pyrimidinyl]-2-propenoate

A solution of ethyl(E)-3-[2-(3-(1-adamantyl)-4-benzyloxy)-5-pyrimidinyl]-2-propenoate (2.30 g, 4.65 mmol), 1.0 M boron tribromide (16 mmol) in dichloromethane (16 mL) and dichloromethane (40 mL) was stirred at −78° C. under argon for 2 h, quenched with water and saturated aqueous sodium bicarbonate and extracted into ethyl acetate. The extract was washed (brine) and dried. After solvent removal at reduced pressure, the residue was chromatographed (16% to 20% ethyl acetate/hexane) to give 1.8 g (95%) of ethyl(E)-3-[2-(3-(1-adamantyl)-4-hydroxyphenyl)-5-pyrimidinyl]-2-propenoate as a pale-yellow solid, mp 226-228° C. IR 3345, 2856, 1715, 1456 cm$^{-1}$; $^1$H NMR (CDCl$_3$) δ 1.39 (t, J=7.2 Hz, 3H, OCH$_2$CH$_3$), 1.83 (bs, 6H, AdCH$_2$), 2.13 (bs, 3H, AdCH), 2.24 (bs, 6H, AdCH$_2$), 4.33 (q, J=7.2 Hz, 2H, OCH$_2$CH$_3$), 5.38 (bs, 1H, OH), 6.59 (d, J=16.2 Hz, 1H, CH=CHCO), 6.79 (d, J=8.1 Hz, 1H, 5-ArH), 7.65 (d, J=16.2 Hz, 1H, CH=CHCO), 8.22 (dd, J=8.1 Hz, 2.1 Hz, 1H, 6-ArH), 8.44 (d, J=2.1 Hz, 1H, 2-ArH), 8.90 ppm (s, 2H, 4-ArH, 6-PyrH). HRMS calcd C$_{25}$H$_{28}$N$_2$O$_3$ [M+H]$^+$ 405.2173. found 405.2191.

Example 2

Synthesis of Compound 17: 2-[3-(1-Adamantyl)-4-hydroxyphenyl]-5-(carboxymethylamino)pyrimidine To a solution of ethyl 2-[3-(1-adamantyl)-4-hydroxyphenyl]-5-(carbethoxymethylamino)-pyrimidine (41.6 mg, 0.100 mmol) in 3:2:1 THF/CH$_3$OH/H$_2$O (2.4 mL) was added LiOH.H$_2$O (21 mg, 0.49 mmol). The mixture was stirred at room temperature for 5 h. After solvent removal at reduced pressure, the residue was suspended in 2 N HCl (10 mL) to adjust the pH to 1 before extraction with EtOAc (60 mL). The extract was washed (brine) and dried. After solvent removal at reduced pressure, the residue was chromatographed (20% EtOAc/hexane) to give 38 mg (98%) of compound 17 as a pale-tan solid, mp 235° C. (dec). IR 3420, 2902, 1691, 1215 cm$^{-1}$; $^1$H NMR (DMSO-d$_6$) δ 1.73 (bs, 6H, AdCH$_2$), 2.04 (bs, 3H, AdCH), 2.10 (m, 6H, AdCH$_2$), 4.15 (bs, 1H, NH), 4.43 (s, 2H, NHCH$_2$CO), 6.85 (d, J=8.4 Hz, 1H, 5'-ArH), 7.91 (d, J=8.4 Hz, 1H, 6'-ArH), 8.12 (s, 1H, 2'-ArH), 8.40 (s, 2H, 4-ArH, 6-ArH), 9.93 ppm (s, 1H, OH). HRMS calcd C$_{22}$H$_{25}$N$_3$O$_3$ [M+H]$^+$ 380.1974. found 380.1975.

The intermediate, ethyl 2-[3-(1-adamantyl)-4-hydroxyphenyl]-5-(carbethoxymethylamino)-pyrimidine was prepared as follows.

a) 2-[3-(1-Adamantyl)-4-benzyloxyphenyl]-5-nitropyrimidine

To a solution of 3-(1-adamantyl)-4-benzyloxyphenylboronic acid (1) (833 g, 2.3 mmol) and 2-chloro-5-nitropyrimidine (2) (320 mg, 2.00 mmol) in degassed toluene (15 mL) was added tetrakis(triphenylphosphine)palladium (347 mg, 0.300 mmol), NaHCO$_3$ (336 mg, 4.00 mmol) and degassed H$_2$O (3 mL). The mixture was heated at reflux (90° C. oil-bath) for 24 h, cooled to room temperature and extracted with EtOAc (180 mL). The extract was washed (H$_2$O and brine) and dried. After solvent removal at reduced pressure, the residue was chromatographed (3% EtOAc/hexane) to give 165 mg (19%) of 2-[3-(1-adamantyl)-4-benzyloxyphenyl]-5-nitropyrimidine as a yellow solid, mp 206° C. (dec). IR 2902, 1405, 1179 cm$^{-1}$; $^1$H NMR (CDCl$_3$) δ 1.76 (bs, 6H, AdCH$_2$), 2.09 (bs, 311, AdCH), 2.22 (m, 6H, AdCH$_2$), 5.24 (s, 2H, $C_6H_5CH_2$), 7.07 (d, J=8.7 Hz, 1H, 5'-ArH), 7.34-7.53 (m, 5H, $C_6H_5$), 8.40 (dd, J=8.7 Hz, 2.4 Hz, 1H, 6'-ArH), 8.51 (d, J=2.4 Hz, 1H, 2'-ArH), 9.46 ppm (s, 2H, 4-ArH, 6-ArH). HRMS calcd $C_{27}H_{27}N_3O_3$ [M+H]$^+$ 442.2125. found 442.2137.

b) 5-Amino-2-[3-(1-adamantyl)-4-benzyloxyphenyl] pyrimidine

A solution of 2-[3-(1-adamantyl)-4-benzyloxyphenyl]-5-nitropyrimidine (163 mg, 0.37 mmol) and $SnCl_2.2H_2O$ (418 mg, 1.85 mmol) in anhydrous EtOH (1.7 mL) was heated at 90° C. (oil-bath) for 3.3 h, cooled to room temperature and diluted with $H_2O$ (2 mL). After adjustment of the pH to 7-8 by addition of 2 N NaOH (1.6 mL) and 5% $NaHCO_3$ (3 mL), the resulting mixture was stirred for 40 min and extracted with EtOAc (3×30 mL). The extract was washed (brine) and dried. After solvent removal at reduced pressure, the residue was chromatographed (25% EtOAc/hexane) to give 53 mg (35%) of 5-amino-2-[3'-(1-adamantyl)-4'-benzyloxyphenyl]pyrimidine as a light-purple solid, mp 216-219° C. IR 3424, 2900, 1182 cm$^{-1}$; $^1$H NMR (CDCl$_3$) 1.76 (bs, 6H, AdCH$_2$), 2.08 (bs, 3H, AdCH), 2.24 (m, 6H, AdCH$_2$), 3.74 (bs, 2H, NH$_2$), 5.21 (s, 2H, C$_6$H$_5$CH$_2$), 7.04 (d, J=8.7 Hz, 1H, 5'-ArH), 7.34-7.56 (m, 5H, C$_6$H$_5$), 8.13 (dd, J=8.7 Hz, 2.4 Hz, 1H, 6'-ArH), 8.28 (d, J=2.4 Hz, 1H, 2'-ArH), 8.43 ppm (s, 2H, 4-ArH, 6-ArH). HRMS calcd $C_{27}H_{29}N_3O$ [M+H]$^+$ 412.2389. found 412.2391.

c) 2-[3-(1-Adamantyl)-4-benzyloxyphenyl]-5-(carbethoxymethylamino)pyrimidine To a suspension of 5-amino-2-[3-(1-adamantyl)-4-benzyloxyphenyl]pyrimidine (49 mg, 0.12 mmol) and $K_2CO_3$ (69 mg, 0.50 mmol) in acetone (5 mL) was added ethyl bromoacetate (53 μl, 0.48 mmol). The mixture was heated at reflux under argon for 19 h and cooled to room temperature. After removal of acetone at reduced pressure, the residue was diluted with water (8 mL) and extracted with EtOAc (60 mL). The extract was washed (H$_2$O and brine) and dried. After solvent removal at reduced pressure, the residue was chromatographed (14% EtOAc/hexane) to give 53 mg (89%) of 2-[3-(1-adamantyl)-4-benzyloxyphenyl]-5-(carbethoxymethylamino)pyrimidine as a pale-tan solid, mp 153-156° C. IR 3455, 2901, 1710, 1179 cm$^{-1}$; $^1$H NMR (CDCl$_3$) δ 1.33 (t, J=7.2 Hz, 3H, OCH$_2$CH$_3$), 1.75 (bs, 6H, AdCH$_2$), 2.07 (bs, 3H, AdCH), 2.24 (m, 6H, AdCH$_2$), 4.31 (q, J=7.2 Hz, 2H, OCH$_2$CH$_3$), 4.60 (m, 1H, NH), 4.73 (s, 2H, NHCH$_2$CO), 5.20 (s, 2H, C$_6$H$_5$CH$_2$), 7.03 (d, J=8.4 Hz, 1H, 5'-ArH), 7.32-7.55 (m, 5H, C$_6$H$_5$), 8.17 (dd, J=8.4 Hz, 2.1 Hz, 1H, 6'-ArH), 8.32 (d, J=2.1 Hz, 1H, 2'-ArH), 8.46 ppm (s, 2H, 4-ArH, 6-ArH). HRMS calcd $C_{31}H_{35}N_3O_3$ [M+H]$^+$ 498.2757. found 498.2762.

d) 2-[3-(1-Adamantyl)-4-hydroxyphenyl]-5-(carbethoxymethylamino)pyrimidine

A solution of ethyl 2-[3-(1-adamantyl)-4-benzyloxyphenyl]-5-(carbethoxymethylamino)pyrimidine (51 mg, 0.10 mmol), 1.0 M BBr$_3$ (0.56 mmol) in CH$_2$Cl$_2$ (0.6 mL) and CH$_2$Cl$_2$ (1.4 mL) was stirred at −78° C. under argon for 2 h, quenched with H$_2$O (10 mL) and extracted with EtOAc (100 mL). The extract was washed (water and brine) and dried. After solvent removal at reduced pressure, the residue was chromatographed (1:4 EtOAc/hexane) to give 41.6 mg (99%) of 2-[3-(1-adamantyl)-4-hydroxyphenyl]-5-(carbethoxymethylamino)pyrimidine as a pale-tan solid, mp 190° C. (dec). IR 3432, 2904, 1708, 1211 cm$^{-1}$; $^1$H NMR (CDCl$_3$) δ 1.32 (t, J=7.2 Hz, 3H, OCH$_2$CH$_3$), 1.79 (bs, 6H, AdCH$_2$), 2.09 (bs, 3H, AdCH), 2.21 (m, 6H, AdCH$_2$), 4.30 (q, J=7.2 Hz, 2H, OCH$_2$CH$_3$), 4.60 (m, 1H, NH), 4.72 (s, 2H, NHCH$_2$CO), 5.85 (s, 1H, OH), 6.71 (d, J=8.4 Hz, 1H, 5'-ArH), 8.03 (dd, J=8.4 Hz, 2.1 Hz, 1H, 6'-ArH), 8.27 (d, J=2.1 Hz, 1H, 2'-ArH), 8.45 ppm (s, 2H, 4-ArH, 6-ArH). HRMS calcd $C_{24}H_{29}N_3O_3$ [M+H]$^+$ 408.2287. found 408.2291.

Example 3

Synthesis of Compound 18: Ethyl(E)-3-{6-[3'-(1-adamantyl)-4'-hydroxyphenyl]-3-pyridinyl}-2-propenoate A solution of ethyl(E)-3-{6-[3'-(1-adamantyl)-4'-benzyloxyphenyl]-3-pyridinyl}-2-propenoate (2.49 g, 5.04 mmol), 1.0 M BBr$_3$ (25 mmol) in CH$_2$Cl$_2$ (25 mL) and CH$_2$Cl$_2$ (45 mL) was stirred at −78° C. under argon for 2 h, then quenched with water (60 mL) and sat. NaHCO$_3$ until pH 7-8 and extracted with EtOAc (800 mL). The extract was washed (water and brine) and dried. After solvent removal at reduced pressure, the residue was chromatographed (14% to 33% EtOAc/hexane) to give 2.0 g (98%) of compound 18 as a yellow solid, mp 215-217° C. IR 3406, 2899, 1707, 1478, 1589, 1250 cm$^{-1}$; $^1$H NMR (CDCl$_3$) δ 1.39 (t, J=7.2 Hz, 3H, OCH$_2$CH$_3$), 1.83 (bs, 6H, AdCH$_2$), 2.14 (bs, 3H, AdCH), 2.22 (bs, 6H, AdCH$_2$), 4.32 (q, J=7.2 Hz, 2H, OCH$_2$CH$_3$), 5.50 (br s, 1H, OH), 6.53 (d, J=15.9 Hz, 1H, CH=CHCO), 6.78 (d, J=8.1 Hz, 1H, 5'-ArH), 7.70-7.76 (m, 3H, 5-ArH, 6'-ArH, CH=CHCO), 7.89 (dd, J=8.4 Hz, 2.4 Hz, 1H, 4-ArH), 7.98 (d, J=2.1 Hz, 1H, 2'-ArH), 8.79 ppm (d, J=2.4 Hz, 1H, 2-ArH). HRMS calcd $C_{26}H_{29}NO_3$ [M+H]$^+$ 404.2220. found 404.2219.

The intermediate, ethyl(E)-3-{-6-[3'-(1-adamantyl)-4'-benzyloxyphenyl]-3-pyridinyl}-2-propenoate, was prepared as follows.

a) Ethyl(E)-3-(6-Bromo-3-pyridinyl)-2-propenoate

A solution of 6-bromo-3-pyridinecarboxaldehyde (3.06 g, 15.63 mmol) and (carbethoxymethylene)triphenylphosphorane (6.60 g, 17.97 mmol) in toluene (45 mL) was heated at reflux overnight and then cooled to room temperature. After solvent removal at reduced pressure, the residue was chromatographed (16% EtOAc/hexane) to give 3.9 g (97%) of ethyl(E)-3-(6-bromo-3-pyridinyl)-2-propenoate as a pale-yellow solid. Recrystallization from hexane yielded 3.5 g (87%) of pure E-isomer as a white solid, mp 79-80° C. By comparison, the material prepared by the literature method (van den Heuvel, M., et al., *J. Org. Chem.*, 2004, 69, 250-262) had a melting point of 83.6-84.1° C. IR 2979, 1709, 1462, 1179 cm$^{-1}$; $^1$H NMR (CDCl$_3$) δ 1.36 (t, J=7.2 Hz, 3H, OCH$_2$CH$_3$), 4.31 (q, J=7.2 Hz, 2H, OCH$_2$CH$_3$), 6.53 (d, J=16.2 Hz, 1H, CH=CHCO), 7.55 (d, J=8.1 Hz, 1H, 5-ArH), 7.68 (d, J=16.2 Hz, 1H, CH=CHCO), 7.72 (dd, J=2.1 Hz, 8.1 Hz, 1H, 4-ArH), 8.52 ppm (d, J=2.1 Hz, 1H, 2-ArH).

b) Ethyl(E)-3-{6-[3'-(1-Adamantyl)-4'-benzyloxyphenyl]-3-pyridinyl}-2-propenoate To a solution of 3-(1-adamantyl)-4-benzyloxyphenylboronic acid (3.62 g, 10 mmol) and ethyl(E)-3-(6-bromo-3-pyridinyl)-2-propenoate (2.12 g, 8.3 mmol) in degassed DME (50 mL) was added tetrakis(triphenylphosphine)palladium (1.15 g, 1.0 mmol) and 2 M aq Na$_2$CO$_3$ (10 mL). The mixture was heated at reflux (92° C. oil-bath) for 20 h, then cooled to room temperature, diluted with EtOAc (300 mL), washed (H₂O and brine) and dried. After solvent removal at reduced pressure, the residue was chromatographed (12% to 25% EtOAc/hexane) to give 4 g (97%) of ethyl(E)-3-{6-[3'-(1-adamantyl)-4'-benzyloxyphenyl]-3-pyridinyl}-2-propenoate as a pale-yellow solid, mp 60-63° C. IR 2901, 1710, 1234, 1176 cm⁻¹; ¹H NMR (CDCl₃) δ 1.39 (t, J=7.2 Hz, 3H, OCH₂CH₃), 1.77 (bs, 6H, AdCH₂), 2.10 (bs, 3H, AdCH), 2.25 (bs, 6H, AdCH₂), 4.32 (q, J=7.2 Hz, 2H, OCH₂CH₃), 5.22 (s, 2H, ArCH₂), 6.53 (d, J=16.2 Hz, 1H, CH=CHCO), 7.07 (d, J=8.7 Hz, 1H, 5'-ArH), 7.28-7.57 (m, 5H, ArH), 7.72 (d, J=16.2 Hz, 1H, CH=CHCO), 7.75 (d, J=8.4 Hz, 1H, 5-ArH), 7.85 (dd, J=8.4 Hz, 2.4 Hz, 1H, 6'-ArH), 7.90 (dd, J=8.7 Hz, 2.7 Hz, 1H, 4-ArH), 8.03 (d, J=2.4 Hz, 1H, 2'-ArH), 8.81 ppm (d, J=2.7 Hz, 1H, 2-ArH). HRMS calcd C₃₃H₃₅NO₃ [M+H]⁺ 494.2690. found 494.2687.

Example 4

Synthesis of Compound 19: (E)-3-{6-[3'-Adamantyl)-4'-hydroxyphenyl]-3-pyridinyl}-2-propionic Acid To a solution of ethyl(E)-3-{6-[3'-(1-adamantyl)-4'-hydroxyphenyl]-3-pyridinyl}-2-propenoate (1.92 g, 4.75 mmol) in MeOH was added 5 M NaOH (4.76 mL, 23.8 mmol). The mixture was heated at 86° C. under argon for 1.5 h, then cooled to room temperature, diluted with 2 N HCl (20 mL) and extracted with EtOAc (60 mL). The extract was washed (brine) and dried. The residue obtained on concentration was washed (hexane, CH₂Cl₂ and CHCl₃) to give on drying 1.69 g (94%) of compound 19 as a yellow solid, mp 316° C. (dec). IR 3363, 2900, 1648, 1589, 1412 cm⁻¹; ¹H NMR (DMSO-d₆) δ 1.77 (bs, 6H, AdCH₂), 2.08 (bs, 3H, AdCH), 2.15 (bs, 6H, AdCH₂), 6.68 (d, J=15.9 Hz, 1H, CH=CHCO), 6.88 (d, J=8.4 Hz, 1H, 5'-ArH), 7.64 (d, J=15.9 Hz, 1H, CH=CHCO), 7.80 (dd, J=8.4 Hz, 2.4 Hz, 1H, 6'-ArH), 7.88 (d, J=8.4 Hz, 1H, 5-ArH), 7.98 (d, J=2.4 Hz, 1H, 2'-ArH), 8.16 (dd, J=8.4 Hz, 2.1 Hz, 1H, 4-ArH), 8.85 (d, J=2.1 Hz, 1H, 2-ArH), 9.78 (s, 1H, OH), 12.31 ppm (bs, 1H, CO₂H). HRMS calcd C₂₄H₂₅NO₃ [M+H]⁺ 376.1907. found 376.1916.

Example 5

Synthesis of Compound 20: (E)-3-{6-[4'-Acetoxy-3'-(1-adamantyl)phenyl]-3-pyridinyl}-2-propionic Acid To a solution of (E)-3-{6-[3'-(1-adamantyl)-4'-hydroxyphenyl]-3-pyridinyl}-2-propionic acid (50 mg, 0.13 mmol) in THF was added Ac₂O (25 μL, 0.27 mmol) and DMAP (33 mg, 0.27 mmol). The mixture was stirred under argon for 27 h, quenched with H₂O (10 mL) and extracted with EtOAc (40, 30 mL). The extract was washed (brine) and dried. After solvent removal at reduced pressure, the residue was chromatographed (1:1:0 to 10:5:1 EtOAc/hexane/MeOH) to give 47 mg (84%) of compound 20 as a pale-yellow solid, mp>260° C. (dec). IR 2900, 1754, 1690, 1204 cm⁻¹; ¹H NMR (DMSO-d₆) δ 1.77 (bs, 6H, AdCH₂), 2.03 (bs, 6H, AdCH₂), 2.10 (bs, 31-1, AdCH), 2.38 (s, 3H, CH₃CO), 6.74 (d, J=15.9 Hz, 1H, CH=CHCO), 7.18 (d, J=8.4 Hz, 1H, 5'-ArH), 7.67 (d, J=15.9 Hz, 1H, CH=CHCO), 7.98 (d, J=8.4 Hz, 1H, 6'-ArH), 8.03 (d, J=8.7 Hz, 1H, 5-ArH), 8.16 (s, 1H, 2'-ArH), 8.25 (d, J=8.7 Hz, 1H, 4-ArH), 8.93 (d, 1H, 2-ArH), 12.43 ppm (bs, 1H, CO₂H). HRMS calcd C₂₆H₂₇NO₄ [M+H]⁺ 418.2013. found 418.2016.

Example 6

Synthesis of Compound 21: (E)-3-{3-[3'-(1-Adamantyl)-4'-hydroxyphenyl]-6-pyridazinyl}-2-propionic Acid To a solution of ethyl(E)-3-{3-[3'-(1-adamantyl)-4'-hydroxyphenyl]-6-pyridazinyl}-2-propenoate (6) (28 mg, 0.07 mmol) in MeOH (1.05 mL) was added 5 M NaOH (70 μL, 0.70 mmol). The solution was heated (82° C. oil-bath) under argon for 50 min, cooled to room temperature, quenched with 2 N HCl (8 mL) and extracted with EtOAc (60 mL). The extract was washed (brine) and dried. The residue obtained on concentration was triturated (hexane and CHCl₃) to give 23 mg (88%) of compound 21 as a yellow solid, mp 181° C. (dec). IR 3373, 2900, 1693, 1543 cm⁻¹; ¹H NMR (MeOH-d₄) δ 1.87 (bs, 6H, AdCH₂), 2.12 (bs, 3H, AdCH), 2.27 (m, 6H, AdCH₂), 6.91 (d, J=8.4 Hz, 1H, 5'-ArH), 6.98 (d, J=16.2 Hz, 1H, CH=CHCO), 7.80 (dd, J=8.4 Hz, 2.1 Hz, 1H, 6'-ArH), 7.88 (d, J=16.2 Hz, 1H, CH=CHCO), 8.00 (d, J=2.1 Hz, 1H, 2'-ArH), 8.03 (d, J=9.0 Hz, 1H, 5-ArH), 8.11 ppm (d, J=9.0 Hz, 1H, 4-ArH). HRMS calcd C₂₃H₂₄N₂O₃ [M+H]⁺ 377.1860. found 377.1873.

The intermediate, ethyl(E)-3-{3-[3'-(1-adamantyl)-4'-hydroxyphenyl]-6-pyridazinyl}-2-propenoate, was prepared as follows.

a) 3-Chloro-6-iodopyridazine

The reported procedure (Goodman, A. J. et al., *Tetrahedron*, 1999, 55, 15067-15070) was followed. A suspension of 3,6-dichloropyridazine (2) (5,000 g, 33.56 mmol), NaI (6.75 g, 45.0 mmol) and HI (55% to 58%, 25 mL) was stirred at 44° C. (oil-bath) under argon for 23 h, cooled to room temperature, and quenched with conc. NaOH to pH 12, then stirred for 10 min and extracted with CH₂Cl₂. The extract was washed (H₂O) and dried. Solvent removal at reduced pressure gave 7.96 g (98%) of 3-chloro-6-iodopyridazine as a pale-yellow solid, mp 114-116° C. (lit: 110-112° C.). ¹H NMR (CDCl₃) δ 7.23 (d, J=8.7 Hz, 1H, 4-ArH), 7.84 ppm (d, J=8.7 Hz, 1H, 5-ArH.

b) Ethyl(E)-3-(3-Chloro-6-pyridazinyl)-2-propenoate

A suspension of 3-chloro-6-iodopyridazine (2.4 g, 10 mmol), ethyl acrylate (4.4 mL, 40 mmol), palladium(II) acetate (90 mg, 0.40 mmol) and tri(o-tolyl)phosphine (366 mg, 1.20 mmol) in DMF (10 mL) and diisopropylethyl amine (5 mL) was stirred with heating (111° C. oil-bath) for 3.5 h, cooled to room temperature, diluted with H₂O (50 mL) and extracted with EtOAc (300 mL). The extract was washed (brine) and dried. After solvent removal at reduced pressure, the residue was chromatographed (14% to 20% EtOAc/hexane) to give 174 mg (8%) of ethyl(E)-3-(3-chloro-6-pyridazinyl)-2-propenoate as a brown solid, mp 106-110° C. IR 2928, 1715, 1186 cm⁻¹; ¹H NMR (CDCl₃) δ 1.38 (t, J=7.5 Hz, 3H, CH₂CH₃), 4.33 (q, J=7.5 Hz, 2H, CH₂CH₃), 7.98 (d, J=16.2 Hz, 1H, CH=CHCO), 7.57 (d, J=8.4 Hz, 1H, 4-ArH), 7.63 (d, J=8.4 Hz, 1H, 5-ArH), 7.86 ppm (d, J=16.2 Hz, 1H, CH=CHCO). HRMS calcd C₉H₉ClN₂O₂ [M+H]⁺ 213.0425. found 213.0431.

c) Ethyl(E)-3-{3-[3'-(1-Adamantyl)-4'-benzyloxyphenyl]-6-pyridazinyl}-2-propenoate To a solution of 3-(1-adamantyl)-4-benzyloxyphenylboronic acid (337 mg, 0.931 mmol) and ethyl(E)-3-(3-chloro- 6-pyridazinyl)-2-propenoate (165 mg, 0.776 mmol) in degassed DME (5 mL) was added tetrakis(triphenylphosphine)palladium (115 mg, 0.100 mmol) and 2 M aq $Na_2CO_3$ (1 mL). The reaction mixture was heated at reflux (90° C. oil-bath) for 20 h, cooled to room temperature and diluted with EtOAc (300 mL). The extract was washed ($H_2O$ and brine) and dried. After solvent removal at reduced pressure, the residue was chromatographed (14% to 20% EtOAc/hexane) to give 59 mg (15%) of ethyl(E)-3-{3-[3'-(1-adamantyl)-4'-benzyloxyphenyl]-6-pyridazinyl}-2-propenoate as a yellow solid, mp 134-136° C. IR 2912, 1710, 1578, 1230 cm$^{-1}$; $^1$H NMR (CDCl$_3$) δ 1.39 (t, J=7.2 Hz, 3H, OCH$_2$CH$_3$), 1.77 (bs, 6H, AdCH$_2$), 2.09 (bs, 3H, AdCH), 2.24 (bs, 6H, AdCH$_2$), 4.34 (q, J=7.2 Hz, 2H, OCH$_2$CH$_3$), 5.24 (s, 2H, ArCH$_2$), 7.02 (d, J=15.9 Hz, 1H, CH=CHCO), 7.11 (d, J=9.0 Hz, 1H, 5-ArH), 7.34-7.51 (m, 3H, ArH), 7.52-7.57 (m, 2H, ArH), 7.65 (d, J=8.7 Hz, 1H, 5'-ArH), 7.86 (d, J=9.0 Hz, 1H, 4-ArH), 7.92 (d, J=15.9 Hz, 1H, CH=CHCO), 7.96 (dd, J=8.7 Hz, 2.1 Hz, 1H, 6'-ArH), 8.15 ppm (d, J=2.1 Hz, 1H, 2'-ArH). HRMS calcd $C_{32}H_{34}N_2O_3$ [M+H]$^+$ 495.2642. found 495.2630.

d) Ethyl(E)-3-{3-[3'-(1-Adamantyl)-4'-hydroxyphenyl]-6-pyridazinyl}-2-propenoate A solution of ethyl(E)-3-{3-[3'-(1-adamantyl)-4'-benzyloxyphenyl]-6-pyridazinyl}-2-propenoate (53 mg, 0.11 mmol), 1.0 M BBr$_3$ (0.43 mmol) in CH$_2$Cl$_2$ (0.43 mL) and CH$_2$Cl$_2$ (2 mL) was stirred at −78° C. under argon for 2 h, quenched with H$_2$O (10 mL) and sat. NaHCO$_3$ to pH 7-8 and extracted with EtOAc (80 mL). The extract was washed (water and brine) and dried. After solvent removal at reduced pressure, the residue was chromatographed (14% to 33% EtOAc/hexane) to give 36 mg (84%) of ethyl(E)-3-{3-[3'-(1-adamantyl)-4'-hydroxyphenyl]-6-pyridazinyl}-2-propenoate as a yellow solid, mp 246-248° C. IR 3360, 2907, 1714, 1568, 1227 cm$^{-1}$; $^1$H NMR (acetone-d$_6$) δ 1.36 (t, J=7.5 Hz, 31-1, OCH$_2$CH$_3$), 1.86 (bs, 6H, AdCH$_2$), 2.13 (bs, 3H, AdCH), 2.30 (bs, 6H, AdCH$_2$), 4.30 (q, J=7.5 Hz, 2H, OCH$_2$CH$_3$), 7.03 (d, J=8.4 Hz, 1H, 5'-ArH), 7.06 (d, J=15.9 Hz, 1H, CH=CHCO), 7.91 (d, J=15.9 Hz, 1H, CH=CHCO), 7.96 (dd, J=8.4 Hz, 2.1 Hz, 1H, 6'-ArH), 8.06 (d, J=9.0 Hz, 1H, 5-ArH), 8.17 (d, J=9.0 Hz, 1H, 4-ArH), 8.20 (d, J=2.1 Hz, 1H, 2'-ArH), 8.96 ppm (s, 1H, OH). HRMS calcd $C_{25}H_{28}N_2O_3$ [M+H]$^+$ 405.2173. found 405.2174.

Example 7

Synthesis of Compound 22: (E)-3-{2-[3'-(1-Adamantyl)-4'-hydroxyphenyl]-3-chloro-5-pyridinyl}-1-propenoic Acid To a solution of ethyl(E)-3-(2-(3'-(1-adamantyl)-4'-hydroxyphenyl)-3-chloro-5-pyridinyl]-2-propenoate (32 mg, 0.073 mmol) in 3:2:1 THF/MeOH/H$_2$O (1.2 mL) at 0° C. was added LiOH.H$_2$O (18.4 mg, 0.44 mmol). This mixture was stirred at 0° C. under argon for 5 h, then quenched with 2 N HCl until pH 3 to 4, and extracted with EtOAc (40, 20 mL). The extract was washed (brine) and dried. The residue obtained on concentration was washed (hexane, CHCl$_3$ and CH$_2$Cl$_2$) to give 26 mg (87%) of compound 22 as a yellow solid, mp 186-188° C. IR 3377, 2901, 1688, 1412 cm$^{-1}$; $^1$H NMR (MeOH-d$_4$) δ 1.85 (bs, 6H, AdCH$_2$), 2.09 (bs, 3H, AdCH), 2.24 (bs, 6H, AdCH$_2$), 6.69 (d, J=15.9 Hz, 1H, CH=CHCO), 6.84 (d, J=8.4 Hz, 1H, 5'-ArH), 7.46 (dd, J=8.4, 2.1 Hz, 1H, 6'-ArH), 7.58 (d, J=2.1 Hz, 1H, 2'-ArH), 7.69 (d, J=15.9 Hz, 1H, CH=CHCO), 8.26 (s, 1H, 4-PyH), 8.70 ppm (s, 1H, 2-PyH). HRMS calcd $C_{24}H_{24}ClNO_3$ [M+H]$^+$ 410.1517. found 410.1515.

The intermediate, ethyl(E)-3-{2-[3'-(1-adamantyl)-4'-hydroxyphenyl]-3-chloro-5-pyridinyl}-2-propenoate was prepared as follows.

a) Ethyl(E)-3-(5,6-Dichloro-2-pyridinyl)-2-propenoate

A reported method (Ognyanov, V. I. et al., *J. Med. Chem.*, 2006, 49, 3719-3742) was used to synthesize 2,3-dichloro-5-formylpyridine. A mixture of 5,6-dichloro-3-pyridinemethanol (1.42 g, 8.00 mmol) and MnO$_2$ (13.9 g, 160 mmol) in 1:1 CH$_2$Cl$_2$/hexane (8 mL) was stirred for 1 h, then diluted with 50% EtOAc/hexane (20 mL), and filtered (50% EtOAc/hexane wash). The filtrate was evaporated, and the residue was dried in vacuo for use in the next step.

A solution of crude 2,3-dichloro-5-formylpyridine and (carbethoxymethylene)triphenylphosphorane (2.14 g, 5.83 mmol) in toluene (12 mL) was heated at reflux overnight and then cooled to room temperature. After solvent removal at reduced pressure, the residue was chromatographed (9% to 10% EtOAc/hexane) to give 323 mg (16% from 5,6-dichloro-3-pyridinemethanol) of ethyl(E)-3-(5,6-dichloro-2-pyridinyl)-2-propenoate as a white solid, mp 102-103° C. IR 2914, 1702, 1428, 1193 cm$^{-1}$; $^1$H NMR (CDCl$_3$) δ 1.37 (t, J=7.2 Hz, 3H, OCH$_2$CH$_3$), 4.31 (q, J=7.2 Hz, 2H, OCH$_2$CH$_3$), 6.53 (d, J=16.2 Hz, 1H, CH=CHCO), 7.62 (d, J=16.2 Hz, 1H, CH=CHCO), 7.94 (d, J=1.8 Hz, 1H, 4-ArH), 8.44 ppm (d, J=1.8 Hz, 1H, 2-ArH). HRMS calcd $C_{10}H_9Cl_2NO_2$ [M+H]$^+$ 246.0083. found 246.0086.

b) Ethyl(E)-3-{2-[3'-(1-Adamantyl)-4'-henzyloxyphenyl]-3-chloro-5-pyridinyl}-2-propenoate To a solution of 3-(1-adamantyl)-4-benzyloxyphenylboronic acid (204 mg, 0.570 mmol) and ethyl(E)-3-(5,6-dichloro-2-pyridinyl)-2-propenoate 4 (123 mg, 0.500 mmol) in degassed DME (6 mL) was added 1,1'-bis(diphenylphosphino)ferrocene-dichloropalladium(II).CH$_2$Cl$_2$ complex (25 mg, 0.03 mmol) and Cs$_2$CO$_3$ (652 mg, 2.00 mmol). The reaction mixture was stirred at 75° C. for 17 h and then at 90° C. for 15 h before being cooled to room temperature, diluted with H$_2$O (30 mL) and extracted with EtOAc (100, 50 mL). The extract was washed (brine) and dried. After solvent removal at reduced pressure, the residue was chromatographed (9% to 11% EtOAc/hexane) to give 85 mg (32%) of ethyl(E)-3-{2-[3'-(1-adamantyl)-4'-benzyloxyphenyl]-3-chloro-5-pyridinyl}-2-propenoate as a viscous pale-yellow oil. IR 2903, 1711, 1233, 1176 cm$^{-1}$; $^1$H NMR (CDCl$_3$) δ 1.39 (t, J=7.2 Hz, 3H, OCH$_2$CH$_3$), 1.76 (bs, 6H, AdCH$_2$), 2.08 (bs, 3H, AdCH), 2.23 (bs, 6H, AdCH$_2$), 4.33 (q, J=7.2 Hz, 2H, OCH$_2$CH$_3$), 5.22 (s, 211, ArCH$_2$), 6.57 (d, J=16.2 Hz, 1H, CH=CHCO), 7.05 (d, J=8.4 Hz, 1H, 5'-ArH), 7.28-7.57 (m, 5H, C$_6$H$_5$), 7.65 (d, J=16.2 Hz, 1H, CH=CHCO), 7.66 (d, J=8.4 Hz, 1H, 6'-ArH), 7.77 (s, 1H, 2'-ArH), 7.95 (s, 1H, 4-PyH), 8.71 ppm (s, 1H, 2-PyH). HRMS calcd $C_{33}H_{34}ClNO_3$ [M+H]$^+$ 528.2300. found 528.2299.

c) Ethyl(E)-3-{2-[3'-(1-Adamantyl)-4'-hydroxyphenyl]-3-chloro-5-pyridinyl}-2-propenoate A solution of ethyl(E)-3-{2-[3'-(1-adamantyl)-4'-benzyloxy]-3-chloro-5-pyridinyl}-2-propenoate (72 mg, 0.14 mmol), 1.0 M boron tribromide (0.55 mmol) in CH$_2$Cl$_2$ (0.6 mL), and CH$_2$Cl$_2$ (2 mL) was stirred at −78° C. under argon for 2 h. The reaction mixture was quenched with water (8 mL)

and sat. NaHCO$_3$ (8 mL) and extracted with EtOAc (70 mL and 40 mL). The extract was washed (brine) and dried. After solvent removal at reduced pressure, the residue was chromatographed (13% to 25% EtOAc/hexane) to give 36 mg (61%) of ethyl(E)-3-{2-[3'-(1-adamantyl)-4'-hydroxyphenyl]-3-chloro-5-pyridinyl}-2-propenoate as a yellow solid, mp 260-261° C. IR 3373, 2905, 1712, 1411, 1183 cm$^{-1}$; $^1$H NMR (CDCl$_3$) δ 1.39 (t, J=7.2 Hz, 3H, OCH$_2$CH$_3$), 1.82 (bs, 6H, AdCH$_2$), 2.12 (bs, 3H, AdCH), 2.20 (bs, 6H, AdCH$_2$), 4.33 (q, J=7.2 Hz, 2H, OCH$_2$CH$_3$), 5.21 (s, 1H, OH), 6.57 (d, J=15.9 Hz, 1H, CH═CHCO), 6.77 (d, J=8.4 Hz, 1H, 5'-ArH), 7.58 (dd, J=1.5, 8.4 Hz, 1H, 6'-ArH), 7.67 (d, J=15.9 Hz, 1H, CH═CHCO), 7.71 (d, J=1.5, 1H, 2'-PyH), 7.96 (s, 1H, 4-PyH), 8.71 ppm (s, 1H, 2-PyH). HRMS calcd C$_{26}$H$_{28}$ClNO$_3$ [M+H]$^+$ 438.2830. found 438.1826.

Example 8

Synthesis of Compound 23: (E)-3-{2-[3-(1-Adamantyl)-4-hydroxyphenyl]-5-pyrazinyl}-2-propenoic Acid To a solution of ethyl(E)-3-[2-(3-(1-adamantyl)-4-hydroxy-5-pyrazinyl]-2-propenoate (7) (310 mg, 0.77 mmol) in MeOH (9 mL) was added 5 M aq NaOH (0.77 mL, 3.83 mmol). The mixture was heated at 81° C. under argon for 1 h, cooled to room temperature, quenched with 2 N HCl (22 mL), and then extracted with EtOAc (100 mL, 50 mL, and 20 mL). The extracts were washed (brine) and dried. The yellow solid obtained on concentration was washed (hexane and CH$_2$Cl$_2$) to give 254 mg (88%) of compound 23 as a yellow powder, mp 296° C. (dec.). $^1$H NMR (CD$_3$OD and CDCl$_3$) δ 1.65 (bs, 6H, AdCH$_2$), 1.95 (bs, 3H, AdCH), 2.06 (bs, 6H, AdCH$_2$), 6.72 (d, J=8.5 Hz, 1H, 5-ArH), 6.78 (d, J=15.9 Hz, 1H, CH═CHCO), 7.55 (d, J=15.9 Hz, 1H, CH═CHCO), 7.57 (dd, J=8.5 Hz, 2.4 Hz, 1H, 6-ArH), 7.77 (d, J=2.4 Hz, 1H, 2-ArH), 8.49 (s, 1H, 3-PyrH), 8.82 ppm (s, 1H, 6-PyrH). HRMS calcd C$_{23}$H$_{24}$N$_2$O$_3$ [M+H]$^+$ 377.1860. found 377.1859.

The intermediate, ethyl(E)-3-{2-[3-(1-adamantyl)-4-hydroxy]-5-pyrazinyl}-2-propenoate was prepared as follows.

a) 5-Bromo-pyrazine-2-carbaldehyde

To a solution of 5-cyano-2-bromopyrazine (1.02 g, 5.54 mmol) in anhydrous toluene (15 mL) at –78° C. was added 1 M diisobutyl aluminum hydride (8.32 mmol) in CH$_2$Cl$_2$ (8.3 mL). The reaction mixture was stirred at –78° C. for 15 min, warmed to room temperature, stirred for 26 h, and then diluted with MeOH (4 mL) and stirred for 30 min at room temperature before addition of 10% H$_2$SO$_4$ (55 mL). The resulting solution was stirred for 1.75 h and extracted with EtOAc (100 mL, 50 mL). After solvent removal at reduced pressure, the residue was chromatographed (11% to 14% EtOAc/hexane) to give 289 mg (28%) of 5-bromo-pyrazine-2-carbaldehyde as an orange solid, mp 56-58° C. IR 2960, 1654, 1546, 1111 cm$^{-1}$; $^1$H NMR (CDCl$_3$) δ 8.83 (d, J=1.24 Hz, 1H, 6-PyrH), 8.91 (d, J=1.24 Hz, 1H, 3-PyrH), 10.13 ppm (s, 1H, CHO). HRMS calcd C$_5$H$_3$BrN$_2$O [M+H]$^+$ 186.9501. found 186.9496.

b) Ethyl(E)-3-(5-Bromo-2-pyrazinyl)-2-propenoate

Method A:
A solution of 5-bromo-pyrazine-2-carbaldehyde (284 mg, 1.52 mmol) and (carbethoxymethylene)triphenylphosphorane (668 mg, 1.82 mmol) in toluene (5 mL) was heated at reflux for 18 h and then cooled to room temperature. After solvent removal at reduced pressure, the residue was chromatographed (11% to 14% EtOAc/hexane) to give 369 mg (94%) of an E and Z mixture of ethyl 3-(5-bromo-2-pyrazinyl)-2-propenoate as a pale-yellow solid. Crystallization (hexane) yielded 243 mg (62%) of the pure E-isomer as a cream solid, mp 70-71° C. IR 2940, 1707, 1457, 1103 cm$^{-1}$; $^1$H NMR (CDCl$_3$) δ 1.33 (t, J=7.3 Hz, 3H, OCH$_2$CH$_3$), 4.28 (q, J=7.3 Hz, 2H, OCH$_2$CH$_3$), 6.99 (d, J=15.9 Hz, 1H, CH═CHCO), 7.62 (d, J=15.9 Hz, 1H, CH═CHCO), 8.40 (d, J=1.24 Hz, 1H, 6-PyrH), 8.68 ppm (d, J=1.24 Hz, 1H, 3-PyrH). HRMS calcd C$_9$H$_9$BrN$_2$O$_2$ [M+H]$^+$ 256.9920. found 256.9915.

Ethyl(E)-3-(5-Bromo-2-pyrazinyl)-2-propenoate

Method B:
A solution of 2,5-dibromopyrazine (238.0 mg, 1.0 mmol), ethyl acrylate (174.0 μL, 1.6 mmol), palladium(II) acetate (3.4 mg, 0.015 mmol), and tri(o-tolyl)phosphine (36.5 mg, 0.12 mmol) in DMF (1.4 mL) and diisopropylethylamine (0.7 mL) was heated at reflux (115° C. oil bath) for 4.4 h, cooled to room temperature, and then quenched with H$_2$O. The suspension was extracted with EtOAc (300 mL). The extract was washed (brine) and dried. After solvent removal at reduced pressure, the residue was purified on silica gel (11% EtOAc/hexane) to give 22 mg (8.5%) of ethyl(E)-3-(5-bromo-2-pyrazinyl)-2-propenoate as a cream solid.

c) Ethyl(E)-3-{2-[3-(1-Adamantyl)-4-benzyloxyphenyl]-5-pyrazinyl}-2-propenoate

To a solution of 3-(1-adamantyl)-4-benzyloxyphenylboronic acid (474 mg, 1.31 mmol) and ethyl(E)-3-(5-bromo-2-pyrazinyl)-2-propenoate (278 mg, 1.08 mmol) in DME (11 mL, degassed) was added tetrakis(triphenylphosphine)palladium (151 mg, 0.13 mmol) and degassed 2 M Na$_2$CO$_3$ (2.3 mL). The reaction mixture was heated at reflux (90° C. oil-bath) for 19.5 h, cooled to room temperature, and then diluted with EtOAc (155 mL). The organic layer was washed (H$_2$O and brine) and dried. After solvent removal at reduced pressure, the residue was purified on silica gel (10% to 25% EtOAc/hexane) to give 488 mg (91%) of ethyl(E)-3-{2-[3-(1-adamantyl)-4-benzyloxyphenyl]-5-pyrazinyl}-2-propenoate as a yellow solid, mp 145-148° C. IR 2899, 1710, 1238 cm$^{-1}$; $^1$H NMR δ (CDCl$_3$) 1.35 (t, J=7.3 Hz, 3H, OCH$_2$CH$_3$), 1.73 (bs, 6H, AdCH$_2$), 2.06 (bs, 3H, AdCH), 2.20 (bs, 6H, AdCH$_2$), 4.29 (q, J=7.3 Hz, 2H, OCH$_2$CH$_3$), 5.19 (s, 2H, CH$_2$), 6.98 (d, J=15.9 Hz, 1H, CH═CHCO), 7.04 (d, J=8.5 Hz, 1H, 5-ArH), 7.28-7.52 (m, 5H, C$_6$H$_5$), 7.72 (d, J=15.9 Hz, 1H, CH═CHCO), 7.84 (dd, J=8.5 Hz, 2.4 Hz, 1H, 6-ArH), 8.02 (d, J=2.4 Hz, 1H, 2-ArH), 8.63 (d, J=1.24 Hz, 1H, 3-PyrH), 8.99 ppm (d, J=1.24 Hz, 1H, 6-PyrH). HRMS calcd C$_{32}$H$_{34}$N$_2$O$_3$ [M+H]$^+$ 495.2642. found 495.2659.

d) Ethyl(E)-3-{2-[3-(1-Adamantyl)-4-hydroxyphenyl]-5-pyrazinyl}-2-propenoate

A solution of ethyl(E)-3-{2-[3-(1-adamantyl)-4-benzyloxyphenyl]-5-pyrazinyl}-2-propenoate (477 mg, 0.96 mmol), 1.0 M boron tribromide (3.86 mmol) in CH$_2$Cl$_2$ (3.86 mL), and CH$_2$Cl$_2$ (13 mL) was stirred at –78° C. under argon for 2 h, quenched with water (50 mL), and extracted with EtOAc (100 mL, 50 mL, and 30 mL). The extracts were washed (brine) and dried. After solvent removal at reduced pressure, the residue was purified on silica gel (20% to 33% EtOAc/hexane) to give 367 mg (94%) of ethyl(E)-3-{2-[3-(1-adamantyl)-4-hydroxyphenyl]-5-pyrazinyl}-2-propenoate as a yellow solid, mp 212-215° C. IR 3352, 2843, 1686 cm$^{-1}$; $^1$H NMR (CDCl$_3$) δ 1.35 (t, J=7.3 Hz, 3H, OCH$_2$CH$_3$), 1.79 (bs, 6H, AdCH$_2$), 2.10 (bs, 3H, AdCH), 2.18 (bs, 6H, AdCH$_2$), 4.29 (q, J=7.3 Hz, 2H, OCH$_2$CH$_3$), 5.32 (s, 1H, OH), 6.77 (d, J=8.5 Hz, 1H, 5-ArH), 6.97 (d, J=15.9 Hz, 1H, CH=CHCO), 7.71 (d, J=15.9 Hz, 1H, CH=CHCO), 7.75 (dd, J=8.5 Hz, 2.4 Hz, 1H, 6-ArH), 7.98 (d, J=2.4 Hz, 1H, 2-ArH), 8.62 (d, J=1.2 Hz, 1H, 3-PyrH), 8.97 ppm (d, J=1.2 Hz, 1H, 6-PyrH). HRMS calcd C$_{25}$H$_{28}$N$_2$O$_3$ [M+H]$^+$ 405.2173. found 405.2181.

Example 9

Synthesis of Compound 24: (E)-3-{5-[3'-(1-Adamantyl)-4' hydroxyphenyl]-2-pyridinyl}-2-propionic Acid To a solution of ethyl(E)-3-{5-[3'-(1-adamantyl)-4'-hydroxyphenyl]-2-pyridinyl}-2-propenoate (130 g, 0.32 mmol) in MeOH (4.5 mL) was added 5 M NaOH (0.32 mL, 1.61 mmol). The mixture was heated at 80° C. under argon for 1.67 h, then cooled to room temperature, diluted with 2 N HCl (20 mL), and concentrated until dryness. The residue was solubilized in MeOH and filtered. Concentration of the filtrate produced a yellow solid that was washed (hexane and CH$_2$Cl$_2$) to give on drying 121 mg (100%) of compound 24 as a yellow solid, mp>260° C. (dec.). $^1$H NMR (CD$_3$OD) δ 1.84 (bs, 6H, AdCH$_2$), 2.09 (bs, 3H, AdCH), 2.23 (bs, 6H, AdCH$_2$), 6.92 (d, J=8.5 Hz, 1H, 5'-ArH), 7.06 (d, J=16.5 Hz, 1H, CH=CHCO), 7.53 (dd, J=2.4 Hz, 8.5 Hz, 1H, 6'-ArH), 7.57 (d, J=2.4 Hz, 1H, 2'-ArH), 7.77 (d, J=16.5 Hz, 1H, CH=CHCO), 8.32 (d, J=8.5 Hz, 1H, 3-ArH), 8.70 (dd, J=1.8 Hz, 8.5 Hz, 1H, 4-ArH), 9.0 ppm (d, J=1.8 Hz, 1H, 6-ArH). HRMS calcd C$_{24}$H$_{25}$NO$_3$ [M+H]$^+$ 376.1907. found 376.1908.

The intermediate, ethyl(E)-3-{5-[3'-(1-adamantyl)-4'-hydroxyphenyl]-2-pyridinyl}-2-propenoate was prepared as follows.

a) Ethyl(E)-3-(5-Bromo-2-pyridinyl)-2-propenoate

A solution of 5-bromo-2-formylpyridine (1.07 g, 5.58 mmol) and (carbethoxymethylene)-triphenylphosphorane (2.46 g, 6.70 mmol) in toluene (13 mL) was heated at reflux for 17 h and then cooled to room temperature. After solvent removal at reduced pressure, the residue was chromatographed (10% to 14% EtOAc/hexane) to give 1.42 g (99%) of 2 as a pale-yellow solid. Crystallization (hexane) yielded 1.28 g (89%) of pure E-isomer as a white solid, mp 78-80° C. $^1$H NMR (CDCl$_3$) δ 1.34 (t, J=7.3 Hz, 3H, OCH$_2$CH$_3$), 4.27 (q, J=7.3 Hz, 2H, OCH$_2$CH$_3$), 6.91 (d, J=15.9 Hz, 1H, CH=CHCO), 7.31 (d, J=8.5 Hz, 1H, 3-ArH), 7.62 (d, J=15.9 Hz, 1H, CH=CHCO), 7.84 (dd, J=2.4 Hz, 8.5 Hz, 1H, 4-ArH), 8.69 ppm (d, J=2.4 Hz, 1H, 6-ArH). HRMS calcd C$_{10}$H$_{10}$BrNO$_2$ [M+H]$^+$ 255.9968. found 255.9967.

b) Ethyl(E)-3-{5-[3'-(1-adamantyl)-4'-benzyloxyphenyl]-2-pyridinyl}-2-propenoate To a solution of 3-(1-adamantyl)-4-benzyloxyphenylboronic acid (235 mg, 0.65 mmol) and ethyl(E)-3-(5-bromo-2-pyridinyl)-2-propenoate (2) (128 mg, 0.5 mmol) in degassed DME (4 mL) was added tetrakis(triphenylphosphine)palladium (58 mg, 0.05 mmol) and 2 M Na$_2$CO$_3$ (0.8 mL). The mixture was heated at reflux (92° C. oil-bath) for 24.5 h, then cooled to room temperature, diluted with EtOAc (130 mL), washed (H$_2$O and brine), and dried. After solvent removal at reduced pressure, the residue was chromatographed (16.7% to 33.3% EtOAc/hexane) to give 246 mg (99%) of ethyl(E)-3-{5-[3'-(1-adamantyl)-4'-benzyloxyphenyl]-2-pyridinyl}-2-propenoate as a pale-yellow solid, mp 49-52° C. $^1$H NMR (CDCl$_3$) δ 1.34 (t, J=7.0 Hz, 3H, OCH$_2$CH$_3$), 1.75 (bs, 6H, AdCH$_2$), 2.07 (bs, 3H, AdCH), 2.20 (bs, 6H, AdCH$_2$), 4.29 (q, J=7.0 Hz, 2H, OCH$_2$CH$_3$), 5.18 (s, 2H, ArCH$_2$), 6.91 (d, J=15.2 Hz, 1H, CH=CHCO), 7.07 (d, J=8.5 Hz, 1H, 5'-ArH), 7.28-7.53 (m, 8H, C$_5$H$_5$, 2', 6'-ArH, 3-ArH), 7.73 (d, J=15.2 Hz, 1H, CH=CHCO), 7.86 (dd, J=2.4 Hz, 8.5 Hz, 1H, 4-ArH), 8.86 ppm (d, J=2.4 Hz, 1H, 6-ArH). HRMS calcd C$_{33}$H$_{35}$NO$_3$ [M+H]$^+$ 494.2690. found 494.2687.

c) Ethyl(E)-3-{5-[3'-(1-adamantyl)-4'-hydroxyphenyl]-2-pyridinyl}-2-propenoate

A solution of ethyl(E)-3-{5-[3'-(1-adamantyl)-4'-benzyloxyphenyl]-2-pyridinyl}-2-propenoate (225 mg, 0.46 mmol), 1.0 M boron tribromide (1.82 mmol) in CH$_2$Cl$_2$ (1.8 mL), and CH$_2$Cl$_2$ (4.5 mL) was stirred at −78° C. under argon for 2 h, then quenched with water (30 mL), and extracted with EtOAc (120 mL). The extract was washed (water and brine) and dried. After solvent removal at reduced pressure, the residue was chromatographed (14% to 50% EtOAc/hexane) to give 168 mg (91%) of ethyl(E)-3-{5-[3'-(1-adamantyl)-4'-hydroxyphenyl]-2-pyridinyl}-2-propenoate as a yellow solid, mp 197-199° C. $^1$H NMR (CDCl$_3$) δ 1.35 (t, J=7.3 Hz, 3H, OCH$_2$CH$_3$), 1.80 (bs, 6H, AdCH$_2$), 2.11 (bs, 3H, AdCH), 2.18 (bs, 6H, AdCH$_2$), 4.29 (q, J=7.3 Hz, 2H, OCH$_2$CH$_3$), 5.31 (br s, 1H, OH), 6.77 (d, J=8.5 Hz, 1H, 5'-ArH), 6.91 (d, J=15.9 Hz, 1H, CH=CHCO), 7.32 (dd, J=2.4 Hz, 8.5 Hz, 1H, 6'-ArH), 7.46 (d, J=2.4 Hz, 1H, 2'-ArH), 7.48 (d, J=7.90, 1H, 3-ArH), 7.73 (d, J=15.9 Hz, 1H, CH=CHCO), 7.86 (dd, J=2.4 Hz, 7.90 Hz, 1H, 4-ArH), 8.85 ppm (d, J=2.4 Hz, 1H, 6-ArH). HRMS calcd C$_{26}$H$_{29}$NO$_3$ [M+H]$^+$ 404.2220. found 404.2223.

Example 10

Synthesis of Compound 25: (E)-3-[2-(5'-(1-Adamantyl)-4'-hydroxy-2'-methylphenyl)-5-pyrimidinyl]-2-propenoic acid To a solution of ethyl(E)-3-[2-(5'-(1-adamantyl)-4'-hydroxy-2'-methylphenyl)-5-pyrimidinyl]-2-propenoate (175 mg, 0.42 mmol) in MeOH (5 mL) was added 5 M aq. NaOH (0.42 mL, 2.09 mmol). The mixture was heated at 82° C. under argon for 50 min, cooled to room temperature, quenched with 2 N HCl (20 mL), and extracted with EtOAc (90 mL). The extract was washed (brine) and dried. The concentrated residue was washed with CH$_2$Cl$_2$ and hexane, and the yellow solid was crystallized (MeOH) to give 162 mg (99%) of (E)-3-[2-(5'-(1-adamantyl)-4'-hydroxy-2'-methylphenyl)-5-pyrimidinyl]-2-propenoic acid as a yellow powder, mp 256-259° C. IR 3302, 2904, 2850, 1714, 1444, 1402, 1233 cm$^{-1}$; $^1$H NMR (DMSO-d$_6$) δ 1.71 (bs, 6H, AdCH$_2$), 2.02 (bs, 311, AdCH), 2.06 (m, 6H, AdCH$_2$), 2.47 (s, 3H, CH$_3$), 6.67 (s, 1H, 3'-ArH), 6.76 (d, J=16.2 Hz, 1H, CH=CHCO), 7.59 (d, J=16.2 Hz, 1H, CH=CHCO), 7.88 (s, 1H, 6'-ArH), 9.12 (s, 2H, 4, 6-ArH), 9.72 ppm (s, 111, OH).

The intermediate, ethyl(E)-3-[2-(5'-(1-adamantyl)-4'-hydroxy-2'-methylphenyl)-5-pyrimidinyl]-2-propenoate was prepared as follows.

(a) Ethyl(E)-3-(2-chloro-5-pyrimidinyl)-2-propenoate

A solution of 5-bromo-2-chloropyrimidine (4.03 g, 20.8 mmol), ethyl acrylate (9.06 mL, 83.3 mmol), palladium(II)

acetate (187 mg, 0.830 mmol), and tri(o-tolyl)phosphine (762 mg, 2.50 mmol) in DMF (22 mL) and diisopropylethylamine (11 mL) was heated at reflux (115° C. oil bath) for 3.5 h, cooled to room temperature, and diluted with brine. The suspension was extracted with EtOAc (300 mL). The extract was washed (brine) and dried. After solvent removal at reduced pressure, the residue was purified on silica gel (11% EtOAc/hexane) to give 3.26 g (73%) of ethyl(E)-3-(2-chloro-5-pyrimidinyl)-2-propenoate as a yellow solid, mp 125°-127° C. IR 2905, 1698, 1542, 1405, 1160 cm$^{-1}$; $^1$H NMR (CDCl$_3$) δ 1.38 (t, J=7.2 Hz, 3H, OCH$_2$CH$_3$), 4.32 (q, J=7.2 Hz, 2H, OCH$_2$CH$_3$), 6.60 (d, J=16.2 Hz, 1H, CH=CHCO), 7.61 (d, J=16.2 Hz, 1H, CH=CHCO), 8.79 (s, 2H, 4-ArH, 6-ArH). HRMS calcd C$_9$H$_9$ClN$_2$O$_2$ [M+H]$^+$ 213.0425. found 213.0428.

(b) 2-(1-Adamantyl)-4-bromo-5-methylphenol

A mixture of 4-bromo-3-methylphenol (4.68 g, 25 mmol), 1-adamantanol (3.81 g, 25 mmol), and MeSO$_3$H (1.2 mL) in CH$_2$Cl$_2$ (18 mL) was stirred and heated at 54° C. (oil-bath) for 28.8 h. The resulting solution was diluted with CHCl$_3$ (150 mL), washed with H$_2$O, 5% NaHCO$_3$, and brine and dried. The residue obtained on concentration was washed with hot hexane to give 6.77 g (85%) of 2-(1-adamantyl)-4-bromo-5-methylphenol as a white solid, mp 155-156° C. IR 3541, 2905, 2845, 1147 cm$^{-1}$; $^1$H NMR δ (CDCl$_3$) 1.77 (bs, 6H, AdCH$_2$), 2.07 (bs, 9H, AdCH and AdCH$_2$), 2.28 (s, 3H, CH$_3$), 4.67 (s, 1H, OH), 6.54 (s, 1H, 6-ArH), 7.30 (s, 1H, 3-ArH).

(c) 5-(1-Adamantyl)-4-benzyloxy-2-methylphenyl bromide

To a solution of 2-(1-adamantyl)-4-bromo-5-methylphenol (6.53 g, 20.34 mmol) in acetone (65 mL) was added benzyl bromide (3.48 g, 20.34 mmol) followed by K$_2$CO$_3$ (3.51 g, 25.43 mmol). The mixture was stirred and heated at reflux for 24 h under argon. Acetone was removed at reduced pressure, and then 2 N HCl (80 mL) was added. The mixture was extracted with EtOAc (300 mL), and the organic layer was washed with H$_2$O and brine and dried. After removal of solvent, the residue was purified by chromatography on a silica gel using hexane to give 7.68 g (80%) of 5-(1-adamantyl)-4-benzyloxy-2-methylphenyl bromide as a white solid, mp 138-139° C. IR 2903, 2848, 1163 cm$^{-1}$; $^1$H NMR (CDCl$_3$) δ 1.71 (bs, 614, AdCH$_2$), 2.02 (bs, 3H, AdCH), 2.08 (bs, 6H, AdCH$_2$), 2.33 (s, 3H, CH$_3$), 5.07 (s, 2H, C$_6$H$_5$CH$_2$), 6.80 (s, 1H, 3-ArH), 7.33 (s, 1H, 6-ArH), 7.3-7.5 ppm (m, 5H, C$_6$H$_5$).

(d) 5-(1-Adamantyl)-4-benzyloxy-2-methylphenylboronic Acid

To a solution of 5-(1-adamantyl)-4-benzyloxy-2-methylphenyl bromide (2.66 g, 6.47 mmol) in THF (10 mL) at −78° C. (dry ice/acetone bath) under argon was added 1.6 M n-BuLi (11.64 mmol) in hexane (7.3 mL) in one portion. This mixture was stirred at −78° C. for 15 min. Tri(isopropyl)borate (4.5 mL, 19.40 mmol) was added, and the resulting solution was stirred at −78° C. for 20 min before being allowed to warm to room temperature with stirring overnight. The reaction mixture was quenched with 1 N HCl (40 mL) and then extracted with EtOAc (100 and 60 mL). The combined organic extracts were washed with brine and dried. Solvents were removed at reduced pressure, and the residue was washed with hexane to give 1.47 g (60%) of 5-(1-adamantyl)-4-benzyloxy-2-methylphenylboronic acid as a white solid, mp 243-247° C. IR 3226, 2903, 2848, 1328 cm$^{-1}$; $^1$H NMR (CDCl$_3$) δ 1.74 (bs, 6H, AdCH$_2$), 2.05 (bs, 3H, AdCH), 2.20 (bs, 6H, AdCH$_2$), 2.82 (s, 3H, CH$_3$), 5.19 (s, 2H, C$_6$H$_5$CH$_2$), 6.85 (s, 1H, 3-ArH), 7.31-7.54 (m, 5H, C$_6$H$_5$), 8.19 ppm (s, 1H, 6-ArH).

e) Ethyl(E)-3-[2-(5'-(1-adamantyl)-4'-benzyloxy-2'-methylphenyl)-5-pyrimidinyl]-2-propenoate To a solution of 5-(1-adamantyl)-4-benzyloxy-2-methylphenylboronic acid (403 mg, 1.07 mmol) and ethyl(E)-3-(2-chloro-5-pyrimidinyl)-2-propenoate (189 mg, 0.89 mmol) in dimethoxyethane (5 mL, degassed) was added tetrakis(triphenylphosphine)palladium (124 mg, 0.10 mmol) and degassed 2 M Na$_2$CO$_3$ (1 mL). The reaction mixture was heated at reflux (90° C. oil-bath) for 20 h, cooled to room temperature, and diluted with EtOAc (130 mL). The organic extract was washed (H$_2$O and brine) and then dried. After solvent removal at reduced pressure, the residue was purified on silica gel (12.5% to 14.3% EtOAc/hexane) to give 310 mg (68%) of ethyl(E)-3-[2-(5'-(1-adamantyl)-4'-benzyloxy-2'-methylphenyl)-5-pyrimidinyl]-2-propenoate as a cream solid, mp 168-170° C. IR 2903, 2848, 1712, 1434, 1227 cm$^{-1}$; $^1$H NMR δ (CDCl$_3$) 1.37 (t, J=7.2 Hz, 3H, OCH$_2$CH$_3$), 1.73 (bs, 6H, AdCH$_2$), 2.04 (bs, 3H, AdCH), 2.18 (bs, 6H, AdCH$_2$), 2.61 (s, 3H, CH$_3$), 4.31 (q, J=7.2 Hz, 2H, OCH$_2$CH$_3$), 5.19 (s, 2H, C$_6$H$_5$CH$_2$), 6.58 (d, J=16.2 Hz, 1H, CH=CHCO), 6.86 (s, 1H, 3'-ArH), 7.32-7.55 (m, 5H, C$_6$H$_5$), 7.65 (d, J=16.2 Hz, 1H, CH=CHCO), 7.95 (s, 1H, 6'-ArH), 8.92 ppm (s, 2H, 4, 6-ArH).

(f) Ethyl(E)-3-[2-(5'-(1-Adamantyl)-4'-hydroxy-2'-methylphenyl)-5-pyrimidinyl]-2-propenoate A solution of ethyl(E)-3-[2-(5'-(1-adamantyl)-4'-benzyloxy-2'-methylphenyl)-5-pyrimidinyl]-2-propenoate (303 mg, 0.60 mmol), and 1.0 M boron tribromide (2.40 mmol) in CH$_2$Cl$_2$ (3.4 mL) in CH$_2$Cl$_2$ (6.0 mL) was stirred at −78° C. under argon for 2 h, quenched with water (20 mL) and sat. NaHCO$_3$ (10 mL), and extracted with EtOAc (130 mL). The extract was washed (brine) and dried. After solvent removal at reduced pressure, the residue was purified on silica gel (12.5% to 20% EtOAc/hexane) to give 233 mg (93%) of ethyl(E)-3-[2-(5'-(1-adamantyl)-4'-hydroxy-2'-methylphenyl)-5-pyrimidinyl]-2-propenoate as a yellow solid, mp 220-223° C. IR 3325, 2904, 2849, 1711, 1439, 1230 cm$^{-1}$; $^1$H NMR δ (CDCl$_3$) 1.36 (t, J=7.2 Hz, 3H, OCH$_2$CH$_3$), 1.78 (bs, 6H, AdCH$_2$), 2.09 (bs, 3H, AdCH), 2.16 (bs, 6H, AdCH$_2$), 2.54 (s, 3H, CH$_3$), 4.30 (q, J=7.2 Hz, 2H, OCH$_2$CH$_3$), 5.14 (s, 1H, OH), 6.56 (s, 1H, 3'-ArH), 6.58 (d, J=16.2 Hz, 1H, CH=CHCO), 7.64 (d, J=16.2 Hz, 1H, CH=CHCO), 7.91 (s, 1H, 6'-ArH), 8.91 ppm (s, 2H, 4,6-ArH).

Example 11

Synthesis of Compound 26: (E)-3-[2-(5'-(1-Adamantyl)-4'-hydroxy-2'-methoxyphenyl)-5-pyrimidinyl]-2-propenoic acid To a solution of ethyl(E)-3-[2-(5'-(1-adamantyl)-4'-hydroxy-2'-methoxyphenyl)-5-pyrimidinyl]-2-propenoate (50 mg, 0.12 mmol) in MeOH (2 mL) was added 5 M aq. NaOH (0.12 mL, 0.58 mmol). The reaction mixture was heated at 82° C. under argon for 50 min, cooled to room temperature, and quenched with 2 N HCl (20 mL). The collected yellow solid was washed three times with distilled H$_2$O, twice with Et₂O, and twice with CH₂Cl₂ (2×), and then crystallized (MeOH) to give 45 mg (96%) of (E)-3-[2-(5'-(1-adamantyl)-4'-hydroxy-2'-methoxyphenyl)-5-pyrimidinyl]-2-propenoic acid as a yellow powder, mp 283-286° C. (dec). IR 3352, 2903, 2850, 1707, 1563, 1285 cm⁻¹; ¹H NMR δ (CDCl₃+ CD₃OD) 1.63 (bs, 6H, AdCH₂), 1.94 (bs, 3H, AdCH), 1.97 (bs, 6H, AdCH₂), 4.00 (s, 3H, OCH₃), 6.45 (s, 1H, 3'-ArH), 6.63 (d, J=16.2 Hz, 1H, CH=CHCO), 7.51 (d, J=16.2 Hz, 1H, CH=CHCO), 8.25 (s, 1H, 6'-ArH), 9.17 ppm (s, 2H, 4, 6-ArH).

The intermediate, ethyl(E)-3-[2-(5'-(1-adamantyl)-4'-hydroxy-2'-methoxyphenyl)-5-pyrimidinyl]-2-propenoate was prepared as follows.

(a) 3-(1-Adamantyl)-4-bromo-5-methoxyphenol and 2-(1-adamantyl)-4-bromo-5-methoxyphenol A mixture of 4-bromo-3-methoxyphenol (6.33 g, 31.18 mmol), 1-adamantanol (4.75 g, 31.18 mmol) and MeSO₃H (1.3 mL) in CH₂Cl₂ (22 mL) was stirred with heating at 54° C. (oil-bath) for 29 h. The resulting solution was quenched with H₂O (30 mL) and extracted with EtOAc (140 mL). The extract was washed with H₂O, 5% NaHCO₃, and brine and dried. The residue obtained on concentration was purified on silica gel (0% to 15% EtOAc/hexane) to give 5.77 g (55%) of 3-(1-adamantyl)-4-bromo-5-methoxyphenol as a white solid, mp 151-153° C. and 2.71 g (26%) of 2-(1-adamantyl)-4-bromo-5-methoxyphenol as a white solid, mp 182-185° C. 3-(1-Adamantyl)-4-bromo-5-methoxyphenol: IR 3515, 2902, 2848, 1312, 1216 cm⁻¹; ¹H NMR δ (CDCl₃) 1.75 (bs, 6H, AdCH₂), 2.04 (bs, 9H, AdCH and AdCH₂), 3.79 (s, 311, OCH₃), 5.29 (s, 1H, OH), 6.57 (s, 1H, 6-ArH), 7.19 ppm (s, 1H, 2-ArH). 2-(1-Adamantyl)-4-bromo-5-methoxyphenol: IR 3513, 2902, 2848, 1389, 1207 cm⁻¹; ¹H NMR δ (CDCl₃) 1.77 (bs, 6H, AdCH₂), 2.06 (bs, 9H, AdCH and AdCH₂), 3.83 (s, 3H, OCH₃), 4.83 (s, 1H, OH), 6.29 (s, 1H, 6-ArH), 7.31 ppm (s, 1H, 3-ArH).

b) 5-(1-Adamantyl)-4-benzyloxy-2-methoxyphenyl bromide

To a stirred solution of 2-(1-adamantyl)-4-bromo-5-methoxyphenol (2.59 g, 7.68 mmol) in acetone (26 mL) was added benzyl bromide (1.31 g, 7.68 mmol) followed by K₂CO₃ (1.33 g, 9.60 mmol). The mixture was stirred and heated at reflux for 17.25 h under argon. Acetone was removed at reduced pressure before 1 N HCl (40 mL) was added. The mixture was extracted with EtOAc (100 mL), and the organic layer was washed with H₂O and brine and dried. After removal of solvent at reduced pressure, the residue was purified on silica gel (0% to 4% EtOAc/hexane) to give 2.50 g (76%) of 5-(1-adamantyl)-4-benzyloxy-2-methoxyphenyl bromide as a white solid, mp 124-126° C. IR 2902, 2847, 1498, 1161 cm⁻¹; ¹H NMR (CDCl₃) δ 1.71 (bs, 6H, AdCH₂), 2.02 (bs, 311, AdCH), 2.08 (bs, 6H, AdCH₂), 3.82 (s, 3H, OCH₃), 5.12 (s, 2H, C₆H₅CH₂), 6.53 (s, 1H, 3-ArH), 7.34 (s, 1H, 6-ArH), 7.31-7.50 ppm (m, 5H, C₆H₅).

(c) 5-(1-Adamantyl)-4-benzyloxy-2-methoxyphenylboronic acid

To a solution of 5-(1-adamantyl)-4-benzyloxy-2-methoxyphenyl bromide (1.86 g, 4.35 mmol) in THF (8 mL) at −78° C. (dry ice/acetone bath) under argon was added 1.6 M n-BuLi (6.96 mmol) in hexane (4.4 mL) in one portion. The mixture was stirred at −78° C. for 15 min. Tri(isopropyl) borate (3.00 mL, 13.0 mmol) was added, and the resulting solution was stirred at −78° C. for 20 min before being allowed to warm to room temperature with stirring overnight. The mixture was quenched with 1 N HCl (40 mL) and then extracted with EtOAc (100 and 40 mL). The combined organic extracts were washed with brine and dried. Solvents were removed at reduced pressure, and the residue was washed with hexane to give 1.47 g (79%) of ethyl(E)-3-[2-(5'-(1-adamantyl)-4'-benzyloxy-2'-methoxyphenyl)-5-pyrimidinyl]-2-propenoate as a light-gray solid, mp 150-152° C. IR 3389, 2902, 2849, 1400, 1260 cm⁻¹; ¹H NMR (CDCl₃) δ 1.71 (bs, 6H, AdCH₂), 2.03 (bs, 3H, AdCH), 2.13 (bs, 6H, AdCH₂), 3.85 (s, 3H, OCH₃), 5.17 (s, 211, C₆H₅CH₂), 6.51 (s, 1H, 3-ArH), 7.32-7.52 (m, 5H, C₆H₅), 7.68 ppm (s, 1H, 6-ArH).

(d) Ethyl(E)-3-[2-(5'-(1-adamantyl)-4'-benzyloxy-2'-methoxyphenyl)-5-pyrimidinyl]-2-propenoate To a solution of 5-(1-adamantyl)-4-benzyloxy-2-methoxyphenylboronic acid (471 mg, 1.20 mmol) and ethyl(E)-3-(2-chloro-5-pyrimidinyl)-2-propenoate (213 mg, 1.00 mmol) in DME (6 mL, degassed) was added tetrakis(triphenylphosphine)palladium (138 mg, 0.12 mmol) and degassed 2 M Na₂CO₃ (1.2 mL). The reaction mixture was heated at reflux (90° C. oil-bath) for 26 h, cooled to room temperature, quenched with 1 N HCl (40 mL), and extracted with EtOAc (190 mL). The extract was washed (H₂O and brine) and dried. After solvent removal at reduced pressure, the residue was purified on silica gel (20% to 33% EtOAc/hexane) to give 368 mg (70%) of ethyl(E)-3-[2-(5'-(1-adamantyl)-4'-benzyloxy-2'-methoxyphenyl)-5-pyrimidinyl]-2-propenoate as a light-yellow solid, mp 72-74° C. IR 2903, 2849, 1712, 1435, 1181 cm⁻¹; ¹H NMR δ (CDCl₃) 1.36 (t, J=7.2 Hz, 3H, OCH₂CH₃), 1.72 (bs, 6H, AdCH₂), 2.04 (bs, 3H, AdCH), 2.17 (bs, 6H, AdCH₂), 3.85 (s, 3H, OCH₃), 4.31 (q, J=7.2 Hz, 2H, OCH₂CH₃), 5.22 (s, 2H, C₆H₅CH₂), 6.57 (d, J=16.2 Hz, 1H, CH=CHCO), 6.62 (s, 1H, 3'-ArH), 7.32-7.54 (m, 5H, C₆H₅), 7.63 (d, J=16.2 Hz, 1H, CH=CHCO), 7.84 (s, 1H, 6'-ArH), 8.93 ppm (s, 2H, 4, 6-ArH).

(e) Ethyl(E)-3-[2-(5'-(1-adamantyl)-4'-hydroxy-2'-methoxyphenyl)-5-pyrimidinyl]-2-propenoate A solution of ethyl(E)-3-[2-(5'-(1-adamantyl)-4'-benzyloxy-2'-methoxyphenyl)-5-pyrimidinyl]-2-propenoate (140 mg, 0.27 mmol), 1.0 M boron tribromide (1.07 mmol) in CH₂Cl₂ (1.1 mL), and CH₂Cl₂ (3.0 mL) was stirred at −78° C. under argon for 2 h, quenched with water (25 mL) and sat. NaHCO₃ (15 mL), and extracted with EtOAc (130 mL). The extract was washed (brine) and dried. After solvent removal at reduced pressure, the residue was purified on silica gel (25% to 50% EtOAc/hexane) to give 75 mg (65%) of ethyl(E)-3-[2-(5'-(1-adamantyl)-4'-hydroxy-2'-methoxyphenyl)-5-pyrimidinyl]-2-propenoate as a yellow solid, mp 239-241° C. IR 3231, 2904, 2850, 1712, 1437, 1181 cm⁻¹; ¹H NMR δ (CDCl₃) 1.36 (t, J=7.2 Hz, 3H, OCH₂CH₃), 1.79 (bs, 6H, AdCH₂), 2.10 (bs, 3H, AdCH), 2.17 (bs, 6H, AdCH₂), 3.36 (s, 3H, OCH₃), 4.30 (q, J=7.2 Hz, 2H, OCH₂CH₃), 6.11 (s, 1H, 3'-ArH), 6.57 (d, J=16.2 Hz, 1H, CH=CHCO), 7.61 (d, J=16.2 Hz, 1H, CH=CHCO), 7.81 (s, 1H, 6'-ArH), 8.29 (bs, 1H, OH), 8.93 ppm (s, 2H, 4, 6-ArH).

Example 12

Synthesis of Compound 27: (E)-3-[2-(3'-(1-Adamantyl)-4',5'-methylenedioxyphenyl)-5-pyrimidinyl]-2-propenoic acid To a solution of ethyl(E)-3-[2-(3'-(1-adamantyl)-4',5'-methylenedioxyphenyl)-5-pyrimidinyl]-2-propenoate (138 mg, 0.32 mmol) in THF/MeOH/H$_2$O (3:2:1, 6.2 mL) was added 5 M aq. NaOH (0.32 mL, 1.60 mmol). The mixture was heated at 80° C. under argon for 1 h, cooled to room temperature, quenched with 1 N HCl (30 mL) and extracted with EtOAc (170 mL). After solvent removal at reduced pressure, the residue was washed with hexane and then with CH$_2$Cl$_2$ and dried to give 128 mg (99%) of (E)-3-[2-(3'-(1-adamantyl)-4', 5'-methylenedioxyphenyl)-5-pyrimidinyl]-2-propenoic acid as a yellow powder, mp 347°-350° C. (dec.). IR 3435, 2900, 2849, 1669, 1418, 1130 cm$^{-1}$; $^1$H NMR δ (DMSO-d$_6$) 1.73 (bs, 6H, AdCH$_2$), 2.02 (bs, 6H, AdCH$_2$), 2.05 (bs, 3H, AdCH), 6.09 (s, 2H, CH$_2$), 6.78 (d, J=16.2 Hz, 1H, CH=CHCO), 7.57 (d, J=16.2 Hz, 1H, CH=CHCO), 7.72 (d, J=1.8 Hz, 1H, 6'-ArH), 7.99 (d, J=1.8 Hz, 1H, 6'-ArH), 9.13 ppm (s, 2H, 4, 6-ArH).

The intermediate, ethyl(E)-3-[2-(3'-(1-adamantyl)-4',5'-methylenedioxyphenyl)-5-pyrimidinyl]-2-propenoate was prepared as follows.

(a) 4-(1-Adamantyl)-6-bromobenzo[1,3]dioxole

A mixture of 4-bromo-1,2-methylenedioxybenzene (2.00 g, 9.95 mmol), 1-adamantanol (1.52 g, 9.95 mmol), and MeSO$_3$H (5 mL) was stirred for 1 h. The resulting solution was quenched with H$_2$O (40 mL) and extracted with EtOAc (110 mL). The extract was washed with 0.5 N NaOH, sat. NaHCO$_3$, and brine and dried. The residue obtained on concentration was purified on silica gel (hexane) to give 2.86 g (86%) of 4-(1-adamantyl)-6-bromobenzo[1,3]dioxole as a white solid, mp 135-136° C. IR 2901, 2843, 1435, 1189 cm$^{-1}$; $^1$H NMR δ (CDCl$_3$) 1.76 (bs, 6H, AdCH$_2$), 1.98 (bs, 6H, AdCH$_2$), 2.06 (bs, 3H, AdCH), 5.93 (s, 2H, CH$_2$), 6.84 (s, 1H, 7-ArH), 6.86 ppm (s, 1H, 5-ArH).

(b) 3-(1-Adamantyl)-4,5-methylenedioxyphenylboronic Acid

To a solution of 4-(1-adamantyl)-6-bromobenzo[1,3]dioxole (2.10 g, 6.26 mmol) in THF (11 mL) at −78° C. (dry ice/acetone bath) under argon was added 1.6 M n-BuLi (10.0 mmol) in hexane (6.26 mL) in one portion. This mixture was stirred at −78° C. for 15 min. Tri(isopropyl)borate (4.30 mL, 18.8 mmol) was added, and the resulting solution was stirred at −78° C. for 20 min more before being allowed to warm to room temperature with stirring overnight. The mixture was quenched with 1 N HCl (40 mL) and then extracted with EtOAc (100 and 40 mL). The combined organic extracts were washed with brine and dried. Solvents were removed at reduced pressure, and the residue was washed with hexane and dried to give 1.23 g (65%) of 3-(1-adamantyl)-4,5-methylenedioxyphenylboronic acid as a cream solid, mp 258-261° C. IR 3231, 2903, 2849, 1343, 1164 cm$^{-1}$; $^1$H NMR δ (CDCl$_3$) 1.81 (bs, 6H, AdCH$_2$), 2.13 (bs, 9H, AdCH$_2$ and AdCH), 6.02 (s, 2H, CH$_2$), 7.48 (s, 1H, 6-ArH), 7.75 ppm (s, 1H, 2-ArH).

(c) Ethyl(E)-3-[2-(3'-(1-adamantyl)-4',5'-methylenedioxyphenyl)-5-pyrimidinyl]-2-propenoate To a solution of 3-(1-adamantyl)-4,5-methylenedioxyphenylboronic acid (288 mg, 0.96 mmol) and ethyl(E)-3-(2-chloro-5-pyrimidinyl)-2-propenoate (170 mg, 0.80 mmol) in dimethoxyethane (6 mL, degassed) was added tetrakis(triphenylphosphine)palladium (111 mg, 0.10 mmol) and degassed 2 M Na$_2$CO$_3$ (1.2 mL). The reaction mixture was heated at reflux (90° C. oil-bath) for 17.3 h, cooled to room temperature, quenched with 1 N HCl (40 mL), and extracted with EtOAc (135 mL). The extract was washed (H$_2$O and brine) and dried. After solvent removal at reduced pressure, the residue was purified on silica gel (17% to 33% EtOAc/hexane) to give 283 mg (82%) of ethyl(E)-3-[2-(3'-(1-adamantyl)-4',5'-methylenedioxyphenyl)-5-pyrimidinyl]-2-propenoate as a light-yellow solid, mp 204-206° C. IR 2900, 2849, 1702, 1422, 1187 cm$^{-1}$; $^1$H NMR δ (CDCl$_3$) 1.36 (t, J=7.2 Hz, 3H, OCH$_2$CH$_3$), 1.80 (bs, 6H, AdCH$_2$), 2.11 (bs, 9H, AdCH and AdCH$_2$), 4.30 (q, J=7.2 Hz, 2H, OCH$_2$CH$_3$), 6.03 (s, 2H, CH$_2$), 6.56 (d, J=16.2 Hz, 1H, CH=CHCO), 7.62 (d, J=16.2 Hz, 1H, CH=CHCO), 7.82 (d, J=1.8 Hz, 1H, 6'-ArH), 7.84 (d, J=1.8 Hz, 1H, 6'-ArH), 8.86 ppm (s, 2H, 4, 6-ArH).

Example 13

Synthesis of Compound 28: (E)-3-[2-(3'-(1-Adamantyl)-4'-hydroxy-5'-methoxyphenyl)-5-pyrimidinyl]-2-propenoic acid To a solution of ethyl(E)-3-[2-(3'-(1-adamantyl)-4'-hydroxy-5'-methoxyphenyl)-5-pyrimidinyl]-2-propenoate (105 mg, 0.24 mmol) in MeOH (3 mL) was added 5 M aq. NaOH (0.24 mL, 1.21 mmol). The mixture was heated at 81° C. under argon for 50 min, cooled to room temperature, quenched with 1 N HCl (20 mL), and extracted with EtOAc (120 mL). The extract was washed (brine) and dried. After solvent removal at reduced pressure, the residue was crystallized (MeOH) to give 90 mg (92%) of (E)-3-[2-(3'-(1-adamantyl)-4'-hydroxy-5'-methoxyphenyl)-5-pyrimidinyl]-2-propenoic acid as a yellow powder, mp 290-293° C. (dec). IR 3503, 2903, 2850, 1695, 1579, 1420, 1217 cm$^{-1}$; $^1$H NMR δ (DMSO-d$_6$) 1.74 (bs, 6H, AdCH$_2$), 2.05 (bs, 3H, AdCH), 2.12 (bs, 6H, AdCH$_2$), 3.88 (s, 3H, OCH$_3$), 6.77 (d, J=16.5 Hz, 1H, CH=CHCO), 7.59 (d, J=16.5 Hz, 1H, CH=CHCO), 7.86 (d, J=1.8 Hz, 1H, 6'-ArH), 8.01 (d, J=1.8 Hz, 1H, 2'-ArH), 9.07 (s, 1H, OH), 9.11 ppm (s, 2H, 4, 6-ArH).

The intermediate, ethyl(E)-3-[2-(3'-(1-adamantyl)-4'-hydroxy-5'-methoxyphenyl)-5-pyrimidinyl]-2-propenoate was prepared as follows.

(a) 2-(1-Adamantyl)-4-bromo-6-methoxyphenol

A mixture of 4-bromo-2-methoxyphenol (2.00 g, 9.85 mmol), 1-adamantanol (1.50 g, 9.85 mmol), and MeSO$_3$H (0.8 mL) in CH$_2$Cl$_2$ (8 mL) was stirred with heating at 54° C. (oil-bath) for 18.3 h. The resulting solution was quenched with H$_2$O (30 mL) and extracted with EtOAc (120 mL). The extract was washed with 5% NaHCO$_3$ and brine and dried. The residue obtained on concentration was purified on silica gel (4% EtOAc/hexane) to give 2.5 g (76%) of 2-(1-adamantyl)-4-bromo-6-methoxyphenol as a white solid, mp 157-159° C. IR 3510, 2903, 2850, 1413, 1217 cm$^{-1}$; $^1$H NMR δ (CDCl$_3$) 1.76 (bs, 6H, AdCH$_2$), 2.07 (bs, 9H, AdCH and AdCH$_2$), 3.87 (s, 3H, OCH$_3$), 5.90 (s, 1H, OH), 6.86 (d, J=2.4 Hz, 1H, 5-ArH), 6.95 ppm (d, J=2.4 Hz, 1H, 3-ArH).

(b) 3-(1-Adamantyl)-4-benzyloxy-5-methoxyphenyl bromide

To a solution of 2-(1-adamantyl)-4-bromo-6-methoxyphenol (3.30 g, 79.78 mmol) in acetone (32 mL) was added benzyl bromide (1.72 g, 10.07 mmol) followed by K$_2$CO$_3$ (1.69 g, 12.2 mmol). This mixture was stirred and heated at reflux temperature for 20.75 h under argon. Acetone was removed at reduced pressure, and 2 N HCl (30 mL) was added. The mixture was extracted with EtOAc (150 mL), and the organic layer was washed with brine and dried. After removal of solvent at reduced pressure, the residue was crystallized (MeOH) to give 3.99 g (95%) of 3-(1-adamantyl)-4-benzyloxy-5-methoxyphenyl bromide as a white solid, mp 89-91° C. IR 2901, 2847, 1444, 1201 cm$^{-1}$; $^1$H NMR (CDCl$_3$) δ 1.67 (m, 6H, AdCH$_2$), 2.00 (bs, 3H, AdCH), 2.05 (bs, 6H, AdCH$_2$), 3.85 (s, 3H, OCH$_3$), 5.07 (s, 2H, C$_6$H$_5$CH$_2$), 6.96 (d, J=2.3 Hz, 1H, 6-ArH), 7.01 (d, J=2.3 Hz, 1H, 2-ArH), 7.30-7.52 ppm (m, 5H, C$_6$H$_5$).

(c)
3-(1-Adamantyl)-4-benzyloxy-5-methoxyphenylboronic acid

To a solution of 3-(1-adamantyl)-4-benzyloxy-5-methoxyphenyl bromide (2.85 g, 6.67 mmol) in THF (12 mL) at −78° C. (dry ice/acetone bath) under argon was added 1.6 M n-BuLi (10.7 mmol) in hexane (6.67 mL) in one portion. This mixture was stirred at −78° C. for 15 min. Tri(isopropyl) borate (4.60 mL, 20.0 mmol) was added next, and the resulting solution was stirred at −78° C. for 20 min before being allowed to warm to room temperature with stirring overnight. The mixture was quenched with 1 N HCl (40 mL) and then extracted with EtOAc (100 and 60 mL). The combined organic extracts were washed with brine and dried. Solvents were removed at reduced pressure, and the residue was washed with hexane and dried to give 2.3 g (88%) of 3-(1-adamantyl)-4-benzyloxy-5-methoxyphenylboronic acid as a cream solid, mp 148-151° C. IR 3219, 2903, 2848, 1410, 1340, 1201 cm$^{-1}$; $^1$H NMR (CDCl$_3$) δ 1.72 (bs, 6H, AdCH$_2$), 2.03 (bs, 3H, AdCH), 2.17 (m, 6H, AdCH$_2$), 3.99 (s, 3H, OCH$_3$), 5.21 (s, 2H, C$_6$H$_5$CH$_2$), 7.31-7.58 (m, 5H, C$_6$H$_5$), 7.68 (d, J=1.4 Hz, 1H, 6-ArH), 7.92 ppm (d, J=1.4 Hz, 1H, 2-ArH).

(d) Ethyl(E)-3-[2-(3'-(1-adamantyl)-4'-benzyloxy-5'-methoxyphenyl)-5-pyrimidinyl]-2-propenoate To a solution of 3-(1-adamantyl)-4-benzyloxy-5-methoxyphenylboronic acid (471 mg, 1.20 mmol) and ethyl(E)-3-(2-chloro-5-pyrimidinyl)-2-propenoate (213 mg, 1.00 mmol) in dimethoxyethane (7.5 mL, degassed) was added tetrakis(triphenylphosphine)palladium (138 mg, 0.12 mmol) and degassed 2 M Na$_2$CO$_3$ (1.5 mL). The reaction mixture was heated at reflux (90° C. oil-bath) for 28.5 h, cooled to room temperature, quenched with 1 N HCl (40 mL), and extracted with EtOAc (110 mL). The extract was washed (brine) and dried. After solvent removal at reduced pressure, the residue was purified on silica gel (16% to 28% EtOAc/hexane) to give 427 mg (81%) of ethyl(E)-3-[2-(3'-(1-adamantyl)-4'-benzyloxy-5'-methoxyphenyl)-5-pyrimidinyl]-2-propenoate as a cream solid, mp 181-183° C. IR 2903, 2849, 1711, 1425, 1178 cm$^{-1}$; $^1$H NMR δ (CDCl$_3$) 1.36 (t, J=7.2 Hz, 3H, OCH$_2$CH$_3$), 1.71 (m, 6H, AdCH$_2$), 2.04 (m, 3H, AdCH), 2.17 (bs, 6H, AdCH$_2$), 4.00 (s, 3H, OCH$_3$), 4.30 (q, J=7.2 Hz, 2H, OCH$_2$CH$_3$), 5.20 (s, 2H, C$_6$H$_5$CH$_2$), 6.58 (d, J=16.2 Hz, 1H, CH=CHCO), 7.32-7.56 (m, 5H, C$_6$H$_5$), 7.63 (d, J=16.2 Hz, 1H, CH=CHCO), 8.00 (d, J=1.8 Hz, 1H, 6'-ArH), 8.15 (d, J=1.8 Hz, 1H, 2'-ArH), 8.90 ppm (s, 2H, 4, 6-ArH).

(e) Ethyl(E)-3-[2-(3'-(1-adamantyl)-4'-hydroxy-5'-methoxyphenyl)-5-pyrimidinyl]-2-propenoate A solution of ethyl(E)-3-[2-(3'-(1-adamantyl)-4'-benzyloxy-5'-methoxyphenyl)-5-pyrimidinyl]-2-propenoate (180 mg, 0.34 mmol), 1.0 M boron tribromide (1.37 mmol) in CH$_2$Cl$_2$ (1.4 mL), and CH$_2$Cl$_2$ (5.0 mL) was stirred at −78° C. under argon for 2 h, quenched with water (20 mL) and sat. NaHCO$_3$ (10 mL), and extracted with EtOAc (100 mL). The extract was washed (brine) and dried. After solvent removal at reduced pressure, the residue was purified on silica gel (20% to 25% EtOAc/hexane) to give 117 mg (78%) of ethyl(E)-3-[2-(3'-(1-adamantyl)-4'-hydroxy-5'-methoxyphenyl)-5-pyrimidinyl]-2-propenoate as a yellow solid, mp 173-175° C. IR 3495, 2903, 2848, 1710, 1419, 1182 cm$^{-1}$; $^1$H NMR δ (CDCl$_3$) 1.36 (t, J=7.2 Hz, 3H, OCH$_2$CH$_3$), 1.80 (m, 6H, AdCH$_2$), 2.11 (m, 3H, AdCH), 2.21 (bs, 6H, AdCH$_2$), 4.02 (s, 3H, OCH$_3$), 4.30 (q, J=7.2 Hz, 2H, OCH$_2$CH$_3$), 6.37 (s, 1H, OH), 6.55 (d, J=16.5 Hz, 1H, CH=CHCO), 7.63 (d, J=16.5 Hz, 1H, CH=CHCO), 7.91 (d, J=1.8 Hz, 1H, 6'-ArH), 8.12 (d, J=1.8 Hz, 1H, 2'-ArH), 8.86 ppm (s, 2H, 4, 6-ArH).

Example 14

Synthesis of Compound 29 and Compound 30: (E)-3-(2-{3'-[1-(4-Oxoadamantyl)]-4'-hydroxyphenyl}-5-pyrimidinyl)-2-propenoic acid (Compound 29) and; 30(E)-3-(2-{3'-[1-(4,4-Dihydroxyadamantyl)]-4'-hydroxyphenyl}-5-pyrimidinyl)-2-propenoic acid (Compound 30

To a solution of ethyl(E)-3-(2-{3'-[1-(4-oxoadamantyl)]-4'-hydroxyphenyl}-5-pyrimidinyl)-2-propenoate (70 mg, 0.17 mmol) in MeOH (2 mL) was added 5 M aq. NaOH (0.17 mL, 0.84 mmol). This mixture was heated at 82° C. under argon for 50 min, cooled to room temperature, quenched with 2 N HCl (20 mL), and extracted with EtOAc (120 mL). The residue obtained after concentration of the extract at reduced temperature and the solid collected from H$_2$O layer were combined and crystallized (MeOH) to give 47 mg (71%) of a mixture of (E)-3-(2-{3'-[1-(4-oxoadamantyl)]-4'-hydroxyphenyl}-5-pyrimidinyl)-2-propenoic acid (Compound 29) and (E)-3-(2-{3'-[1-(4,4-dihydroxyadamantyl)]-4'-hydroxyphenyl}-5-pyrimidinyl)-2-propenoic acid (Compound 30) as a yellow powder. IR 3400, 2933, 2859, 1709, 1418, 1209 cm$^{-1}$; $^1$H NMR δ (CDCl$_3$+CD$_3$OD) 1.49-2.49 (m, 13H, AdCH and AdCH$_2$), 6.40 (d, J=15.9 Hz, 1H, CH=CHCO), 6.65 or 6.68 (d, J=7.9 Hz or 8.5 Hz, 1H, 5'-ArH), 7.43 (d, J=15.9 Hz, 1H, CH=CHCO), 7.90 or 7.93 (dd, J=1.8 Hz, 7.9 Hz or 1.8 Hz, 8.5 Hz, 1H, 6'-ArH), 8.12 (d, J=1.8 Hz, 1H, 2'-ArH), 8.68 ppm (s, 2H, 4, 6-ArH). (Compound 29): LC/MS calcd C$_{23}$H$_{22}$N$_2$O$_4$ m/z 391. found 391. (Compound 30): LC/MS calcd C$_{23}$H$_{24}$N$_2$O$_5$ m/z 408. found 408.

The intermediate, ethyl(E)-3-(2-{3'-[1-(4-oxoadamantyl)]-4'-hydroxyphenyl}-5-pyrimidinyl)-2-propenoate was prepared as follows.

(a) 5-(5'-Bromo-2'-hydroxyphenyl)-2-adamantanone

The mixture of 4-bromophenol (3.11 g, 17.98 mmol), 5-hydroxy-2-adamantanone (2.49 g, 14.98 mmol), and MeSO$_3$H (7 mL) was stirred with heating at 80° C. (oil-bath) for 5 h. The resulting mixture was quenched with H$_2$O (40 mL) and filtered. The precipitate was washed several times with H$_2$O, 5% NaHCO$_3$, and CH$_2$Cl$_2$ and dried to give 3.76 g (79%) of 5-(5'-bromo-2'-hydroxyphenyl)-2-adamantanone as a white solid, mp 287-289° C. $^1$H NMR δ (DMSO-d$_6$) 1.82-2.45 (m, 13H, AdCH and AdCH$_2$), 6.71 (d, J=8.5 Hz, 1H, 3'-ArH), 7.10 (d, J=2.4 Hz, 1H, 4'-ArH), 7.16 (dd, J=2.4 Hz, 8.5 Hz, 1H, 6'-ArH), 9.78 (s, 1H, OH).

(b) 5-(2'-Benzyloxy-5'-bromophenyl)-2-adamantanone

To a solution of 5-(5'-bromo-2'-hydroxyphenyl)-2-adamantanone (4.57 g, 14.20 mmol) in acetone (42 mL) was added benzyl bromide (2.67 g, 15.6 mmol) followed by K$_2$CO$_3$ (2.65 g, 19.2 mmol). The mixture was stirred at reflux for 25.7 h under argon. Acetone was removed, and 2 N HCl (60 mL) was added. The resultant mixture was extracted with EtOAc (250 mL), and the organic layer was washed with brine and dried. After removal of solvent at reduced pressure, the residue was purified on silica gel (14% to 20% EtOAc/hexane) to give 5.48 g (94%) of 5-(2'-benzyloxy-5'-bromophenyl)-2-adamantanone as a white solid, mp 163-165° C. $^1$H NMR (DMSO-d$_6$) δ 1.79-2.42 (m, 13H, AdCH and AdCH$_2$), 5.12 (s, 2H, C$_6$H$_5$CH$_2$), 7.03 (d, J=8.5 Hz, 1H, 3'-ArH), 7.21 (d, J=2.4 Hz, 1H, 4'-ArH), 7.29-7.44 ppm (m, 6H, 6'-ArH, C$_6$H$_5$).

(c) Ketal of 4-benzyloxy-3-[1-(4-oxoadamantyl)]phenyl bromide

The mixture of 5-(2'-benzyloxy-5'-bromophenyl)-2-adamantanone (5.47 g, 13.30 mmol), ethylene glycol (0.96 mL, 17.30 mmol), and p-toluenesulfonic acid monohydrate (140 mg) in benzene (55 mL) was stirred at reflux temperature (110° C. oil-bath) using Dean-Stark apparatus for 24.25 h, cooled to room temperature, and diluted with EtOAc (150 mL). The solution was washed (1 N NaOH and brine) and dried. After removal of solvent at reduced pressure, the residue was purified on silica gel (12% to 14% EtOAc/hexane) to give 5.77 g (95%) of the ethyleneglycol ketal of 4-benzyloxy-3-[1-(4-oxoadamantyl)]phenyl bromide as a white solid, mp 90-91° C. $^1$H NMR (CDCl$_3$) δ 1.54-2.35 (m, 13H, AdCH and AdCH$_2$), 3.91 (m, 4H, CH$_2$CH$_2$), 5.07 (s, 2H, C$_6$H$_5$CH$_2$), 6.78 (d, J=8.5 Hz, 1H, 3'-ArH), 7.23 (dd, J=2.4 Hz, 8.5 Hz, 1H, 6'-ArH), 7.31 (d, J=2.4 Hz, 1H, 4'-ArH), 7.30-7.48 ppm (m, 5H, C$_6$H$_5$).

(d) Ketal of 4-benzyloxy-3-[1-(4-oxoadamantyl)]phenylboronic acid

To a solution of the ketal of 4-benzyloxy-3-[1-(4-oxoadamantyl)]phenyl bromide (5) (2.00 g, 4.39 mmol) in THF (6.5 mL) at −78° C. (dry ice/acetone bath) under argon was added 1.6 M n-BuLi (7.5 mmol) in hexane (4.7 mL) in one portion. The mixture was stirred at −78° C. for 15 min. Tri(isopropyl) borate (3.04 mL, 13.20 mmol) was added, and the resulting solution was stirred at −78° C. for 20 min before being allowed to warm to room temperature with stirring overnight. The mixture was quenched with 3 N HCl (40 mL) and then extracted with EtOAc (100 and 70 mL) The combined organic extracts were washed with brine and dried. Solvents were removed at reduced pressure, and the residue was washed (benzene and hexane) and dried to give 1.3 g (71%) of the ethyleneglycol ketal of 4-benzyloxy-3-[1-(4-oxoadamantyl)] phenylboronic acid as a white solid, mp 161-165° C. $^1$H NMR (CDCl$_3$) δ 1.61-2.49 (m, 13H, AdCH and AdCH$_2$), 3.93 (m, 4H, CH$_2$CH$_2$), 5.21 (s, 2H, C$_6$H$_5$CH$_2$), 7.05 (d, J=8.0 Hz, 1H, 5-ArH), 7.31-7.55 ppm (m, 5H, C$_6$H$_5$), 8.02 (dd, J=1.2 Hz, 8.0 Hz, 1H, 6-ArH), 8.16 (d, J=1.2 Hz, 1H, 2-ArH).

(e) Ketal of ethyl(E)-3-(2-{4'-benzyloxy-3'-[1-(4-oxoadamantyl)]phenyl}-5-pyrimidinyl)-2-propenoate To a solution of the ethyleneglycol ketal of 4-benzyloxy-3-[1-(4-oxoadamantyl)]phenylboronic acid (202 mg, 0.48 mmol) and ethyl(E)-3-(2-chloro-5-pyrimidinyl)-2-propenoate (85 mg, 0.40 mmol) in dimethoxyethane (4 mL, degassed) was added tetrakis(triphenylphosphine)palladium (55 mg, 0.05 mmol) and degassed 2 M Na$_2$CO$_3$ (0.8 mL). The reaction mixture was heated at reflux (90° C. oil-bath) for 20 h, cooled to room temperature, quenched with H$_2$O (25 mL), and extracted with EtOAc (210 mL). The extract was washed (brine) and dried. After solvent removal at reduced pressure, the residue was purified on silica gel (16% to 25% EtOAc/hexane) to give 148 mg (67%) of the ketal of ethyl(E)-3-(2-{4'-benzyloxy-3'-[1-(4-oxoadamantyl)]phenyl}-5-pyrimidinyl)-2-propenoate as a cream solid, mp 60-63° C. IR 2906, 2860, 1711, 1434, 1222 cm$^{-1}$; $^1$H NMR δ (CDCl$_3$) 1.36 (t, J=7.2 Hz, 3H, OCH$_2$CH$_3$), 1.62-2.48 (m, 13H, AdCH and AdCH$_2$), 3.93 (m, 4H, CH$_2$CH$_2$), 4.30 (q, J=7.2 Hz, 2H, OCH$_2$CH$_3$), 5.21 (s, 2H, C$_6$H$_5$CH$_2$), 6.56 (d, J=15.9 Hz, 1H, CH=CHCO), 7.05 (d, J=8.5 Hz, 1H, 5'-ArH), 7.32-7.55 ppm (m, 5H, C$_6$H$_5$), 7.63 (d, J=15.9 Hz, 1H, CH=CHCO), 8.30 (d, J=8.5 Hz, 1H, 6'-ArH), 8.45 (s, 1H, 2'-ArH), 8.86 ppm (s, 2H, 4, 6-ArH).

(f) Ethyl(E)-3-(2-{3'-[1-(4-oxoadamantyl)]-4'-hydroxyphenyl}-5-pyrimidinyl)-2-propenoate A solution of the ketal of ethyl(E)-3-(2-{4'-benzyloxy-3'-[1-(4-oxoadamantyl)]phenyl}-5-pyrimidinyl)-2-propenoate (60 mg, 0.11 mmol), 1.0 M boron tribromide (0.43 mmol) in CH$_2$Cl$_2$ (0.43 mL), and CH$_2$Cl$_2$ (2.0 mL) was stirred at −78° C. under argon for 2 h, quenched with water (25 mL), and extracted with EtOAc (90 mL). The extract was washed (brine) and dried. After solvent removal at reduced pressure, the residue was purified on silica gel (16% to 33% EtOAc/hexane) to give 36 mg (88%) of ethyl(E)-3-(2-{3'-[1-(4-oxoadamantyl)]-4'-hydroxyphenyl}-5-pyrimidinyl)-2-propenoate as a cream solid, mp 231-234° C. IR 3312, 2927, 2858, 1717, 1443, 1185 cm$^{-1}$; $^1$H NMR δ (CDCl$_3$) 1.36 (t, J=7.2 Hz, 3H, OCH$_2$CH$_3$), 1.99-2.70 (m, 13H, AdCH and AdCH$_2$), 4.31 (q, J=7.2 Hz, 2H, OCH$_2$CH$_3$), 6.28 (s, 1H, OH), 6.56 (d, J=15.9 Hz, 1H, CH=CHCO), 6.80 (d, J=8.5 Hz, 1H, 5'-ArH), 7.63 (d, J=15.9 Hz, 1H, CH=CHCO), 8.22 (dd, J=1.8 Hz, 8.5 Hz, 1H, 6'-ArH), 8.38 (d, J=1.8 Hz, 1H, 2'-ArH), 8.87 ppm (s, 2H, 4, 6-ArH).

Example 15

The following illustrate representative pharmaceutical dosage forms, containing a compound of formula I ('Compound X'), for therapeutic or prophylactic use in humans.

| (i) Tablet 1 | mg/tablet |
| --- | --- |
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
| --- | --- |
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
| --- | --- |
| Compound X = | 10.0 |
| Colloidal silicon dioxide | 1.5 |

| | |
|---|---|
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

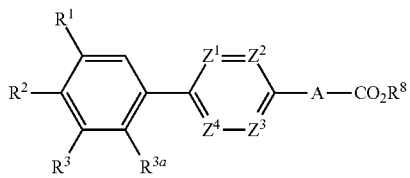

wherein:
$Z^1$ is $CR^4$, $Z^2$ is $CR^5$, $Z^3$ is $CR^6$ and $Z^4$ is N; or $Z^1$ is N, $Z^2$ is $CR^5$, $Z^3$ is $CR^6$ and $Z^4$ is N; or $Z^1$ is $CR^4$, $Z^2$ is N, $Z^3$ is $CR^6$ and $Z^4$ is N; or $Z^1$ is $CR^4$, $Z^2$ is $CR^5$, $Z^3$ is N and $Z^4$ is N;

$R^1$ is adamantyl, nor-adamantyl, bicyclooctyl or $(C_2-C_{10})$alkynyl, wherein any adamantyl, nor-adamantyl, bicyclooctyl or $(C_2-C_{10})$alkynyl of $R^1$ may be optionally substituted with one or more groups selected from —OH, oxo(=O), =CH$_2$, and —NH$_2$;

$R^2$ is —OH, —OC(=O)R$_a$, —OC(=O)NR$_b$R$_c$ or —OC(=O)OR$_a$, and $R^3$ is H, halo, —CN, —NO$_2$, $(C_1-C_6)$alkyl, —OH, $(C_1-C_3)$alkoxy, —NR$_d$R$_e$, —CO$_2$R$_f$, —C(=O)R$_f$, —NR$_f$C(=O)R$_g$, —C(=O)NR$_d$R$_e$, wherein any alkyl or alkoxy of $R^3$ may be optionally substituted with one or more groups selected from halo, oxo, hydroxy, —NR$_{z1}$R$_{z2}$ and $(C_1-C_3)$alkoxy; or $R^2$ and $R^3$ together with the atoms to which they are attached form an alkylenedioxy ring wherein alkylenedioxy ring is optionally substituted with one or more $(C_1-C_6)$alkyl;

$R^{3a}$ is H, halo, —OH, —$(C_1-C_6)$alkyl or $(C_1-C_3)$alkoxy;

A is —CR$_h$=CR$_h$—;

$R^4$ is H, halo, —CN, —NO$_2$, —N$_3$, —OH, $(C_1-C_{10})$alkyl, $(C_1-C_{10})$alkoxy, —NR$_m$R$_n$, —NR$_o$(C=O)R$_p$ or —CO$_2$R, wherein any alkyl or alkoxy of $R^4$ may be optionally substituted with one or more groups selected from halo, oxo, hydroxy, —CN, —NR$_{z1}$R$_{z2}$, —C(=O)NR$_{z1}$R$_{z2}$ and $(C_1-C_3)$alkoxy;

$R^5$ is H or F;

$R^6$ is H or F;

$R^8$ is H, $(C_1-C_6)$alkyl, aryl$(C_1-C_6)$alkyl or aryl;

each R$_a$ is independently $(C_1-C_6)$alkyl, aryl$(C_1-C_6)$alkyl or aryl;

R$_b$ and R$_c$ are each independently selected from H or $(C_1-C_6)$alkyl; or R$_b$, and R$_c$ together with the nitrogen to which they are attached form a pyrrolidino, piperidino, piperazino, azetidino, morpholino, or thiomorpholino;

R$_d$ and R$_e$ are each independently H or $(C_1-C_6)$alkyl; or R$_d$ and R$_e$ together with the nitrogen to which they are attached form a pyrrolidino, piperidino, piperazino, azetidino, morpholino, or thiomorpholino;

each R$_f$ is independently H, $(C_1-C_6)$alkyl, aryl$(C_1-C_6)$alkyl or aryl;

each R$_g$ is independently $(C_1-C_6)$alkyl, aryl$(C_1-C_6)$alkyl or aryl;

each R$_h$ is independently H or F;

R$_m$ and R$_n$ are each independently H or $(C_1-C_6)$alkyl; or R$_m$ and R$_n$ together with the nitrogen to which they are attached form a pyrrolidino, piperidino, piperazino, azetidino, morpholino, or thiomorpholino;

each R$_o$ is independently H, $(C_1-C_6)$alkyl, aryl$(C_1-C_6)$alkyl or aryl;

each R$_p$ is independently $(C_1-C_6)$alkyl, aryl$(C_1-C_6)$alkyl or aryl; and

R$_{z1}$ and R$_{z2}$ are each independently selected from H or $(C_1-C_6)$alkyl; or R$_{z1}$ and R$_{z2}$ together with the nitrogen to which they are attached form a pyrrolidino, piperidino, piperazino, azetidino, morpholino, or thiomorpholino;

or a salt thereof.

2. The compound of claim 1 wherein $Z^1$ is N, $Z^2$ is $CR^5$, $Z^3$ is $CR^6$ and $Z^4$ is N.

3. The compound of claim 1 wherein $Z^1$ is $CR^4$, $Z^2$ is $CR^5$, $Z^3$ is $CR^6$ and $Z^4$ is N.

4. The compound of claim 1 wherein $R^4$ is H or halo.

5. (Original; The compound of claim 1 wherein $Z^1$ is $CR^4$, $Z^2$ is N, $Z^3$ is $CR^6$ and $Z^4$ is N.

6. The compound of claim 1 wherein $Z^1$ is $CR^4$, $Z^2$ is $CR^5$, $Z^3$ is N and $Z^4$ is N.

7. The compound of claim 1 wherein $R^1$ is adamantyl wherein any adamantyl of $R^1$ may be optionally substituted with one or more groups selected from —OH and oxo(=O).

8. The compound of claim 1 wherein $R^2$ is —OH or —OC(=O)R$_a$.

9. The compound of claim 1 wherein $R^3$ is H or $(C_1-C_3)$alkoxy.

10. The compound of claim 1 wherein $R^2$ and $R^3$ together with the atoms to which they are attached form a alkylenedioxy ring, wherein the alkylenedioxy ring is optionally substituted is with one or more $(C_1-C_6)$alkyl.

11. The compound of claim 1 wherein $R^8$ is H or $(C_1-C_6)$alkyl.

12. The compound of claim 1 which is:
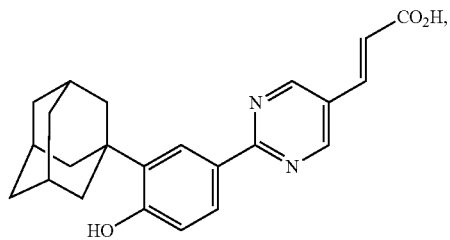
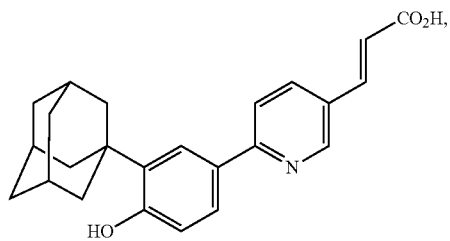
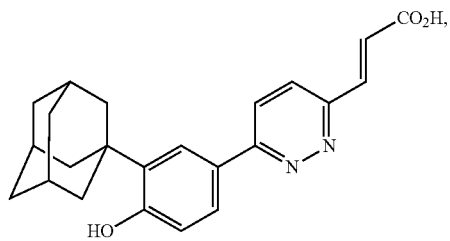
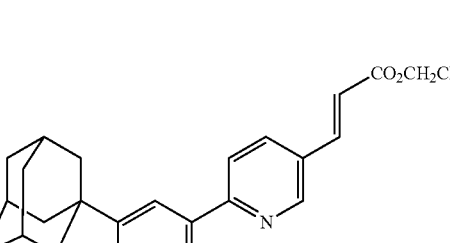
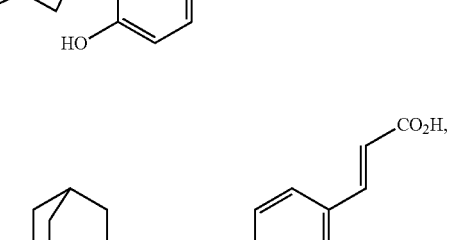
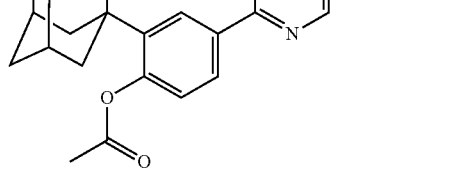
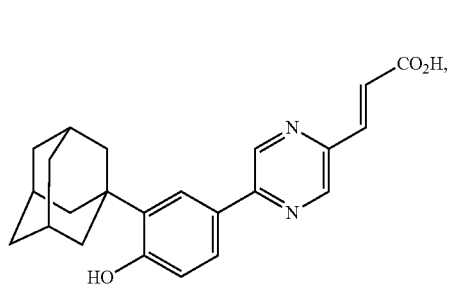
-continued
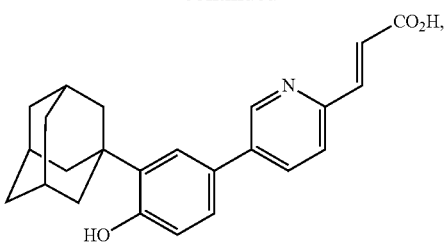
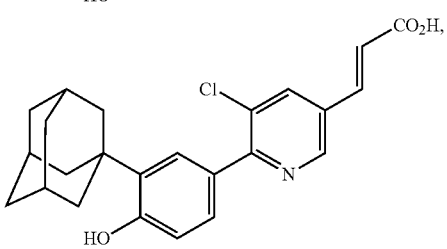
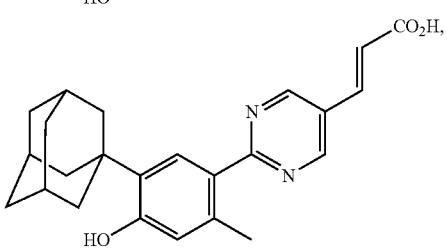
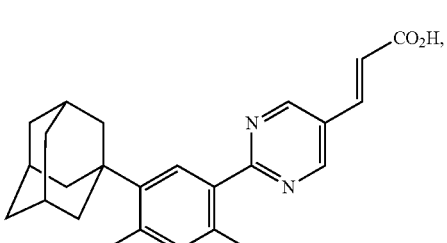
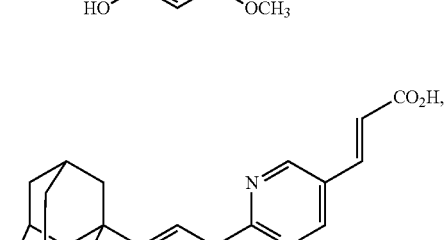
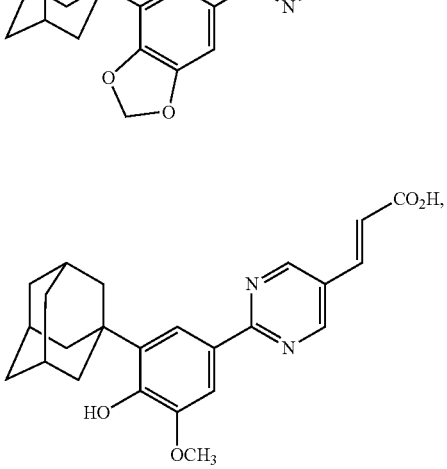

-continued

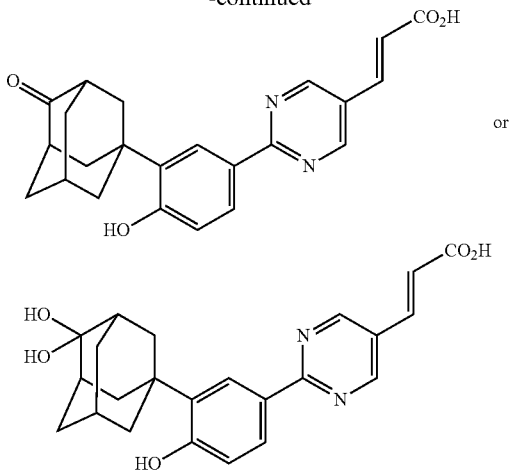

or a salt thereof.

13. A composition comprising a compound as described in claim 1, or a pharmaceutically acceptable salt thereof, and a pharmaceutically acceptable diluent or carrier.

14. A method for inducing cell death or apoptosis in a pancreatic cancer stem cell in a mammal in need of such treatment comprising administering to the mammal an effective amount of a compound as described in claim 1, or a pharmaceutically acceptable salt thereof.

15. The compound of claim 1 wherein:
$Z^1$ is $CR^4$, $Z^2$ is $CR^5$, $Z^3$ is $CR^6$ and $Z^4$ is N; or $Z^1$ is N, $Z^2$ is $CR^5$, $Z^3$ is $CR^6$ and $Z^4$ is N;

$R^1$ is adamantyl, nor-adamantyl, bicyclooctyl or $(C_2$-$C_{10})$alkynyl, wherein any adamantyl, nor-adamantyl, bicyclooctyl or $(C_2$-$C_{10})$alkynyl of $R^1$ may be optionally substituted with one or more groups selected from —OH, oxo(=O), =$CH_2$, and —$NH_2$;

$R^2$ is —OH or —OC(=O)$R_a$ and $R^3$ is H or $(C_1$-$C_3)$alkoxy; or $R^2$ and $R^3$ together with the atoms to which they are attached form an alkylenedioxy;

$R^{3a}$ is H, —$(C_1$-$C_6)$alkyl or $(C_1$-$C_3)$alkoxy;

A is —$CR_h$=$CR_h$—;

$R^4$ is H or halo;

$R^5$ is H or F;

$R^6$ is H or F;

$R^8$ is H or $(C_1$-$C_6)$alkyl;

each $R_a$ is independently $(C_1$-$C_6)$alkyl, aryl$(C_1$-$C_6)$alkyl or aryl; and each $R_h$ is independently H or F;

or a salt thereof.

16. A method for treating cancer in a mammal comprising administering to the mammal an effective amount of compound as described in claim 1, or a pharmaceutically acceptable salt thereof, wherein the cancer is leukemia or pancreatic cancer.

17. A method for treating cancer in a mammal comprising administering to the mammal an effective amount of compound as described in claim 1, or a pharmaceutically acceptable salt thereof, wherein the cancer is acute myelogenous leukemia, chronic myelogenous leukemia or pancreatic cancer.

* * * * *